(12) United States Patent
Ichiba et al.

(10) Patent No.: US 11,133,102 B2
(45) Date of Patent: *Sep. 28, 2021

(54) SERVICE ARCHITECTURE SUPPORT METHOD AND SYSTEM FOR MEDICAL/NURSING SUPPORT SYSTEM

(71) Applicant: EMBRACE CO., LTD., Tokyo (JP)

(72) Inventors: Hironobu Ichiba, Tokyo (JP); Manabu Ito, Tokyo (JP); Yoshihiro Ogura, Tokyo (JP)

(73) Assignee: EMBRACE CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/770,077

(22) PCT Filed: Dec. 4, 2018

(86) PCT No.: PCT/JP2018/044536
§ 371 (c)(1),
(2) Date: Jun. 5, 2020

(87) PCT Pub. No.: WO2019/111885
PCT Pub. Date: Jun. 13, 2019

(65) Prior Publication Data
US 2021/0193304 A1    Jun. 24, 2021

(30) Foreign Application Priority Data

Dec. 5, 2017 (JP) .............................. JP2017-233093

(51) Int. Cl.
*G16H 80/00* (2018.01)
*G16H 10/60* (2018.01)
(Continued)

(52) U.S. Cl.
CPC ........... *G16H 40/20* (2018.01); *G06F 21/629* (2013.01); *G06Q 10/101* (2013.01);
(Continued)

(58) Field of Classification Search
CPC ........ G16H 10/60; G16H 40/67; G16H 50/20; G16H 50/30; G16H 10/20; G16H 40/20;
(Continued)

(56) References Cited

U.S. PATENT DOCUMENTS

2002/0099568 A1\* 7/2002 Turner .................. G06Q 10/10
705/2
2006/0031094 A1    2/2006 Cohen et al.
(Continued)

FOREIGN PATENT DOCUMENTS

JP    2013521546 A    6/2013
JP    2013143125 A    7/2013
(Continued)

OTHER PUBLICATIONS

Asahina, Kan, "Method for establishing information sharing between multiple occupations using groupware Cybozu Live", New Medicine in Japan, vol. 3 9, No. 5, M E Shinko Kyokai KK, May 1, 2012, pp. 41-44.
(Continued)

*Primary Examiner* — Maroun P Kanaan
(74) *Attorney, Agent, or Firm* — CKC & Partners Co., LLC

(57) ABSTRACT

Provided is a service architecture support method with which the content of a new service provided by an application incorporated into a medical/nursing support system can be finely adjusted according to the needs of a patient or a person requiring care, or a medical professional or a nurse. To that end, when an application (220) developed using an application framework (200) is incorporated into a medical/nursing support system (30), an application ID is allocated to the application (220) and the application ID is associated with a group ID and stored, thereby enabling selective use of a new service provided by the application (220) by only
(Continued)

a group member of a group with which the application ID has been associated. Furthermore, the specific function installed in the application (220) can be set in administrator settings according to the needs of a patient or a medical professional from said group.

12 Claims, 49 Drawing Sheets

(51) Int. Cl.
| | | |
|---|---|---|
| *G16H 40/20* | (2018.01) | |
| *G16H 50/70* | (2018.01) | |
| *G16H 10/20* | (2018.01) | |
| *G06F 21/62* | (2013.01) | |
| *G06Q 10/10* | (2012.01) | |
| *H04L 29/08* | (2006.01) | |

(52) U.S. Cl.
CPC ........... *G06Q 10/105* (2013.01); *G16H 10/20* (2018.01); *G16H 10/60* (2018.01); *G16H 50/70* (2018.01); *H04L 67/12* (2013.01)

(58) Field of Classification Search
CPC ........ G16H 80/00; G16H 50/70; G16H 20/10; G16H 40/63; G16H 20/30; G16H 10/40; A61B 5/0022; A61B 5/7275
See application file for complete search history.

(56) References Cited

U.S. PATENT DOCUMENTS

| | | | |
|---|---|---|---|
| 2011/0125844 A1* | 5/2011 | Collier | H04W 4/38 709/204 |
| 2013/0035946 A1* | 2/2013 | Ratan | G06Q 10/10 705/2 |
| 2013/0179859 A1 | 7/2013 | Kang et al. | |
| 2014/0009262 A1 | 1/2014 | Robertson et al. | |
| 2014/0200914 A1 | 7/2014 | Rut et al. | |
| 2015/0317435 A1 | 11/2015 | Klocek et al. | |
| 2016/0117464 A1 | 4/2016 | Ito et al. | |

FOREIGN PATENT DOCUMENTS

| | | |
|---|---|---|
| JP | 2014142929 A | 8/2014 |
| JP | 2015015010 A | 1/2015 |
| JP | 2016021117 A | 2/2016 |
| JP | 2016522914 A | 8/2016 |
| WO | 2011106441 A2 | 9/2011 |
| WO | 2014151929 A1 | 9/2014 |
| WO | 2016123359 A1 | 8/2016 |
| WO | 2017042396 A1 | 3/2017 |

OTHER PUBLICATIONS

Murata, Yuki et al., "LINE, convenient & amazing technique", Impress Japan KK, Jun. 1, 2014, pp. 28, 38.

* cited by examiner

FIG. 4

(a) USER TABLE

| ID | MAIL ID | PASSWORD | REGISTRATION DATE | STATUS |
|---|---|---|---|---|
| 100 | sumida@test.com | tKswU8yq | 2012/12/10 | ENABLED |
| 200 | ogura@test.com | fvXEd5Re | 2012/11/20 | ENABLED |
| 300 | yamada@test.com | acD1V5tp | 2012/12/25 | ENABLED |

(b) PATIENT TABLE

| ID | NAME | SEX | DATE OF BIRTH | MAIL ADDRESS | ADDRESS | TEL |
|---|---|---|---|---|---|---|
| 100 | HISAE SUMIDA | FEMALE | 1945/7/18 | sumida@test.com | 1-2-3 CHUO-CHO, MEGURO-KU | 03-1234-5678 |

(c) MEDICAL WORKER TABLE

| ID | NAME | SEX | DATE OF BIRTH | OCCUPATION |
|---|---|---|---|---|
| 200 | TARO OGURA | MALE | 1963/8/5 | DOCTOR |

(d) MEDICAL-RELATED FACILITY TABLE

| ID | NAME | TYPE | MEDICAL DEPARTMENT | ADDRESS | TEL |
|---|---|---|---|---|---|
| 1000 | YAMADA CLINIC | MEDICAL CLINIC | INTERNAL MEDICINE, SURGERY, PSYCHOSOMATIC MEDICINE, PSYCHIATRY | 1-2-3 OTEMACHI, YAMADA-KU | 03-2345-6789 |

| URL | CONSULTATION TIME |
|---|---|
| http://www.yamada-hp.xxx | CLOSED ON SUNDAYS AND PUBLIC HOLIDAYS |

FIG. 5

(a) MEDICAL-RELATED FACILITY PATIENT TABLE

| | | | | | | | |
|---|---|---|---|---|---|---|---|
| 101 | 1000 | 2012/12/25 | 1-2-3 CHUO-CHO MINATO-KU | 03-1234-5678 | sumida@test.com | RECEIVED | 1 |
| | | | | | | 123 HISAE SUMIDA FEMALE | 1945/7/18 |
| | | | | | | srXjR7L2dBmwO2psAyte | |

(b) DISEASE TABLE

| | DISEASE NAME |
|---|---|
| 1 | 101 ALZHEIMER'S DISEASE |
| 2 | 101 LUNG CANCER |

(c) GROUP TABLE

| | GROUP NAME |
|---|---|
| 10001 | ALZHEIMER'S DISEASE TREATMENT 1 |
| 10002 | LUNG CANCER TREATMENT 2 |

(d) GROUP PARTICIPATION TABLE

| | | | |
|---|---|---|---|
| 1 | 100 | 10001 | C2 |
| 2 | 200 | 10001 | C1,C2 |

FIG.6

(a) INVITATION REQUEST TABLE

| ID | INVITER USER ID | INVITEE USER ID | APPROVAL |
|---|---|---|---|
| 1 | 200 | 201 | ALLOWANCE |

| INVITEE MAIL ADDRESS | INVITEE PASSPHRASE | GROUP ID | ACCESSIBLE TIMELINE |
|---|---|---|---|
| yamanaka@test.com | NICKNAME IS RACCOON DOG | 10001 | C1,C2 |

(b) TIMELINE TABLE

| TIMELINE ID | GROUP ID | NAME |
|---|---|---|
| 1 | 10001 | MEDICAL SIDE |
| 2 | 10001 | PATIENT SIDE |

(c) MEDICAL INFORMATION SHARING RULE TABLE

| USER ID | GROUP ID | HOSPITAL SHARING RULE | MEDICINE SHARING RULE |
|---|---|---|---|
| 100 | 1000 | | |
| 100 | 1001 | | |

(d) NFC TERMINAL TABLE

| ID | | PASSCODE |
|---|---|---|
| 1000 | 3079372621 | 101 srXjR7L2dBmrwO2psAyte |
| 1001 | 2850365002 | 102 TrxlR5Bv3EIshei8Wegkese |

FIG. 7

(a) MESSAGE TRANSMISSION RESERVATION TABLE

| | SENDER | RECEIVER | MESSAGE | TIME |
|---|---|---|---|---|
| 1 | 200 | 100 | IT HAS BEEN THREE DAYS SINCE PRESCRIPTION OF MEDICINE – ARE YOU TAKING IT PROPERLY? | 2012/12/29 |

(b) PATIENT ATTRIBUTE TABLE

| | PATIENT ID | ATTRIBUTE | VALUE |
|---|---|---|---|
| 1 | 101 | MEDICINE PRESCRIPTION | NOT YET |

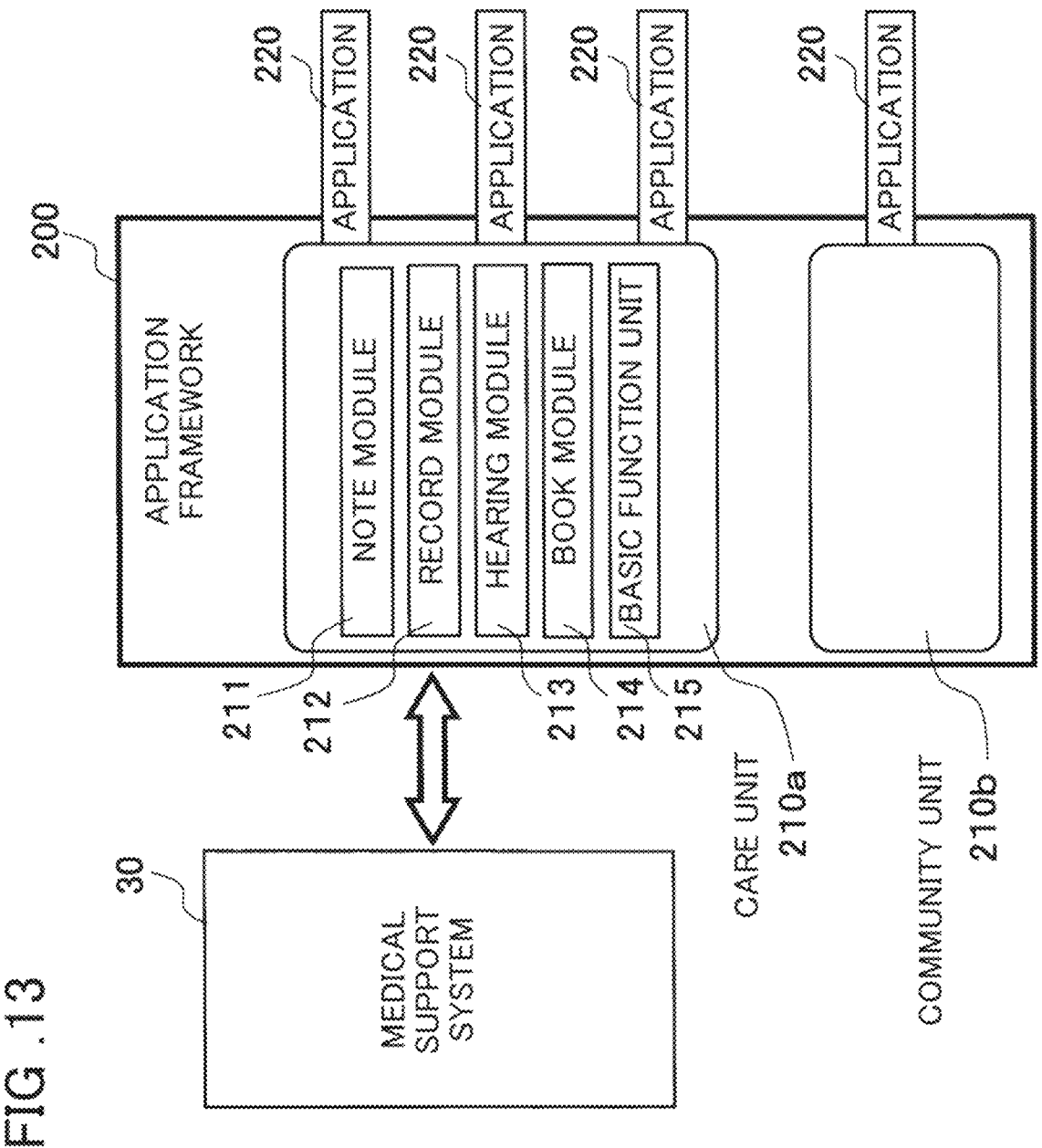

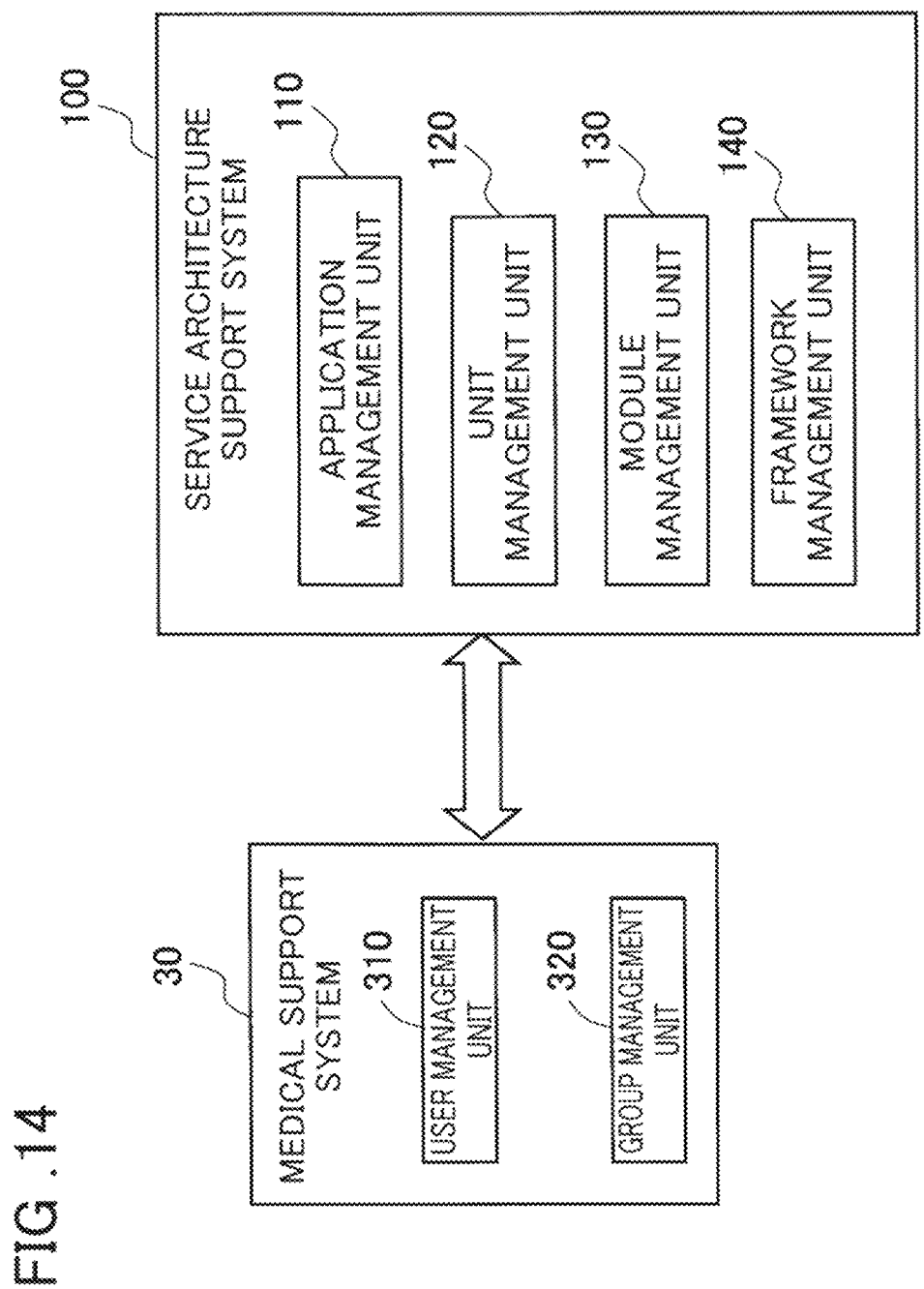

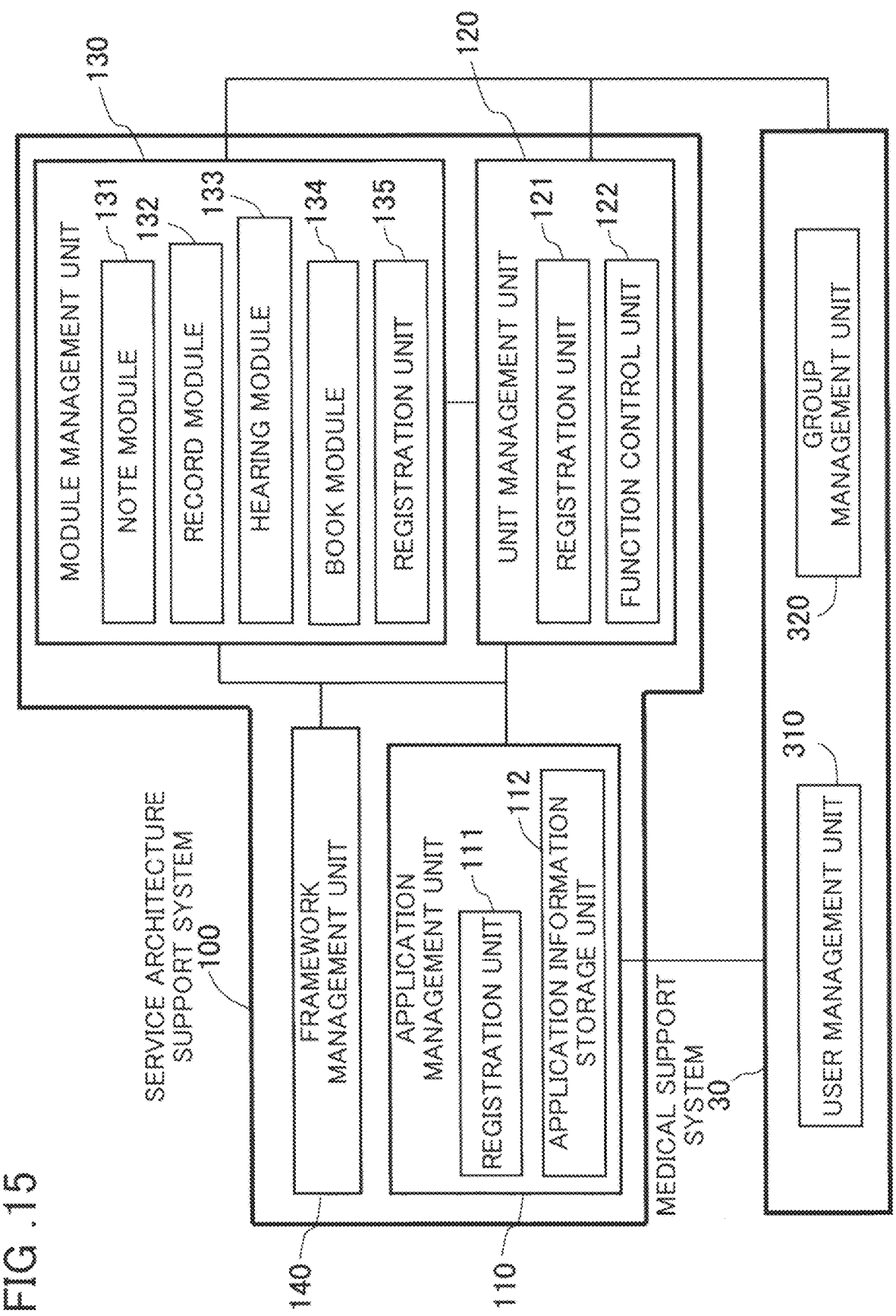

FIG. 16

(a) USER TABLE

| USER ID | LOGIN ID | PASSWORD | REGIST. DATE | STATUS |
|---|---|---|---|---|
| 100 | sumida@test.com | tKswU8yq | 2012/12/10 | ENABLED |
| 200 | ogura@test.com | fvXEd5Re | 2012/11/20 | ENABLED |
| 300 | yamada@test.com | acD1V5tp | 2012/12/25 | ENABLED |
| 500 | tanaka@abc.com | usCP81vm | 2017/9/30 | ENABLED |

(b) DEVELOPER TABLE

| USER ID | NAME | SEX | BIRTH DATE | MAIL ADDRESS | PROFESSION |
|---|---|---|---|---|---|
| 500 | ICHIRO TANAKA | MALE | 1985/12/10 | tanaka@abc.com | PROGRAMMER |

(c) DEVELOPER AFFILIATE ORGANIZATION TABLE

| GROUP ID | NAME | SECTION | REP. | ADDRESS | TEL | HP |
|---|---|---|---|---|---|---|
| 1000 | XYZ DEVELOPMENT CO., LTD. | SYSTEM DEVELOPMENT | ICHIRO TANAKA | MINATO-KU SHIBA | 03-2345-6789 | http://www.tanakasystem.jp |

(d) APPLICATION TABLE

| APPLICATION ID | TYPE | USER ID | GROUP ID | DATE | STATUS |
|---|---|---|---|---|---|
| 1 | | | 10003 | 2017/10/10 | ENABLED |
| 1 | | | 10004 | 2017/10/30 | ENABLED |
| 2 | | | 10003 | 2017/11/5 | ENABLED |
| 2 | | | 10005 | 2017/11/10 | ENABLED |

FIG. 23

APPLICATION MANAGEMENT SCREEN FOR SYSTEM MANAGER
(BASIC INFORMATION SETTINGS)

| LIST | APPLICATION INFORMATION | ACCESS ANALYSIS |
|---|---|---|

DIABETES MEDICATION SUPPORT    REGISTRATION DATE : 2017/10/30

| BASIC INFORMATION | MEDICINE(17) | ADDITIONAL FUNCTION(11) |
|---|---|---|

○ SET ICON IMAGE

CARE APPLICATION NAME

[ DIABETES MEDICATION SUPPORT ]

CATEGORY

[ MEDICATION ▼ ]   PRODUCTION

APPLICATION SETTINGS AUTHORITY
☑ MANAGER    ☑ KOYAMA    ☑ EXTERNAL STAFF

RECORD/REPLY AUTHORITY
☑ PATIENT    ☑ PATIENT FAMILY MEMBER/FRIEND    ☑ MEDICAL/CARE WORK

SUBSEQUENT CONSULTATION DAY(NOTIFICATION)

[ ONE DAY BEFORE - 12:00 ]

PROGRESS SUMMARY(NOTIFICATION)

[ SET ]

EXPLANATION OF APPLICATION

[ MEDICATION CONFIRMATION (1 WEEK);
FUNCTION ADDITION, INSPECTION RECORD; ENABLED ]

UTILIZATION RANGE SETTINGS
AVAILABLE TIMELINE    ☑ PATIENT GROUP: PATIENT SIDE ( RESET )  ( UPDATE )

FIG. 24

APPLICATION MANAGEMENT SCREEN FOR SYSTEM MANAGER (MEDICINE SETTINGS)

| LIST | APPLICATION INFORMATION | ACCESS ANALYSIS |
|---|---|---|

DIABETES MEDICATION SUPPORT    REGISTRATION DATE : 2017/10/30

| BASIC INFORMATION | MEDICINE(17) | ADDITIONAL FUNCTION(11) |
|---|---|---|

MEDICINE ALARM

☑ MEDICINE NOTIFICATION IS AUTOMATICALLY POSTED AT SET DATE AND TIME

MEDICINE CALENDAR

☑ SCHEDULE CONFIRMATION AND USAGE HISTORY CAN BE RECORDED IN CALENDAR ( RESET )  ( UPDATE )

SET MEDICINES                                                    [EDIT]

1. ● AAA TABLET 50 mg DOSING    [STOP]
2. ● BBB TABLET 2.5 mg DOSING    [STOP]
3. ▬ CCC TABLET 5 mg DOSING    [STOP]
4. ● DDD TABLET 50 mg DOSING    [STOP]
5. ▬ EEE TABLET 100 mg DOSING    [STOP]
6. ● FFF TABLET 12.5 mg DOSING    [STOP]
7. ▬ GGG TABLET 25 mg DOSING    [STOP]

FIG. 25

**APPLICATION MANAGEMENT SCREEN FOR SYSTEM MANAGER
(ADDITIONAL FUNCTION SETTINGS)**

| LIST | APPLICATION INFORMATION | ACCESS ANALYSIS |
|---|---|---|

DIABETES MEDICATION SUPPORT     REGISTRATION DATE : 2017/10/30

| BASIC INFORMATION | MEDICINE(17) | ADDITIONAL FUNCTION(11) |
|---|---|---|

SET FUNCTIONS

| # | | Function | |
|---|---|---|---|
| 1 | N | COMPLICATIONS, OTHER SYMPTOMS / NOTE | STOP |
| 2 | H | CONFIRMATION OF SYMPTOMS CAUSING ANXIETY / HEARING | STOP |
| 3 | H | CONFIRMATION OF EXERCISE HABITS / HEARING | STOP |
| 4 | H | CONFIRMATION OF EATING HABITS / HEARING | STOP |
| 5 | H | CONFIRMATION OF REMAINING MEDICINE / HEARING | STOP |
| 6 | B | DIABETES ADVICE (DIET) / BOOK | STOP |
| 7 | B | DIABETES ADVICE (EXERCISE) / BOOK | STOP |
| 8 | B | DIABETES ADVICE (KNOWLEDGE/RISK MANAGEMENT) / BOOK | STOP |
| 9 | H | CONFIRMATION OF INTERACTION / HEARING | STOP |
| 10 | B | MEDICATION CONFIRMATION (1 WEEK) / HEARING | STOP |
| 11 | R | INSPECTION RECORD / RECORD | STOP |

( RESET ) ( UPDATE )

FIG .26

APPLICATION MANAGEMENT SCREEN FOR SYSTEM MANAGER
(ADDITIONAL FUNCTION/QUESTION SETTINGS)

| LIST | APPLICATION INFORMATION | ACCESS ANALYSIS |

DIABETES MEDICATION SUPPORT     REGISTRATION DATE : 2017/10/30

| BASIC INFORMATION | MEDICINE(17) | ADDITIONAL FUNCTION(11) |

< RETURN     CONFIRMATION OF SYMPTOMS CAUSING ANXIETY (HEARING)

FUNCTION TITLE

CONFIRMATION OF SYMPTOMS CAUSING ANXIETY

NOTIFICATION SCHEDULE

EVERY SUNDAY 20:00

SUPPLEMENTARY EXPLANATION

HOW HAVE YOU FELT IN THE LAST WEEK? PLEASE TELL ME ABOUT YOUR PHYSICAL CONDITION. IF YOU START TO FEEL ANXIOUS OR HAVE ANXIETY, YOU CAN FILL IN EVEN TRIVIAL MATTERS. PATIENTS AND FAMILY MEMBERS CAN ANSWER.

RESET     UPDATE

REGISTER QUESTIONS

1 DO YOU HAVE ANY SYMPTOMS CAUSING ANXIETY?     STOP

2 PLEASE TELL ME ABOUT THE SYMPTOMS     STOP
  CAUSING YOU ANXIETY

FIG. 27

APPLICATION MANAGEMENT SCREEN FOR SYSTEM MANAGER
(ADDITIONAL FUNCTION/QUESTION SETTINGS)

| LIST | APPLICATION INFORMATION | ACCESS ANALYSIS |

DIABETES MEDICATION SUPPORT    REGISTRATION DATE: 2017/10/30

| BASIC INFORMATION | MEDICINE(17) | ADDITIONAL FUNCTION(11) |

< RETURN    CONFIRMATION OF SYMPTOMS CAUSING ANXIETY (HEARING)

ANSWER TYPE                    ANSWER RULE
[RADIO BUTTON(SINGLE ANSWER)]  ○ REQUIRED   ARBITRARY

QUESTION TITLE
[DO YOU HAVE ANY SYMPTOMS CAUSING ANXIETY?]

ANSWER ITEM

| 1 YES | NEXT ▼ | ▼ | STOP |
| 2 NO  | TRANSMIT ▼ | · · ▼ | STOP |

ADD ITEM OR ADD "OTHER"

ADDITIONAL MESSAGE & DISCLOSURE RANGE
M 1

[IF PATIENT HAS SYMPTOMS CAUSING ANXIETY, PLEASE CHECK PATIENT'S CONDITION, SYMPTOMS AND THEIR DEGREE.]

☑ MEDICAL/CARE WORK USER    ☐ GENERAL USER (PATIENT)    ☐ GENERAL USER (FAMILY MEMBER/FRIEND)

M 2

[                                                                    ]

☐ MEDICAL/CARE WORK USER    ☐ GENERAL USER (PATIENT)    ☐ GENERAL USER (FAMILY MEMBER/FRIEND)

APPLICATION MANAGEMENT SCREEN FOR SYSTEM MANAGER
(ADDITIONAL FUNCTION/QUESTION SETTINGS)

| LIST | APPLICATION INFORMATION | ACCESS ANALYSIS |

DIABETES MEDICATION SUPPORT    REGISTRATION DATE: 2017/10/30

| BASIC INFORMATION | MEDICINE(17) | ADDITIONAL FUNCTION(11) |

< RETURN    CONFIRMATION OF SYMPTOMS CAUSING ANXIETY (HEARING)

ANSWER TYPE                          ANSWER RULE
CHECK BOX(MULTIPLE ANSWERS)          ○ REQUIRED   ARBITRARY

QUESTION TITLE
DO YOU HAVE ANY SYMPTOMS CAUSING ANXIETY?

ANSWER ITEM

| 1 STOMACHACHE/BELLYACHE | TRANSMIT ▼ | M 1 ▼ | STOP |
| 2 STOMACH UPSET/HEARTBURN | TRANSMIT ▼ | M 1 ▼ | STOP |
| 3 ANOREXIA | TRANSMIT ▼ | M 1 ▼ | STOP |
| 4 NAUSEA/VOMITING | TRANSMIT ▼ | M 1 ▼ | STOP |
| 5 CONSTIPATION | TRANSMIT ▼ | M 1 ▼ | STOP |
| 6 DIARRHEA | TRANSMIT ▼ | M 1 ▼ | STOP |
| 7 HEADACHE | TRANSMIT ▼ | M 1 ▼ | STOP |
| 8 INSOMNIA | TRANSMIT ▼ | M 1 ▼ | STOP |
| 9 IRRITABLE | TRANSMIT ▼ | M 1 ▼ | STOP |

FIG. 29

APPLICATION MANAGEMENT SCREEN FOR SYSTEM MANAGER
(ADDITIONAL FUNCTION/PATIENT NOTE SETTINGS)

| LIST | APPLICATION INFORMATION | ACCESS ANALYSIS |

DIABETES MEDICATION SUPPORT    REGISTRATION DATE : 2017/10/30

| BASIC INFORMATION | MEDICINE(17) | ADDITIONAL FUNCTION(11) |

< RETURN    COMPLICATIONS, OTHER SYMPTOMS(NOTE)

NOTE TITLE
| PATIENT NOTE |

RECORDING ITEM

| 1  COMPLICATIONS | NEXT ▼ | STOP |
| 2  OTHER SYMPTOMS | NEXT ▼ | STOP |
| 3  INSPECTION VALUE 1 | NEXT ▼ | STOP |
| 4  INSPECTION VALUE 2 | NEXT ▼ | STOP |
| 5  INSPECTION VALUE 3 | NEXT ▼ | STOP |
| 6  INSPECTION VALUE 4 | NEXT ▼ | STOP |
| 7  ○○○ | NEXT ▼ | STOP |
| 8  ○○○ | NEXT ▼ | STOP |
| 9  ○○○ | NEXT ▼ | STOP |

FIG .31

APPLICATION MANAGEMENT SCREEN FOR SYSTEM MANAGER
(ADDITIONAL FUNCTION/INSPECTION RECORD ITEM SETTINGS)

| LIST | APPLICATION INFORMATION | ACCESS ANALYSIS |

DIABETES MEDICATION SUPPORT    REGISTRATION DATE: 2017/10/30

| BASIC INFORMATION | MEDICINE (17) | ADDITIONAL FUNCTION (11) |

< RETURN    INSPECTION RECORD (RECORD)

RECORD TITLE

INSPECTION RECORD

RECORDING ITEM

| 1 | HbA1c | NEXT ▼ | STOP |
| 2 | WEIGHT | NEXT ▼ | STOP |
| 3 | LDL CHOLESTEROL | NEXT ▼ | STOP |
| 4 | BLOOD SUGAR | NEXT ▼ | STOP |
| 5 | BLOOD PRESSURE | NEXT ▼ | STOP |
| 6 | OOO | NEXT ▼ | STOP |
| 7 | OOO | NEXT ▼ | STOP |
| 8 | OOO | NEXT ▼ | STOP |
| 9 | OOO | NEXT ▼ | STOP |

FIG .32

APPLICATION MANAGEMENT SCREEN FOR SYSTEM MANAGER
(POST ITEM/SETTINGS TIME, ETC. SETTINGSS)

< RETURN   DIABETES MEDICATION SUPPORT    [RESTART]

DIABETES MEDICATION SUPPORT    REGISTRATION DATE: 2017/10/30

| BASIC INFORMATION | MEDICINE (17) | ADDITIONALFUNCTION (11) |

NOTIFICATION OF NEW SETTINGSS

USAGE PERIOD                          SUBSEQUENT CONSULTATION DAY

| DECEMBER 1ST, 2017 - COMPLETION DATE (ARBITRARY) |   | NOT SET |

RECORD/REPLY AUTHORITY

☑ PATIENT       ☑ PATIENT FAMILY MEMBER/FRIEND      ☑ MEDICAL/CARE WORK

MEDICINE TO BE USED

● FFF TABLET 12.5 mg
  (1) DOSING IN MORNING

| WAKEUP | MORNING | NOON | EVENING | BEFORE SLEEP |
|---|---|---|---|---|
| — | ONE TABLET | — | — | — |
| — | 8:00 | — | — | — |

| INSPECTION VALUE |

INSPECTION RECORD
HbA1c (%), WEIGHT (kg), LDL CHOLESTEROL (mg/dL)

| PATIENT NOTE |

COMPLICATIONS, OTHER SYMPTOMS
DISCLOSURE RANGE: ALL MEMBERS

| NOTIFICATION SCHEDULE |

FIG .33

APPLICATION MANAGEMENT SCREEN FOR SYSTEM MANAGER
(POST ITEM/SETTINGS TIME, ETC. SETTINGSS)

< RETURN    DIABETES MEDICATION SUPPORT    RESTART

NOTIFICATION OF NEW SETTINGSS

COMPLICATIONS, OTHER SYMPTOMS

DISCLOSURE RANGE: ALL MEMBERS

| NOTIFICATION SCHEDULE |

SUBSEQUENT CONSULTATION DAY

| NOT SET |

PROGRESS SUMMARY

| NOT SET |

CONFIRMATION OF SYMPTOMS CAUSING ANXIETY

| EVERY MONDAY – 08:10 |

INSPECTION RECORD

| DAY BEFORE SUBSEQUENT CONSULTATION DAY – 09:05 |

CONFIRMATION OF REMAINING MEDICINE

| EVERY MONDAY – 08:30 |

OOOO
| OOOOOOO |

OOOO
| OOOOOOO |

FIG. 34

APPLICATION MANAGEMENT SCREEN FOR SYSTEM MANAGER
(INSPECTION VALUE SETTINGSS)

< RETURN  INSPECTION VALUE SETTINGSS  [SETTINGSS]

HbA1c (%)

| INITIAL VALUE | TARGET VALUE |
|---|---|
| 8.5 | 6.5 |
| REFERENCE VALUE UPPER LIMIT | REFERENCE VALUE LOWER LIMIT |
|  |  |

☐ ALSO ALERT PATIENT

WEIGHT (kg)

| INITIAL VALUE | TARGET VALUE |
|---|---|
| 75.0 | 70.0 |
| REFERENCE VALUE UPPER LIMIT | REFERENCE VALUE LOWER LIMIT |
|  |  |

☐ ALSO ALERT PATIENT

LDL CHOLESTEROL (mg/dL)

| INITIAL VALUE | TARGET VALUE |
|---|---|
| 170 | 150 |
| REFERENCE VALUE UPPER LIMIT | REFERENCE VALUE LOWER LIMIT |
|  |  |

☐ ALSO ALERT PATIENT

FIG .35

APPLICATION MANAGEMENT SCREEN FOR SYSTEM MANAGER
(START DATE SETTINGSS)

| START DATE SETTINGSS | | | | | | CLOSE |
|---|---|---|---|---|---|---|
| NOVEMBER 2017 | | | | | | |
| SUNDAY | MONDAY | TUESDAY | WEDNESDAY | THURSDAY | FRIDAY | SATURDAY |
|  |  |  | 1 | 2 | 3 | 4 |
| 5 | 6 | 7 | 8 | 9 | 10 | 11 |
| 12 | 13 | 14 | 15 | 16 | 17 | 18 |
| 19 | 20 | 21 | 22 | 23 | 24 | 25 |
| 26 | 27 | 28 | 29 | 30 |  |  |
| DECEMBER 2017 | | | | | | |
| SUNDAY | MONDAY | TUESDAY | WEDNESDAY | THURSDAY | FRIDAY | SATURDAY |
|  |  |  |  |  | 1 | 2 |
| 3 | 4 | 5 | 6 | 7 | 8 | 9 |
| 10 | 11 | 12 | 13 | 14 | 15 | 16 |
| 17 | 18 | 19 | 20 | 21 | 22 | 23 |
| 24 | 25 | 26 | 27 | 28 | 29 | 30 |
| 31 |  |  |  |  |  |  |
| JANUARY 2018 | | | | | | |
| SUNDAY | MONDAY | TUESDAY | WEDNESDAY | THURSDAY | FRIDAY | SATURDAY |
|  | 1 | 2 | 3 | 4 | 5 | 6 |
| 7 | 8 | 9 | 10 | 11 | 12 | 13 |
| 14 | 15 | 16 | 17 | 18 | 19 | 20 |
| 21 | 22 | 23 | 24 | 25 | 26 | 27 |
| 28 | 29 | 30 | 31 |  |  |  |

FIG .42

ANSWER SCREEN DISPLAYED
ON TIMELINE (PATIENT SIDE) OF GROUP

COMPLICATIONS, OTHER SYMPTOMS

IF YOU HAVE ANY COMPLICATIONS OR
OTHER SYMPTOMS, PLEASE TELL ME.

○ NO

○ I HAVE THE FOLLOWING SYMPTOMS.

MESSAGE INPUT FIELD

REPLY

FIG. 44

ANSWER CHOICE SCREEN DISPLAYED
ON TIMELINE (PATIENT SIDE) OF GROUP

CONFIRMATION OF EATING HABITS

DO YOU HAVE THREE MEALS IN THE MORNING,
NOON AND NIGHT AT FIXED TIMES?

○ YES
○ YES, BUT IRREGULARLY
○ SOMETIMES SKIP MEALS
○ OFTEN SKIP MEALS

[TRANSMIT]

SERVICE ARCHITECTURE SUPPORT METHOD AND SYSTEM FOR MEDICAL/NURSING SUPPORT SYSTEM

TECHNICAL FIELD

The present invention relates to a service architecture support method and a service architecture support system in a medical/care support system, and more specifically relates to a support method in which, in a medical/care support system that allows medical/care information related to a specific patient or a specific care recipient to be browsed according to a request from a user terminal through a communication network by use of the user terminal so as to support the provision of a medical/care service to the patient or the care recipient, an application program (hereinafter also referred to as an "application" or "app") that is operated on the system is incorporated so as to construct and provide a new service to the medical/care service provided by the system, and to a system which carries out such a method.

BACKGROUND ART

The present applicant files a patent application on a medical/care support system in which a group is generated for each target person of a medical/care service (that is, a patient or a care recipient) and in which medical/care information related to the target person can be shared among group members in the group (see Patent Document 1). This medical/care support system has features and advantages in which one or a plurality of users of a medical/care service (including not only the patient or the care recipient, but also a medical worker or a care worker) are selectively made to belong, as group members, to a group generated for each target person of the medical/care service (that is, the patient or the care recipient), in which only the group members are allowed to browse medical/care information on the target person related to the group and in which thus the medical/care information related to the target person can be shared among the group members while ensuring the privacy of the target person. In this medical/care support system, the browsing and the input and output of medical information and care information on each patient or each care recipient, the transmission and reception of messages, and the like can be executed through a communication network with a user terminal, and thus it is possible to provide support so that medical workers and care workers of a large number of professions, such as doctors and nurses with different specialties, nutritionists, care managers and helpers cooperate with each other to provide higher quality medical and care services.

Here, the "medical/care information" described above means all medical or care information on each target person serving as a target person of a medical/care service, that is, a patient or a care recipient.

An application framework has been known for a long time which is provided in order to facilitate the development of an application that is operated on a specific platform. For example, Patent Document 2 discloses a system which produces a mobile application framework for brand expansion. This system includes: an interface for a network; a resource which organizes branding contents provided from a developer so as to produce the mobile application framework; and an application for accessing the mobile application framework by at least one user from at least one mobile device, the mobile application framework including: a navigation menu for accessing a plurality of previously defined categories of branding functions; and a sub-menu which provides access to individual functions within the previously defined categories, and the previously defined categories are assigned for brand expansion corresponding to target industrial sections (see Claim 1, Paragraphs [0014] to [0025] and FIGS. 1 to 6).

Furthermore, Patent Document 3 discloses a network-based platform system devised such that a program code for executing a specific function in an application (game) for smartphones is previously produced and is provided to a developer and that thus it is possible to easily develop the application for smartphones and to reduce a development period. This platform system includes: an application framework for smartphones; a framework providing server which provides the recognition code of a specific-function UI (user interface) screen that needs to be installed in the application for smartphones developed based on the application framework; a store server which distributes the application; and a client terminal which receives the application framework for smartphones from the framework providing server, which generates the application for smartphones according to a key input of the developer, which installs, in the application, the specific function embodied in the application framework and which registers the application in the store server by a key input of the developer (see Claims 1, 4, 5 and 10, Paragraphs [0028] to [0061] and FIGS. 1 to 3).

Patent Document 1: Japanese Unexamined Patent Application, Publication No. 2015-15010
Patent Document 2: Japanese Unexamined Patent Application (Translation of PCT Application), Publication No. 2013-521546
Patent Document 3: Japanese Unexamined Patent Application, Publication No. 2013-143125

DISCLOSURE OF THE INVENTION

Problems to be Solved by the Invention

However, it was found that there is a need with which the medical/care support system of Patent Document 1 described above needs to cope. Specifically, although in recent years, in medical and care sites, a larger number of new services (hereinafter these services may also be referred to as "additional services"), such as a medication management service and treatment support services for diseases such as diabetes which are desired to be provided to a patient, a care recipient and a medical worker (that is, users of existing services) have been proposed for medical/care services (hereinafter these services may also be referred to as "existing services") provided by the system, it is not easy to provide such additional services to the users of the existing services.

More specifically, when these types of additional services (new services) are added to the existing radical/care services provided by the medical/care support system of Patent Document 1, though functions for realizing the additional services need to be added to the medical/care support system, since a large number of types of additional services are desired to be added and needs for these types of additional services are expected to continuously occur in the future, a new development operation needs to be performed each time an additional service is added, with the result that the development cost is significantly increased. Hence, this method is not realistic. Therefore, it can be considered that an application which is operated on this medical/care support system is developed as necessary by an external company or the like, that such an application is incorporated in the medical/care support system of Patent Document 1, and that thus it is possible to provide the additional services sequentially and additionally.

However, since in the medical/care service provided by the medical/care support system of Patent Document 1, a group is generated for each target person of the medical/care service (that is, a patient or a care recipient), and since medical/care information related to the target person can be shared among group members in the group while ensuring the privacy of the target, person, the application which provides an additional service that is added to the medical/care service (existing service) needs to effectively utilize the features and advantages of the system described above. When it is considered that the application which effectively utilizes the features and advantages of the system will be developed by an external company, it is also necessary to prepare an environment in which the application can be developed as easily as possible.

In order to satisfy the needs related to the application development environment, the idea to provide the application frameworks disclosed in Patent Documents 2 and 3 is beneficial. However, the purpose and the target platform of the application frameworks disclosed in Patent Documents 2 and 3 are significantly different from those of the medical/care support system of Patent Document 1, and thus it is difficult to directly utilize the idea of the application frameworks disclosed in Patent Documents 2 and 3 for the medical/care support system of Patent Document 1.

The present invention is made in view of the conditions described above, and an object thereof is to provide a service architecture support method and a service architecture support system in a medical/care, support system where in a medical/care support system having features "in which one or a plurality of users of a medical/care service (including not only a patient or a care recipient, but also a medical worker or a care worker) are selectively made to belong to a group generated for each target person of the medical/care service (that is, the patient or the care recipient), in which only the group members are allowed to browse medical/care information on the target person related to the group and in which thus the medical/care information related to the target person can be shared among the group members while ensuring the privacy of the target person", an application program is incorporated as necessary so as to be able to easily add various new services to the medical/care service provided by the system.

Another object of the present invention is to provide a service architecture support method and a service architecture support system in a medical/care support system in which an application program that is operated on the medical/care support system and that can effectively utilize the features of the system, can be efficiently developed, and in which moreover, the details of a new service provided by the application program after being incorporated into the medical/care support system can be finely adjusted according to the needs of a patient or a care recipient serving as a target person of a medical/care service or a medical worker or a care worker for providing a medical/care service.

Yet another object of the present invention is to provide a service architecture support; method and a service architecture support system in a medical/care support system in which group members in a group generated for each target person of a medical/care service (a patient or a care recipient) can dynamically adjust, according to their needs, the start or stop of utilization of one or a plurality of new services provided by one or a plurality of application programs.

Still another object of the present invention is to provide a service architecture support method and a service architecture support system in a medical/care support system in which when group members in a group generated for each target person of a medical/care service (a patient or a care recipient) selectively utilize, according to their needs, a plurality of new services provided by one or a plurality of application programs, it is not necessary to repeat an operation of logging in to and logging out of the medical/care support system.

Still yet another object of the present invention is to provide a service architecture support method and a service architecture support system in a medical/care support system in which one or a plurality of new services provided by one or a plurality of application programs are added to existing medical/care services so as to provide a synergistic effect, and in which consequently, it is possible to expect an enhanced effect as compared with a case where one or a plurality of new services and existing medical/care services are separately provided.

Yet other objects of the present invention which are not described here will be obvious from the following description and accompanying drawings.

Means for Solving the Problems (1) According to a first aspect of the present invention, a service architecture support method in a medical/care support system is provided. This method is a method of supporting the construction of a new service in a medical/care support system that allows medical/care information related to a patient or a care recipient to be browsed according to a request from a user terminal through a communication network with the user terminal so as to support the provision of a medical/care service to the patient or the care recipient, user identification information (for example, a user ID) is assigned to a user who utilizes the medical/care service through the user terminal and is stored, service recipient identification information (for example, a patient ID) is assigned to the patient or the care recipient serving as the user, and is stored so as to be associated with the user identification information, business worker identification information (for example, a medical worker ID) is assigned to a medical worker or a care worker serving as the user, and is stored so as to be associated with the user identification information, a group which has unique group identification information (for example, a group ID) is generated according to an instruction from the user terminal so as to be associated with the service recipient identification information, one or a plurality of the users are selectively made to belong to the group as group members according to an instruction from the user terminal such that the medical/care information of the patient or the care recipient corresponding to the service recipient identification information related to the group can be shared among the group members through the user terminal, an application framework which provides one or a plurality of specific functions is provided on the medical/care support system such that an application program for providing the new service can be developed from a developer terminal by utilization of the application framework, when the application program which is developed by the utilization of the application framework and in which one or a plurality of the specific functions are installed is incorporated into the medical/care support system, unique application identification information (for example, an application ID) is assigned to the application program, and the application identification information is stored so as to be associated with one or a plurality of pieces of the group identification information such that only the group members who belong to one or a plurality of the groups having one or a plurality of pieces of the group identification information associated with the application identification information are allowed to utilize, through the user terminal, one or a plurality of the new services provided by the application program, in the application program, a predetermined manager executes a predetermined manager settings such that one or a plurality of the specific functions installed in the application program can be utilized on the medical/care support system, and in the manager settings, one or a plurality of the specific functions are set according to a need of the patient or the care recipient related to one or a plurality of the groups associated with the application identification information of the application program or the medical worker or the care worker related to the groups and the group members belonging to each of the groups provide, as necessary, an instruction on the user terminal so as to be able to selectively utilize a plurality of the new services provided by a plurality of the application programs having a plurality of pieces of the application identification information associated with the group identification information of the group.

In the service architecture support method in the medical/care support system according to the first aspect of the present invention, on the medical/care support system, the application framework for providing one or a plurality of the specific functions is provided, and thus one or a plurality of the application programs for providing one or a plurality of the new services can be developed by utilization of the application framework. When the application program which is developed by the utilization of the application framework and in which one or a plurality of the specific functions are installed is incorporated into the medical/care support system, the application identification information is assigned to the application program, and the application identification information is stored so as to be associated with one or a plurality of pieces of the group identification information such that only the group members who belong to one or a plurality of the groups having one or a plurality of pieces of the group identification information associated with the application identification information are allowed to utilize, through the user terminal, one or a plurality of the new services provided by the application program. Hence, one or a plurality of the applications are incorporated into the medical/care support system, and thus various new services can easily be added to the medical/care services provided by the system.

When the application program which is developed by the utilization of the application framework and in which one or a plurality of the specific functions are installed is incorporated into the medical/care support system, the application identification information is assigned to the application program, and the application identification information is stored so as to be associated with one or a plurality of pieces of the group identification information such that only the group members who belong to one or a plurality of the groups having one or a plurality of pieces of the group identification information associated with the application identification information are allowed to utilize, through the user terminal, one or a plurality of the new services provided by the application program. It is possible to effectively utilize the features of the medical/care support system "in which one or a plurality of users of a medical/care service (including not only a patient or a care recipient but also a medical worker or a care worker) are selectively made to belong to a group generated for each target person of the medical/care service (that is, the patient or the care recipient), in which only the group members are allowed to browse radical/care information on the target person related to the group and in which thus the medical/care information related to the target person can be shared among the group members while ensuring the privacy of the target person".

Furthermore, since the application framework is provided on the medical support system, and thus one or a plurality of the applications can be developed by utilization of the application framework, it is possible to efficiently develop the application program which is operated on the medical/care support system and which can effectively utilize the feature of the system. Moreover, in the application program, the manager executes the manager settings such that one or a plurality of the specific functions installed in the application program can be utilized on the medical/care support system and in the manager settings, the details (practice conditions) of one or a plurality of the specific functions are set according to the need of the patient or care recipient related to one or a plurality of the groups associated with the application identification information of the application program or the medical worker or the care worker related to the group, with the result that it is possible to finely adjust the details of the new service provided by the application program after being incorporated into the medical/care support system according to the need of the patient or the care recipient serving as the target person of the medical/care service or the medical worker or the care worker who provides the medical/care service.

Furthermore, when the application program is incorporated into the medical/care support system, the application identification information is assigned to the application program, and the application identification information is stored so as to be associated with one or a plurality of pieces of the group identification information such that only the group members who belong to one or a plurality of the groups having one or a plurality of pieces of the group identification information associated with the application identification information are allowed to utilize, through the user terminal, one or a plurality of the new services provided by the application program. Hence, the group members in the group generated for each target person of the medical/care service (that is, the patient or the care recipient) can dynamically adjust, according to their needs, the start or stop of utilization of one or a plurality of the new services provided by one or a plurality of the application programs.

Furthermore, since the group members belonging to each of the groups provide, as necessary, an instruction on the user terminal so as to be able to selectively utilize a plurality of the new services provided by a plurality of the application programs having a plurality of pieces of the application identification information associated with the group identification information of the group, when the group members in the group generated for each target person of the medical/care service (the patient or the care recipient) selectively utilize, according to their needs, a plurality of the new services provided by one or a plurality of the application programs, it is not necessary to repeat an operation of logging in to and logging out of the medical/care support system.

Furthermore, one or a plurality of the new services provided by the application program is utilized, and thus it is possible to browse information (application-related information) provided by the group members related to one or a plurality of the groups associated with the application identification information of the application program together with the medical/care information on the patient or the care recipient related to one or a plurality of the groups, with the result that information which is not noticed when the application-related information and the medical/care information are separately present is often noticed. In other words, one or a plurality of the new services provided by one or a plurality of the application programs are added to existing medical/care services, and thus a synergistic effect is often provided. Consequently, it is possible to expect an enhanced effect as compared with a case where one or a plurality of the new services and the existing medical/care services are separately provided.

(2) In a preferred example of the service architecture support method in the medical/cure support system according to the first aspect of the present invention, a necessary user settings is executed in addition to the manager settings such that the application program can be utilized on the medical/care support system, and the user settings is executed by any one of the users related to one or a plurality of the groups associated with the application identification information of the application program.

(3) In another preferred example of the service architecture support method in the medical/care support system according to the first aspect of the present invention, the application program describes a combination of one or a plurality of the specific functions needed to achieve a purpose of the application program and which is provided by the application framework.

(4) In yet another preferred example of the service architecture support method in the medical/care support system according to the first aspect of the present invention, one or a plurality of the application programs associated with each of the groups sequentially display, on the user terminal, according to a predetermined schedule, service element information necessary for the new service provided by the application program on a timeline in which the medical/care information of the patient or the care recipient related to the group can be browsed, and when it is necessary to reply to the service element information, reply information is displayed from the user terminal on the timeline or is transmitted to the medical/care support system so as to reply to the service element, information.

The "service element information" described above may include one or a plurality of pieces of question information or presentation information relating to the group members in the group. Here, "question information" refers to information which includes some kind of question, and "presentation information" refers to information which includes only information that presents some kind of message (which does not include any question). The "reply information" described above refers to information which is generated as a reply to the service element information (for example, the question information).

(5) In still another preferred example of the service architecture support method in the medical/care support system according to the first aspect of the present invention, the application framework includes, as a section which realizes one or a plurality of the specific functions, a first module which provides a function of storing predetermined as-needed information, a second module which provides a function of collecting and storing predetermined external information, a third module which provides a question-and-answer function and a fourth module which provides a function of storing content information (a note module, a record module, a hearing module and a book module).

(6) In still yet another preferred example of the service architecture support method in the medical/care support system according to the first aspect of the present invention, the application framework Includes a plurality of units whose purposes are different from each other, and one or a plurality of the specific functions are provided in each of the plurality of units.

(7) According to a second aspect of the present invention, a service architecture support system in a medical/care support system is provided. The system is a system for supporting the construction of a new service in a medical/care support system that allows medical/care information related to a patient or a care recipient to be browsed according to a request from a user terminal through a communication network with the user terminal so as to support the provision of a medical/care service to the patient or the care recipient, the system including: a user identification information storage section (for example, a user information storage unit) which assigns user identification information (for example, a user ID) to a user who utilizes the medical/care service through the user terminal and stores it; a service recipient identification information storage section (for example, a patient information storage unit) which assigns service recipient identification information (for example, a patient ID) to the patient or the care recipient serving as the user, and which stores the service recipient identification information such that the service recipient identification information is associated with the user identification information; a business worker identification information storage section (for example, a medical worker information storage unit) which assigns business worker identification information (for example, a medical worker ID) to a medical worker or a care worker serving as the user, and which stores the business worker identification information such that the business worker identification information is associated with the user identification information; a group management section (for example, a group management unit) that generates, according to an instruction from the user terminal, a group which has unique group identification information (for example, a group ID) such that the group is associated with the service recipient identification information; a group member selection section (for example, the group management unit) which selectively makes one or a plurality of the users belong to the group as group members according to an instruction from the user terminal such that the medical/care information of the patient or the care recipient corresponding to the service recipient identification information related to the group can be shared among the group members through the user terminal; a framework management section (for example, a framework management unit) that provides an application framework which provides one or a plurality of specific functions on the medical/care support system such that an application program for providing the new service can be developed from a developer terminal by utilization of the application framework; and an application management section (for example, an application management unit) where when the application program which is developed by the utilization of the application framework and in which one or a plurality of the specific functions are installed is incorporated into the medical/care support system, unique application identification information (for example, an application ID) is assigned to the application program, and where the application identification information is stored so as to be associated with one or a plurality of pieces of the group identification information such that only the group members who belong to one or a plurality of the groups having one or a plurality of pieces of the group identification information associated with the application identification information are allowed to utilize, through the user terminal, one or a plurality of the new services provided by the application program, in the application program, a predetermined manager executes a predetermined manager settings such that one or a plurality of the specific functions installed in the application program can be utilized on the medical/care support system, and in the manager settings, one or a plurality of the specific functions are set according to a need of the patient or the care recipient related to one or a plurality of the groups associated with the application identification information of the application program or the medical worker or the care worker related to the groups and the group members belonging to each of the groups provide, as necessary, an instruction on the user terminal so as to be able to selectively utilize a plurality of the new services provided by a plurality of the application programs having a plurality of pieces of the application identification information associated with the group identification information of the group.

In the service architecture support system in the medical/care support system according to the second aspect of the present invention, by the framework management section, on the medical/care support system, the application framework for providing one or a plurality of the specific functions is provided, and thus one or a plurality of the application programs for providing one or a plurality of the new services can be developed by utilization of the application framework. When the application program which is developed by the utilization of the application framework and in which one or a plurality of the specific functions are installed is incorporated into the medical/care support system, the application identification information is assigned to the application program, and the application identification information is stored so as to be associated with one or a plurality of pieces of the group identification information such that only the group members who belong to one or a plurality of the groups having one or a plurality of pieces of the group identification information associated with the application identification information are allowed to utilize, through the user terminal, one or a plurality of the new services provided by the application program. Hence, one or a plurality of the applications are incorporated into the medical/care support system, and thus various new services can easily be added to the medical/care services provided by the system.

When the application program which is developed by the utilization of the application framework and in which one or a plurality of the specific functions are installed is incorporated into the medical/care support system, by the application management section, the application identification information is assigned to the application program, and the application identification information is stored so as to be associated with one or a plurality of pieces of the group identification information such that only the group members who belong to one or a plurality of the groups having one or a plurality of pieces of the group identification information associated with the application identification information are allowed to utilize, through the user terminal, one or a plurality of the new services provided by the application program. It is possible to effectively utilize the features of the medical/care support system "in which one or a plurality of users of a medical/care service (including not only a patient or a care recipient, but also a medical worker or a care worker) are selectively made to belong to a group generated for each target person of the medical/care service (that is, the patient or the care recipient), in which only the group members are allowed to browse medical/care information on the target person related to the group and in which thus the medical/care information related to the target person can be shared among the group members while ensuring the privacy of the target person".

Furthermore, since the application framework is provided on the medical support system, and thus one or a plurality of the applications can be developed by utilization of the application framework, it is possible to efficiently develop the application program which is operated on the medical/care support system and which can effectively utilize the feature of the system. Moreover, in the application program, the manager executes the manager settings such that one or a plurality of the specific functions installed in the application program can be utilized on the medical/care support system and in the manager settings, the details (practice conditions) of one or a plurality of the specific functions are set according to the need of the patient or care recipient related to one or a plurality of the groups associated with the application identification information of the application program or the medical worker or the care worker related to the group, with the result that it is possible to finely adjust the details of the new service provided by the application program after being incorporated into the medical/care support system according to the need of the patient or the care recipient serving as the target person of the medical/care service or the medical worker or the care worker who provides the medical/care service.

Furthermore, when the application program is incorporated into the medical/care support system, by the application management section, the application identification information is assigned to the application program, and the application identification information is stored so as to be associated with one or a plurality of pieces of the group identification information such that only the group members who belong to one or a plurality of the groups having one or a plurality of pieces of the group identification information associated with the application identification information are allowed to utilize, through the user terminal, one or a plurality of the new services provided by the application program. Hence, the group members in the group generated for each target person of the medical/care service (that is, the patient or the care recipient) can dynamically adjust, according to their needs, the start or stop of utilization of one or a plurality of the new services provided by one or a plurality of the application programs.

Furthermore, since the group members belonging to each of the groups provide, as necessary, an instruction on the user terminal so as to be able to selectively utilize a plurality of the new services provided by a plurality of the application programs having a plurality of pieces of the application identification information associated with the group identification information of the group, when the group members in the group generated for each target person of the medical/care service (the patient or the care recipient) selectively utilize, according to their needs, a plurality of the new services provided by one or a plurality of the application programs, it is not necessary to repeat an operation of logging in to and logging out of the medical/care support system.

Furthermore, one or a plurality of the new services provided by the application program is utilized, and thus it is possible to browse information (application-related information) provided by the group members related to one or a plurality of the groups associated with the application identification information of the application program together with the medical/care information on the patient or the care recipient related to one or a plurality of the groups, with the result that, information which is not noticed when the application-related information and the medical/care information are separately present is often noticed. In other words, one or a plurality of the new services provided by one or a plurality of the application programs are added to existing medical/care services, and thus a synergistic effect is often provided. Consequently, it is possible to expect an enhanced effect as compared with a case where one or a plurality of the new services and the existing medical/care services are separately provided.

(8) In a preferred example of the service architecture support system in the medical/care support system according to the second aspect of the present invention, a necessary user settings is executed in addition to the manager settings such that the application program can be utilized on the medical/care support system, and the user settings is executed by any one of the users related to one or a plurality of the groups associated with the application identification information of the application program.

(9) In another preferred example of the service architecture support system in the medical/care support system according to the second aspect of the present invention, the application program describes a combination of one or a plurality of the specific functions needed to achieve a purpose of the application program and which is provided by the application framework.

(10) In still yet another preferred example of the service architecture support system in the medical/care support system according to the first aspect of the present invention, one or a plurality of the application programs associated with each of the groups sequentially display, on the user terminal, according to a predetermined schedule, service element information necessary for the new service provided by the application program on a timeline in which the medical/care information of the patient or the care recipient related to the group can be browsed, and when it is necessary to reply to the service element information, reply information is displayed from the user terminal on the timeline or is transmitted to the medical/care support system so as to reply to the service element information.

The "service element information" described above may include one or a plurality of pieces of question information or presentation information relating to the group members of the group. Here, "question information" refers to information which includes some kind of question, and "presentation information" refers to information which includes only information that presents some kind of message (which does not include any question). The "reply information" described above refers to information which is generated as a reply to the service element information (for example, the question information).

(11) In still yet another preferred example of the service architecture support system in the medical/care support system according to the first aspect of the present invention, the application framework includes, as a section which realizes one or a plurality of the specific functions, a first module which provides a function of storing predetermined as-needed information, a second module which provides a function of collecting and storing predetermined external information, a third module which provides a question-and-answer function and a fourth module which provides a function of storing content information (a note module, a record module, a hearing module and a book module).

(12) In still yet another preferred example of the service architecture support system in the medical/care support system according to the first aspect of the present invention, the application framework includes a plurality of units whose purposes are different from each other, and one or a plurality of the specific functions are provided in each of the plurality of units.

(13) In the present invention, the "service element information" described above means element information necessary for forming the new service provided by the application, and is, for example, the question information and the presentation information which are displayed on the timeline in order to provide (realize) the new service. For example, various types of posted messages described in FIGS. 37 to 41, which will be described later, apply thereto.

The "reply information" described above means information which is displayed or transmitted as a reply to the "service element information" in order to form the new service provided by the "service element information", and is, for example, information which is displayed as a reply on the timeline in order to provide (realize) the new service or information which is transmitted as a reply to the medical/care support system. For example, various types of reply messages described in FIGS. 42 to 45 and various types of reply messages described in FIGS. 46 and 47, which will be described later, apply thereto.

The "application framework" described above means software that is configured so as to include at least functional block groups each of which provides one or a plurality of specific functions and so as to be able to develop the desired application program which is operated on the medical/care support system by utilization of at least one of the functional block groups.

The "application program (application)" described above means a program in which at least one of the functional block groups provided by the application framework is installed and which is operated on the medical/care support system so as to additionally provide some kind of new service to the medical/care service provided by the system.

The "new service" described above means a service which is provided by the application program and which is added to the medical/care service provided by the medical/care support system. Examples of the new service related to the medical field include: (a) medical services associated with various types of care (treatment), such as medication management, lifestyle improvement, diabetes medication support, team medical support, pressure ulcer care and rehabilitation support; and (b) medical services associated with community production/operation such as various types of coordination, consultation reception, advice and information provision which function as cooperation windows between multi-professional workers. Examples of the new service related to the care field include: (c) care services associated with various types of care, such as home-visit care, home-visit nursing, home rehabilitation support, home bathing support, dementia support, and the like.

The "application-related information" described above means information which is provided, by utilization of the new service provided by the application program, to the group members related to one or a plurality of groups associated with the application identification information of the application program.

Effects of the Invention

In the service architecture support method in the medical/care support system according to the first aspect of the present invention and the service architecture support system in the medical/care support system according to the second aspect thereof, effects (a) to (e) below are obtained.

(a) An application program is incorporated as necessary into a medical/care support system having features "in which one or a plurality of users of a medical/care service (including not only a patient or a care recipient, but also a medical worker or a care worker) are selectively made to belong to a group generated for each target person of the medical/care service (that is, the patient or the care recipient), in which only the group members are allowed to browse medical/care information on the target person related to the group and in which thus the medical/care information related to the target person can be shared among the group members while ensuring the privacy of the target person", with the result that it is possible to easily add various new services to the medical/care service provided by the system.

(b) An application program that is operated on the medical/care support system and that can effectively utilize the features of the system can be efficiently developed, and moreover, the details of a new service provided by the application program after being incorporated into the medical/care support system can be finely adjusted according to the needs of a patient or a care recipient serving as a target person of a medical/care service or a medical worker or a care worker for providing a medical/care service.

(c) Group members in a group generated for each target, person of a medical/care service (that is, a patient or a care recipient) can dynamically adjust, according to their needs, the start or stop of utilization of one or a plurality of new services provided by one or a plurality of application programs.

(d) When group members in a group generated for each target person of a medical/care service (that is, a patient or a care recipient) selectively utilize, according to their needs, a plurality of new services provided by one or a plurality of application programs, it is not necessary to repeat an operation of logging in to and logging out of the medical/care support system.

(e) One or a plurality of new services provided by one or a plurality of application programs are added to existing medical/care services so as to provide a synergistic effect, and consequently, it is possible to expect an enhanced effect as compared with a case where one or a plurality of new services and existing medical/care services are separately provided.

BRIEF DESCRIPTION OF THE DRAWINGS

FIG. 4 is a diagram showing configuration examples of tables used in the medical support system shown in FIG. 1 in which (a) is a user table, (b) is a patient table, (c) is a medical worker table and (d) is a medical-related facility table;

FIG. 5 is a diagram showing configuration examples of the tables used in the medical support system shown in FIG. 1 in which (a) is a medical-related facility patient table, (b) is a disease table, (c) is a group table and (d) is a group participation table;

FIG. 6 is a diagram showing configuration examples of the tables used in the medical support system shown in FIG. 1 in which (a) is an invitation request table, (b) is a timeline table, (c) is a medical information sharing rule table and (d) is an NFC terminal management role table;

FIG. 7 is a diagram showing configuration examples of the tables used in the medical, support system shown in FIG. 1 in which (a) is a message transmission reservation table and (b) is a patient attribute table;

FIG. 13 is a conceptual diagram showing a relationship between the medical support system shown in FIG. 1, the application framework generated with the service architecture support system according to the embodiment of the present invention and the applications;

FIG. 14 is a functional block diagram schematically showing internal structures of the medical support system shown in FIG. 1 and the service architecture support system according to the embodiment of the present invention;

FIG. 15 is a functional block diagram showing the details of the internal structure of the service architecture support system according to the embodiment of the present invention;

FIG. 16(a) is a diagram showing a configuration example of the user table used in the medical support system shown in FIG. 1, FIG. 16(b) is a diagram showing a configuration example of a developer table used in the service architecture support system according to the embodiment of the present invention.

FIG. 16(c) is a diagram showing a configuration example of a developer-affiliate organization table used in the service architecture support system and FIG. 16(d) is a diagram showing a configuration example of an application table used in the service architecture support system;

FIG. 23 is an illustrative view showing an example of an "application management screen for system manager (basic information settings)" when the application is installed into the medical support system in which the service architecture support system according to the embodiment of the present invention is incorporated;

FIG. 24 is an illustrative view showing an example of an "application management screen for system manager (medicine settings)" when the application is installed into the medical support system in which the service architecture support system according to the embodiment of the present invention is incorporated;

FIG. 25 is an illustrative view showing an example of an "application management screen for system manager (additional function settings)" when the application is installed into the medical support system in which the service architecture support system according to the embodiment of the present invention is incorporated;

FIG. 26 is an illustrative view showing an example of an "application management screen for system manager (additional function/question settings)" when the application is installed into the medical support system in which the service architecture support system according to the embodiment of the present invention is incorporated;

FIG. 27 is an illustrative view showing an example of the "application management screen for system manager (additional function/question settings)" when the application is installed into the medical support system in which the service architecture support system according to the embodiment of the present invention is incorporated;

FIG. 28 is an illustrative view showing an example of the "application management screen for system manager (additional function/question settings)" when the application is installed into the medical support system in which the service architecture support system according to the embodiment of the present invention is incorporated;

FIG. 29 is an illustrative view showing an example of the "application management screen for system manager (additional function/question settings)" when the application is installed into the medical support system in which the service architecture support system according to the embodiment of the present invention is incorporated;

FIG. 31 is an illustrative view showing an example of an "application management screen for system manager (additional function/inspection record item settings)" when the application is installed into the medical support system in which the service architecture support system according to the embodiment of the present invention is incorporated;

FIG. 32 is an illustrative view showing an example of an "application management screen for system manager (settings of posted items, timing, and like)" when the application is installed into the medical support system in which the service architecture support system according to the embodiment of the present invention is incorporated;

FIG. 33 is an illustrative view showing an example of the "application management screen for system manager (settings of posted items, timing, and like)" when the application is installed into the medical support system in which the service architecture support system according to the embodiment of the present invention is incorporated;

FIG. 34 is an illustrative view showing an example of an "application management screen for system manager (inspection value settings)" when the application is installed into the medical support system in which the service architecture support system according to the embodiment of the present invention is incorporated;

FIG. 35 is an illustrative view showing an example of an "application management screen for system manager (start date settings)" when the application is installed into the medical support system in which the service architecture support system according to the embodiment of the present invention is incorporated;

FIG. 42 is an illustrative view showing an example of an "answer screen displayed on a timeline (patient side) of a group" of the specific patient: when the application is installed into the medical support system in which the service architecture support system according to the embodiment of the present invention is incorporated;

FIG. 44 is an illustrative view showing an example of a "choice screen displayed on a timeline (patient side) of a group" of the specific patient when the application is installed into the medical support system in which the service architecture support system according to the embodiment of the present invention is incorporated;

PREFERRED MODE FOR CARRYING OUT
THE INVENTION

A preferred embodiment of the present invention will be described below with reference to accompanying drawings.
(Form of Utilization of Medical Support Service)

Figure 1:
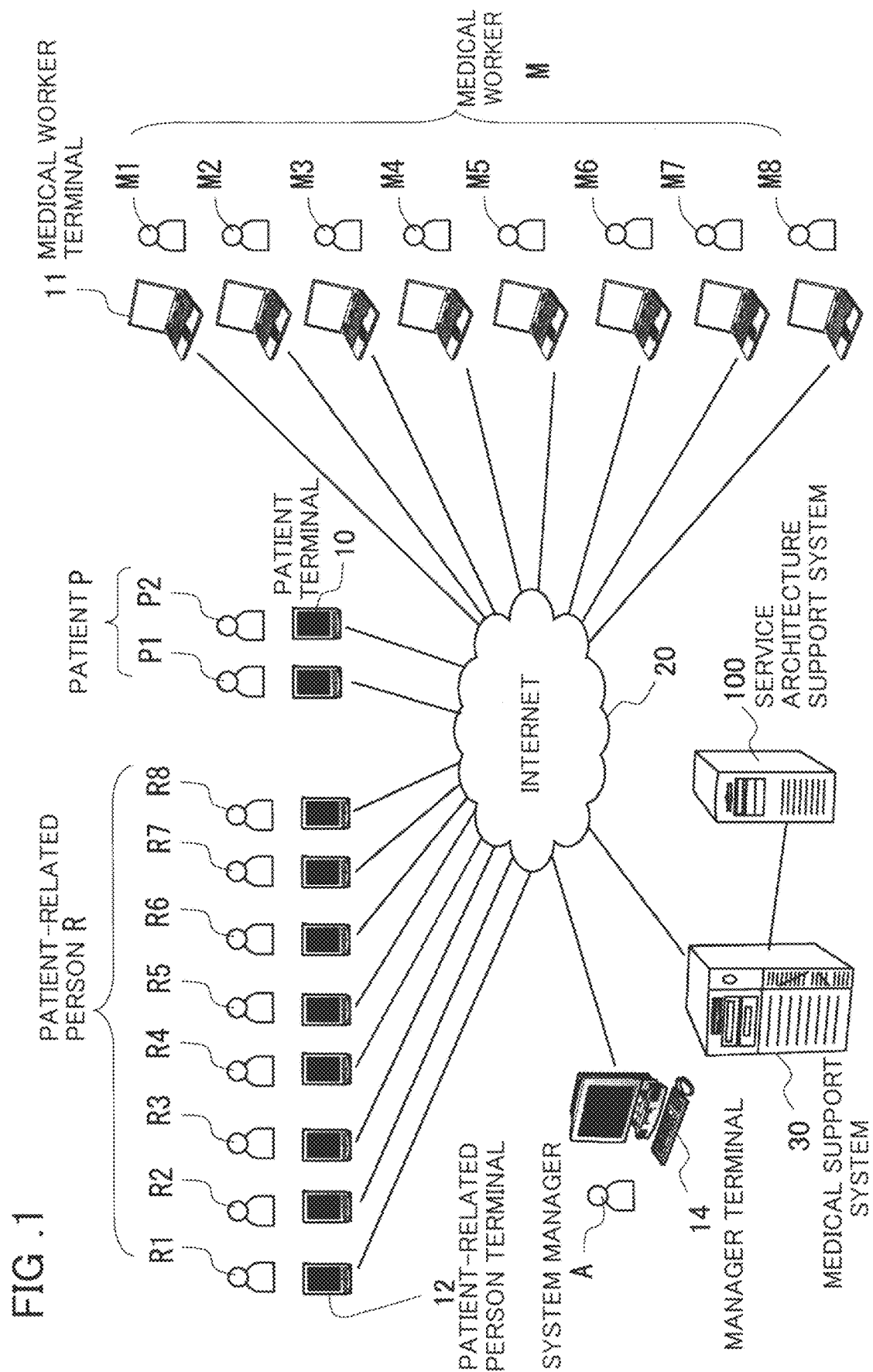
FIG. 1 is a conceptual diagram showing a state of utilization of a medical support system in which a service architecture support system according to an embodiment of the present invention is incorporated.

FIG. 1 shows an overall configuration when a medical support service, provided by a medical support system 30 in which a service architecture support system 100 according to an embodiment of the present invention is incorporated, is utilized.

In the following description, when individual patients are distinguished, they are represented as: "patient P1", "patient P2", "patient P3", and such, whereas when the individual patients are not distinguished, they are represented as: "patients P". Likewise, when individual medical workers are distinguished, they are represented as: "medical worker M1", "medical worker M2", and such, whereas when the individual medical workers are not distinguished, they are represented by "medical workers M". When individual patient-related persons are distinguished, they are represented as: "patient-related person R1", "patient-related person R2", and such, whereas when the individual patient-related persons are not distinguished, they are represented as: "patient-related persons R". When individual medical-related facilities are not distinguished, they are represented as: "medical-related facilities F", whereas when they are distinguished, they are represented as "medical-related facility F1", "medical-related facility F2", and such. When individual groups are not distinguished, they are represented as: "groups G", whereas when they are distinguished, they are represented as "group G11", "group G12", and such.

As shown in FIG. 1, after the patient P, the patient-related person R or the medical worker M who wants to utilize the medical support service performs user registration by a predetermined method, the medical support service is utilized through the Internet 20 serving as a communication network from a patient terminal 10 possessed by the patient P, a medical worker terminal 11 operated by the medical worker H or a patient-related person terminal 12 possessed by the patient-related person R (hereinafter, these terminals may also be collectively referred to as a "user terminal").

The patient P, the patient-related person R or the medical worker M who has performed the user registration serves as a "user" of the medical support service. Since the medical support service is realized by the medical support system 30, the "user" of the medical support service can be said to be the "user" of the medical support system 30. A patient P, the patient-related person R or the medical worker M who has not performed the user registration cannot utilize the medical support service.

When any one of the user terminals 10, 11 or 12 provides an instruction to the medical support system 30 through the Internet 20, by the operation of hardware and software installed within the medical support system 30, various operations and functions are executed, such as "user registration", "generation of a group", "invitation to group", "transmission and reception (communication) of a message", "regular registration", and "browsing of medical information", which will be described later. In this way, medical information of each patient and exchanged messages can be shared among a plurality of medical workers M, between the patient P and the medical worker M or among the patient P, the medical worker M and the patient-related person R, while protecting the privacy of the patient P, with the result that it is possible to provide a higher quality medical service to each patient P based on the shared medical information and messages.

Although the patient terminal 10 and the patient-related person terminal 12 are generally assumed to be portable terminals such as a portable phone and a smart phone, and each patient P or patient-related person R possesses his or her special terminal, a desktop or notebook personal computer, or a touch panel terminal can be used. Since the medical worker terminal 11 is often installed in the medical-related facility, though the medical worker terminal 11 is generally assumed to be a desktop or notebook personal computer, it is needless to say that a touch panel terminal or a portable terminal can be used. In short, as long as these terminals 10, 11 and 12 are terminal devices which can transmit and receive information to and from the medical support system 30 through the Internet 20 and produce a display, the form and configuration thereof are not limited.

Each patient P has one or more diseases, and receives, in a specific medical-related facility F, a medical service such as diagnosis and treatment from the medical worker M who belongs thereto. Although for simplification of description, in the present embodiment, it is assumed that only two patients P1 and P2 utilize this medical support service, it is needless to say that a larger number of patients P actually utilize the medical support service. In actuality, in the following description of the service architecture support system 100, a patient P3 who has diabetes receives, in the specific medical-related facility F, a medical service such as diagnosis and treatment from the medical worker M who belongs thereto.

The patient-related person R indicates a person who has a relationship with a patient P in any form such as a family member, a relative, a friend or an acquaintance of the patient P. Even when the medical worker M is a family member, a relative, a friend, an acquaintance or the like, of a certain patient P, the medical worker M can serve as the patient-related person R of the patient P. Here, although it is assumed that eight patient-related persons R1, R2, R3, R4, R5, R6, R7 and R8 participate therein, it is needless to say that a larger number or a smaller number of patient-related persons R may utilize the service architecture support system 100 according to the conditions of the patient P.

Medical worker M indicates a person such as a doctor or a nurse who is engaged in a medical service in the medical-related facility F. The medical workers M belong to various types of medical-related facilities F such as specialized clinics (small-scale clinics), hospitals (medium and large-scale medical facilities) and home-visit nursing stations, and provide, in the medical-related facilities F, medical services such as diagnosis and treatment to the patients P. Although here, it is assumed that only eight medical workers M1, M2, M3, M4, M5, M6, M7 and M8 participate therein, it is needless to say that a larger number or a smaller number of medical workers M actually participate therein.

Medical-related facility F indicates a facility in which the medical workers M provide medical services to the patients P, such as a small-scale clinic (clinic), a hospital which is larger than the clinic or a home-visit nursing station. As long as the facility provides a medical service such as diagnosis, treatment, nursing, care, inspection, surgery or consultation, the form and size thereof are not limited.

Although in FIG. 1, the patients P, the medical workers M and the patient-related persons R possess the terminals 10, 11 and 12, the present invention is not limited to this configuration. Each of the patients P, the patient-related persons R and the medical workers M have identification information (user ID) which can be uniquely identified, and thus even when they log in to the medical support system 30 from the same terminal, they can be distinguished, with the result that even when a plurality of persons share the same terminal, no problem occurs.

In FIG. 1, a system manager A, a manager terminal 14 which is operated by the system manager A, and a service architecture support system 100 are shown. Although the details of the service architecture support system 100 will be described later, the service architecture support system 100 is provided in order to generate an application framework 200 on the medical support system 30, and is operated so as to cooperate with the medical, support system 30. The system manager A is selected in order to manage the overall operation of the medical support system 30, uses the manager terminal 14 of the system manager A so as to access the medical support system 30 through the Internet 20, and thereby can perform the necessary processing. The system manager A manages not only the medical support system 30, but also the service architecture support system 100. In the present embodiment, the system manager A is set to perform the processing of "manager settings" (which will be described later) on an application program 220 which is developed by utilization of the application framework 200.

Figure 2:
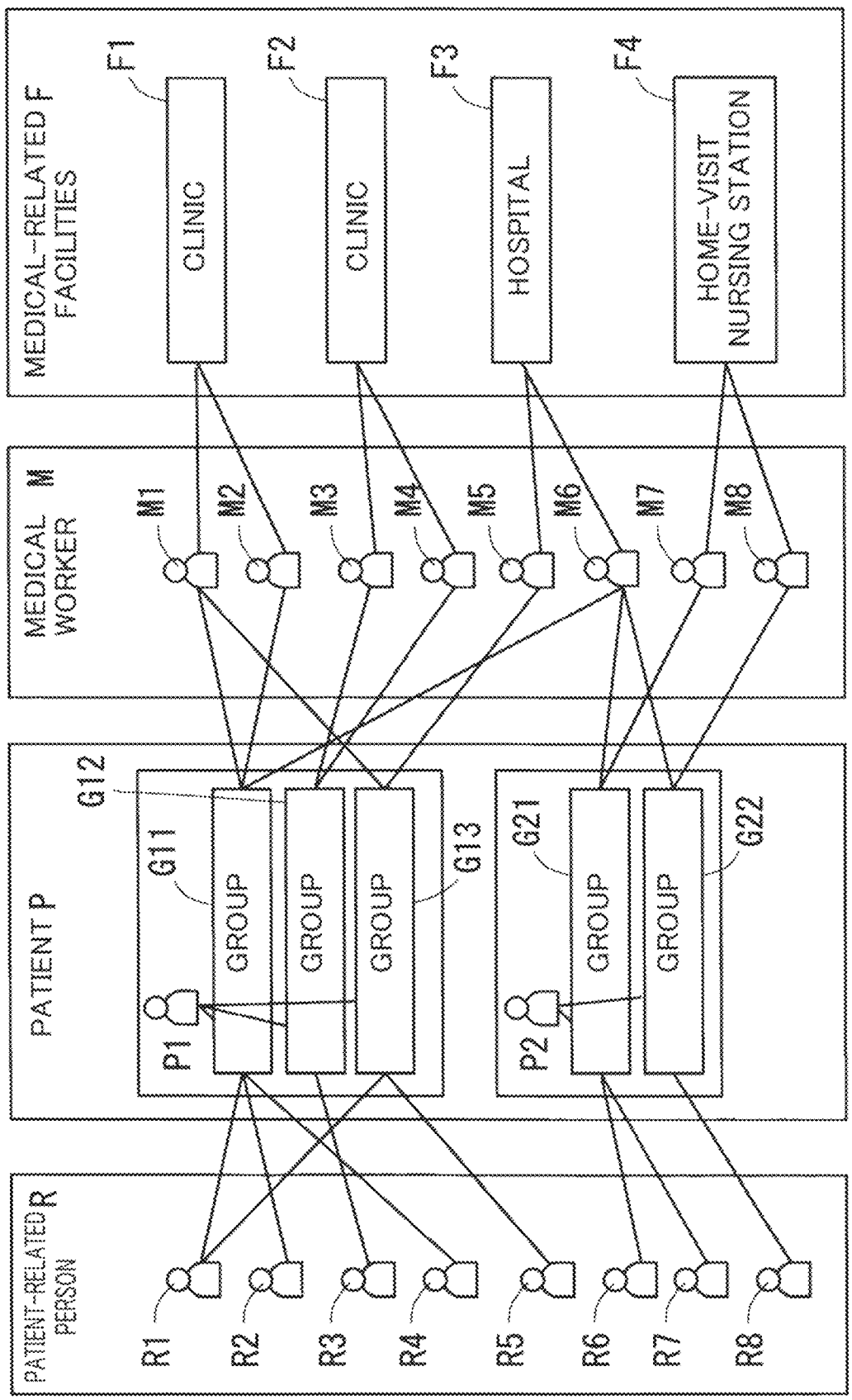
FIG. 2 is an illustrative view showing a correlation between patients, patient-related persons, medical workers, and medical-related facilities who/which participate in the medical support system shown in FIG. 1.

FIG. 2 is an illustrative view showing a correlation between the patients P1 and P2, the patient-related persons R1 to R8 and the medical workers M1 to M8 who utilize the medical support system 30, that is, those who are the users of the medical support system 30.

In the medical support system 30, a group G is registered for each disease of each patient P. In other words, a separate group G is formed for each of the diseases which each patient P has. Persons (participants) who participate in each group G (that is, group members) generally include, in addition to the patient P, at least one medical worker M who belongs to the medical-related facility F at which the patient P receives treatment and the like, and who is in charge of the patient P, and further include the patient-related person R who is added as necessary. Hence, the group members of each group G are generally formed with the patient P, the medical worker M in charge and the patient-related person R.

Any one of the medical-related facilities F to which the medical worker M participating in each group G belongs is generally subjected to "regular registration" for the group G (hence, the patient P). The medical-related facility F subjected to the "regular registration" is mainly responsible for the overall treatment policy of the disease of the patient P related to the group G.

However, the configuration of group members is not limited to such a case. For example, there may be a case where only the patient P and one or a plurality of medical workers M are group members (which do not include the patient-related person R), or there may be a case where only a plurality of medical workers M are group members (which do not include the patient P and the patient-related person R). The former occurs, for example, when the patient P does not want to inform the patient-related person R of the medical information of the patient P. The latter occurs when it is not desired to inform the patient P of the medical information of the patient P though it is desired to share the medical information of the patient P among a plurality of medical workers M who are involved in the treatment of the patient P. Since in a case where the patient P is not included in the group members, it is impossible to receive approval for the sharing of the medical information from the patient P on the medical support system 30, approval is separately received outside the medical support system 30. The approval is preferably received, for example, in writing. Naturally, only a process in which a piece of writing or the like that is digitalized is approved by the patient P may be added to the medical support system 30 for convenience. It is needless to say that a sub-system for receiving approval for sharing of the medical information from the patient P may be separately incorporated into the medical support system 30.

The participants (group members) of each group G except the patient P are called "supporters", regardless of whether they are the medical workers M or the patient-related persons R. This is because they support the patient P in some form. Hence, it can be said that the group members of each group G are formed with the patient P and at least one supporter when the patient P is included. It can be said that when the patient P is not included, the group members are formed with only a plurality of supporters.

As is clear from FIG. 2, the patient P1 has three diseases (here, diabetes, hyperlipidemia and gout are assumed), groups G11, G12 and G13 are respectively generated for the three diseases of the patient P1, and each of the groups G is associated with the medical-related facility F. Specifically, for the group G11 for diabetes treatment, a clinic F1 is subjected to regular registration, for the group G12 for hyperlipidemia treatment, a clinic F2 is subjected to regular registration, and for the group G33 for gout treatment, a hospital F3 is subjected to regular registration. As described above, here, the patient P1 belongs to the three groups G11, G12 and G13. As will be described later, the medical workers M who belong to the clinic F1, the clinic F2 and the hospital F3 which are subjected to regular registration, also belong to the groups G11, G12 and G13.

The patient P2 has two diseases (here, Alzheimer's disease and high blood pressure are assumed), groups G21 and G22 are respectively generated for the two diseases of the patient P2 and each of the groups G is associated with the medical-related facility F. Specifically, for the group G21 for Alzheimer's disease treatment, the hospital F3 is subjected to regular registration, and for the group G22 for high blood pressure treatment, a home-visit nursing station F4 is subjected to regular registration. As described above, here, the patient P2 belongs to the two groups G21 and G22. As will be described later, the medical workers M who belong to the hospital F3 and the home-visit nursing station F4, which are subjected to regular registration, also belong to the groups G21 and G22.

As described above, the group G11 is the group of the patient P1 for diabetes treatment, the group G12 is the group of the patient P1 for hyperlipidemia treatment and the group G13 is the group of the patient P1 for gout treatment. The group G21 is the group of the patient P2 for Alzheimer's disease treatment and the group G22 is the group of the patient P2 for high blood pressure treatment. As described above, since the group G is formed for each of diseases suffered by each patient P, and thus within each group G, the medical information on the specific disease of the specific patient P is shared, it is possible to expect an enhanced support effect, for the treatment and the like of the disease, with the result that it is possible to provide a higher quality medical service.

The medical worker M1 is a doctor, belongs to the clinic F1, and belongs as a supporter of the patient P1 to the group G11 for diabetes treatment and the group G13 for gout treatment. The medical worker M2 is a nurse, belongs to the same clinic F1 as the medical worker M1, and belongs as a supporter of the patient P1 to the group G11 for diabetes treatment.

The medical worker M3 is a doctor, belongs to the clinic F2, and belongs as a supporter of the patient P1 to the group G12 for hyperlipidemia treatment. The medical worker M4 is a nurse, belongs to the same clinic F2 as the medical worker M3, and belongs as a supporter of the patient P1 to the group G12 for hyperlipidemia treatment.

The medical worker M5 is a doctor, belongs to the hospital F3, and belongs as a supporter of the patient P1 to the group G13 for diabetes treatment. The medical worker M6 is a doctor, belongs to the same hospital F3 as the medical worker M5, and belongs as a supporter of the patient P1 to the group G11 for diabetes treatment and as a supporter of the patient P2 to the group G21 for Alzheimer's disease treatment and the group G22 for high blood pressure treatment.

The medical worker M7 is a nurse, belongs to the home-visit nursing station F4, and belongs as a supporter of the patient P2 to the group G21 for Alzheimer's disease treatment. The medical worker M8 is a nurse, belongs to the same home-visit nursing station F4 as the medical worker M7, and belongs as a supporter of the patient P2 to the group G22 for high blood pressure treatment.

As described above, in the medical support system 30, the groups G11, 612 and G13 are respectively generated for the three diseases (here, diabetes, hyperlipidemia and gout) of the patient P1, and for the groups G11, G12 and G13, the clinic F1, the clinic F2 and the hospital F3 are respectively subjected to regular registration. Hence, the medical workers M1 and M2 belonging to the clinic F3 are in charge of the treatment and the like of the disease (here, diabetes) in the group G11 of the patient P1 as primary doctors. The medical workers M3 and M4 belonging to the clinic F2 are in charge of the treatment and the like of the disease (here, hyperlipidemia) in the group G12 of the patient P1 as primary doctors. The medical workers M5 and M6 belonging to the hospital F3 are in charge of the treatment and the like of the disease (here, gout) in the group G13 of the patient P1 as primary doctors.

Likewise, the groups G21 and G22 are respectively generated for the two diseases (here, Alzheimer's disease and high blood pressure) of the patient P2, and for the groups G21 and G22, the hospital F3 and the home-visit nursing station F4 are respectively subjected to regular registration. Hence, the medical workers M5 and M6 belonging to the hospital F3 are in charge of the treatment and the like of the disease (here, Alzheimer's disease) in the group G21 of the patient P2 as primary doctors. The medical workers M7 and M8 belonging to the home-visit nursing station F4 are in charge of the treatment and the like of the disease (here, high blood pressure) in the group G22 of the patient P2 as primary doctors.

Various types of functions necessary for realizing the sharing and communication (message exchange) of the medical information described above within each group G are, as will be described later, provided by the medical support system 30 according to requests and instructions from the patient terminal 10, the medical worker terminal 11 and the patient-related person terminal 12.

(Configuration and Functions of Medical Support System)

Figure 3:
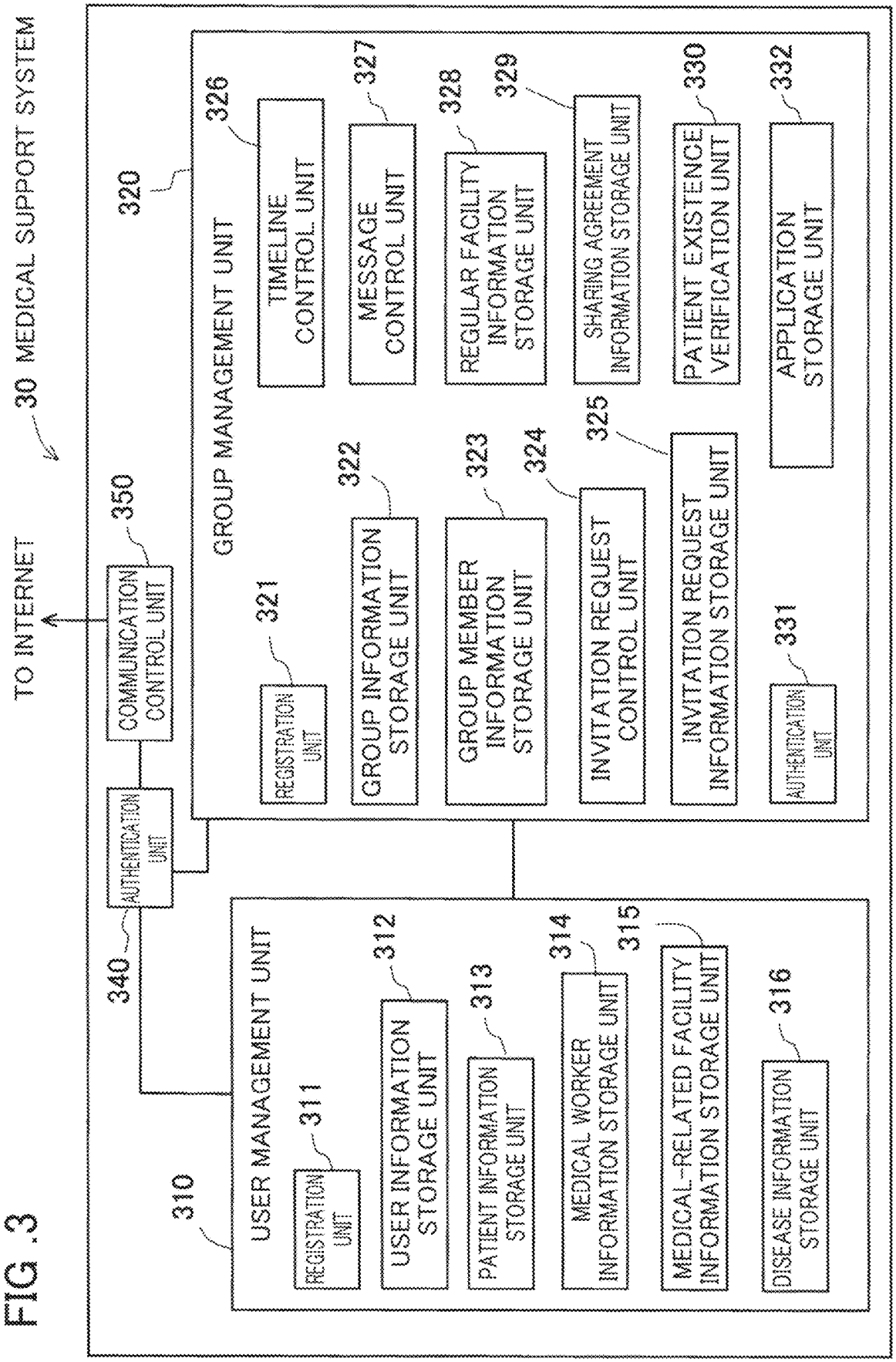
FIG. 3 is a functional block diagram showing an internal configuration of the medical support system shown in FIG. 1.

The configuration and the functions of the medical support system 30 in the present embodiment will be described next, with reference to FIG. 3. FIG. 3 is a functional block diagram showing an internal configuration of the medical support system 30.

As shown in FIG. 3, the medical support system 30 of the present embodiment includes a user management unit 310, a group management unit 320, an authentication unit 340 and a communication control unit 350.

The communication control unit 350 is a section which allows the transmission and reception of information between the medical support system 30 and a plurality of user terminals (that is, the patient terminal 10, the medical worker terminal 11 and the patient-related person terminal 12) through the Internet 20 serving as a communication network provided outside the medical support system 30. The communication control process of the communication control unit 350 is executed by a known method, and thus the description thereof will be omitted.

The authentication unit 340 is a section which authenticates whether or not a person who accesses the medical support system 30 from the user terminal 10, 11 or 12 through the Internet 20 is a regular user who receives user registration in the medical support system 30.

The authentication unit 340 is connected through the communication control unit 350 to the Internet 20 provided outside the medical support system 30. On the condition that predetermined authentication is received in the authentication unit 340, the user management unit 310 and the group management unit 320 transmit and receive information to and from the patient terminal 10, the medical worker terminal 11 and the patient-related person terminal 12 provided outside the medical support system 30. Then, only when the person is authenticated as the regular user in the authentication unit 340, the person is allowed to access the user management unit 310 and the group management unit 320. Then, the user can first utilize the medical support service provided by the medical support system 30.

The user management unit 310 will be described next.

The user management unit 310 is a section which registers (user registration) individual users who utilize the medical service provided from the medical-related facility F or users who support the users, that is, the patient P, the medical worker M and the patient-related person R and which manages the registered users. The user management unit 310 includes a registration unit 311, a user information storage unit 312, a patient information storage unit 313, a medical worker information storage unit 314, a medical-related facility information storage unit 315 and a disease information storage unit 316.

The registration unit 311 is formed with software for controlling the operation thereof, and controls an operation on the user registration as a whole in the user management unit 310. For example, for the user terminal 10, 11 or 12 which accesses the medical support system 30, a predetermined user registration screen (see FIG. 16A) is displayed, and a person who wants to utilize the medical support service (applicant for utilization) is prompted to input and transmit predetermined personal information. When the predetermined personal information is transmitted from the user terminal 10, 11 or 12 to the medical support system 30 accordingly, the personal information is stored as the "user information" of the applicant for utilization in the user information storage unit 312. As necessary, the registration unit 311 reads and utilizes the user information stored in the user information storage unit 312, and, for example, corrects and deletes the user information.

The user information storage unit 312 is formed with: an information storage medium such as a hard disk; and software which controls operations of recording, reproduction, deletion, and the like of information on the information storage medium, and stores, according to an instruction from the registration unit 311, the user information, that is, the necessary information of the patient P, the medical worker M and the patient-related person R serving as the users. Here, "user identification information" (user ID) which can be uniquely identified is assigned to each user. The user information is stored, for example, in the form of a user table as shown in FIG. 4(a).

The patient information storage unit 313 is formed with: an information storage medium such as a hard disk; and software which controls operations of recording, reproduction, deletion, and the like of information on the information storage medium, and stores, according to an instruction from the registration unit 311, the personal information of the patient P. Here, a "patient ID" which can be uniquely identified is assigned to each patient P. The "patient ID" is "patient identification information" and is also "service recipient identification information". The personal information of the patient P is stored, for example, in the form of a patient table as shown in FIG. 4(b).

The medical worker information storage unit 314 is formed with: an information storage medium such as a hard disk; and software which controls operations of recording, reproduction, deletion, and the like of information on the information storage medium, and stores, according to an instruction from the registration unit 311, the personal information of the medical worker M. Here, a "medical worker ID" which can be uniquely identified is assigned to each medical worker M. The "medical worker ID" is "medical worker identification information" and is also "business worker identification information". The personal information of the medical worker M is stored, for example, in the form of a medical worker table as shown in FIG. 4(c).

The medical-related facility information storage unit 315 is formed with: an information storage medium such as a hard disk; and software which controls operations of recording, reproduction, deletion, and the like of information on the information storage medium, and stores, according to an instruction from the registration unit 311, the necessary information of the medical-related facility F. Here, a "medical-related facility ID" which can be uniquely identified is assigned to each medical-related facility F. The "medical-related facility ID" is "medical-related facility identification information". The necessary information of the radical-related facility F is stored, for example, in the form of a medical-related facility table as shown in FIG. 4(d).

The disease information storage unit 316 is formed with: an information storage medium such as a hard disk; and software which controls operations of recording, reproduction, deletion, and the like of information on the information storage medium, and stores, according to an instruction from the registration unit 311, disease information. Here, a "disease ID" which can be uniquely identified is assigned to each disease. The "disease ID" is "disease identification information". The disease information is stored, for example, in the form of a disease table as shown in FIG. 5(b).

The group management unit 320 will be described next.

The group management unit 320 is a section which manages the group G that is registered and formed for each disease of each patient P in the medical support system 30. The group management unit 320 executes a large number of functions such as the new registration of a group, the storage of information of a group member, the control of an invitation request, a timeline and a message, and regular registration. The group management unit 320 includes a registration unit 321, a group information storage unit 322, a group member information storage unit 323, an invitation request control unit 324, an invitation request information storage unit 325, a timeline control unit 326, a message control unit 327, a regular facility information storage unit 320, a sharing agreement information storage unit 329, a patient existence verification unit 330, an authentication unit 331 and an application storage unit 332. The application storage unit 332 is added to the medical support system 30 for the service architecture support system 100 (application framework 200) which will be described later.

The registration unit 321 is formed with software for controlling the operation thereof, and generates and registers the group G according to a request from the medical worker M or the patient P for each disease of each patient P. The registration unit 321 executes, according to a request from the medical worker M or the patient P, a process related to the "regular registration" which will be described later (specifically, the association of the patient P, the disease and the medical-related facility F).

The group G is generated according to a request from the medical worker M when the medical worker M performs "patient group registration". The "patient group registration" indicates that the medical worker M registers, in the medical support system 30, the patient P and the disease of the patient P on which the medical-related facility F of the medical worker M performs treatment and the like. Here, the medical worker M specifies the patient P and the disease of the patient P on which the medical-related facility F of the medical worker M performs treatment and the like, and registers them in the medical support system 30, and this is so that the medical information of the patient P can be shared within the medical-related facility F to which the medical worker M belongs. The registration unit 321 automatically generates the group G in synchronization with the "patient group registration", and stores information related to the generated group G in the group information storage unit 322.

The number of first group members in the group G generated in this way is zero except in a case where previously determined members (default members) are automatically invited. The medical worker M who has performed the "patient group registration" and the patient P who is the target of the "patient group registration" are not group members. In order for the medical worker M who has performed the "patient group registration" to become a group member, the medical worker M transmits an invitation request to himself or herself and needs to provide approval. Likewise, in order for the patient P who is the target of the "patient group registration" to become a group member, the patient P transmits an invitation request to the patient P and needs to receive approval.

The group G is generated according to a request from the patient P when the patient P requests "regular registration". Here, the patient P selects one of the medical-related facility F at which the patient P receives treatment and the like and the medical-related facility F from which the patient P will receive treatment and the like, requests "regular registration" and receives approval from the medical-related facility F. This is because the patient P wants mainly to receive treatment and specifies the medical-related facility F which is mainly responsible for the overall treatment policy. The registration unit 321 automatically generates the group G in synchronization with "regular registration", and stores information (group information) related to the generated group G in the group information storage unit 322. Specifically, in the "regular registration", the patient P, the disease and the medical-related facility F are associated with each other.

The number of first group members in the group G generated in this way is zero except in a case where default members are automatically Invited. The patient P who requests "regular registration" and the medical worker M of the medical-related facility F which is the target of the "regular registration" are not group members. In order for the patient P who requests "regular registration" to become a group member the patient P transmits an invitation request to himself or herself and needs to provide approval. Likewise, in order for the medical worker M related to the "regular registration" to become a group member, the patient P who requests "regular registration" transmits an invitation request to the medical worker M and needs to receive approval.

The group information storage unit 322 is formed with: an information storage medium such as a hard disk; and software which controls operations of recording, reproduction, deletion and the like of information on the information storage medium, and stores the group information, that is, information indicating which one of diseases of a specific patient P each group G is related to and which one of the medical-related facilities F is registered as a "regular facility". The "group information" is stored, for example, in the form of a group table as shown in FIG. 5(c).

The group member information storage unit 323 is formed with: an information storage medium such as a hard disk; and software which controls operations of recording, reproduction, deletion, and the like of information on the information storage medium. The group member information storage unit 323 stores group member information, that is, information related to the patient P who can be said to be the owner of each group G and the medical worker M and the patient-related person R who participate in each group G as supporters of the patient P. The "group member information" is stored, for example, in the form of a group participation table as shown in FIG. 5(d).

The invitation request control unit 324 is formed with software for controlling the operation thereof, identifies a non-group member (that is, the patient P, the medical worker M or the patient-related person R) who is desired to participate in each group G and controls an "invitation request" which is sent to the non-group member. The invitation request control unit 324 transmits, according to an instruction from the user, that is, the medical worker M, the patient P or the patient-related person R, the invitation request to the identified non-group member by electronic mail. The invitation request control unit 324 receives a reply (which indicates whether or not the invitation request is approved) from the user who receives the invitation request.

The invitation request is an invitation which is sent to the user; who is desired to participate in the desired group G so as to become a group member and which is in the form of electronic mail. Although any one of the patient P, the medical worker M and the patient-related person R can transmit the invitation request, the sender needs to receive "permission" of a predetermined manager before transmitting the invitation request to the user who is desired to participate in the group G. This permission is determined by the manager with consideration given to, for example, whether or not the user who is invited is appropriate as a group member and whether or not any problem occurs by the participation of the user. As for the manager, there is a "medical worker-side manager" and a "patient-side manager". The "medical worker-side manager" is a medical worker M (who is also the user) who has the authority to "allow" or "reject" the transmission of the invitation request, and is set for each medical-related facility F or for each group. As the "medical worker-side manager", or example, the director, the office manager, or the like of a clinic is specified. The "patient-side manager" is the patient P (who is also the user) or a user, such as a family member or a friend of the patient P, who receives, from the patient P, the authority to "allow" or "reject" the transmission of the invitation request, and is set for each patient P or for each group. As the "patient-side manager", for example, a parent, the spouse, a child, a close friend, or the like of the patient P is specified.

In general, even when the medical worker M transmits the invitation request or even when the patient P or the patient-related person R transits the invitation request, it is specified that the invitation request cannot be transmitted unless both the permission of the "medical worker-side manager" and the permission of the "patient-side manager" are received. In other words, a setting is made so as to determine the rejection of the transmission of the invitation request with consideration given to both the conditions of the side of the medical worker M and the conditions of the side of the patient P. This is because since a group member can browse the medical information of the patient P and messages, both the patient P and the medical worker M are significantly affected by who becomes a group member. However, there is no limitation to this configuration. A configuration may be adopted in which when the permission of either the "medical worker-side manager" or the "patient-side manager" is received, the invitation request can be transmitted, or a configuration may be adopted in which when only the permission of the "medical worker-side manager" is received, the invitation request can be transmitted. This point can be determined according to needs or requests.

As described above, in the medical support system 30, in order to "complete" the transmission of the invitation request ("completion of the invitation"), at least one of the permission of the "medical worker-side manager" and the permission of the "patient-side manager" is needed, with the result that no problem occurs as a result of the addition of a group member.

When the user who receives the invitation request which is transmitted as a result of the reception of both or at least one of the "permission" of the "medical worker-side manager" and the "permission" of the "patient-side manager" participates in the group G specified by the invitation request, the user preferably "approves" the invitation. Then, the user is automatically added as a group member. When the user does not participate in the group G, the user preferably "rejects" the invitation. As described above, the user who receives the invitation request determines whether or not to "approve" the invitation so as to be able to select participation or non-participation in the group G.

Although the user who approves the invitation becomes a group member in the group G, all the group members (specifically, the medical worker M and the patient-related person R) other than the patient P are the supporters of the patient P. Between the group members, the medical information of the patient P and messages are shared according to a sharing rule selected by the patient P. Hence, for example, when the patient P wants to receive a second opinion on his or her disease from a medical worker M in another medical-related facility F or when the patient P has a patient-related person R such as a family member, a relative or a friend who wants to know the treatment progress and the like on the disease of the patient P, the invitation request is transmitted to such a person. In this way, the medical information on the specific disease of the patient P in the medical-related facility F can be shared among a plurality of medical workers M and patient-related persons R and the patient P including medical workers in other medical-related facilities while ensuring the uniqueness of the medical information.

The settings of the "medical worker-side manager" and the "patient-side manager" are stored in the invitation request information storage unit 325. The process of the "permission" by the "medical worker-side manager" and the "patient-side manager" is executed with the invitation request control unit 324. The generation and transmission of the invitation request and the reception of a reply from an invitation request receiver are executed with the invitation request control unit 324.

The invitation request information storage unit 325 is formed with: an information storage medium such as a hard disk; and software which controls operations of recording, reproduction, deletion, and the like of information on the information storage medium. The invitation request information storage unit 325 stores "invitation request information" which is generated according to a request with the invitation request control unit 331, that is, various types of information indicating who sends the invitation request and who receives the invitation request, and information on the rejection of the invitation request by the manager. The invitation request information storage unit 325 also stores the details of the reply from the invitation request receiver (the approval of the invitation request or the rejection of the invitation request) and the settings of the "medical worker-side manager" and the "patient-side manager". The "invitation request information" is stored, for example, in the form of an invitation request table as shown in FIG. 6(a).

The reason why an "invitee passphrase" is included in the invitation request table of FIG. 6(a) is because whether or not the person who receives the invitation request is an authorized invitee, that is, whether or not the person is the authorized person, is checked with this passphrase. In order for the person who receives the invitation request to participate in the group of the inviter related to the invitation request, the person needs to access a URL described in the electronic mail of the invitation request and to input the passphrase in an invitation request approval screen displayed there. When the passphrase which is input does not agree with the "invitee passphrase" stored in the invitation request table, the person cannot participate in the group, with the result that it is possible to easily identify the authorized person of the invitee.

The timeline control unit 326 is formed with software for controlling the operation thereof, and controls a "timeline" (that is, an information display region) which is assigned to each group G. Specifically, the information display region called the "timeline" is assigned to a newly generated group G, and the shared medical information is displayed in the timeline in a predetermined order (for example, in an order in which information is posted). Since information to be displayed and parameters such as a time at which the information is displayed are sent from the medical worker, terminal 11 through the Internet 20 to the group management unit 330, the timeline control unit 335 displays, according to the parameter, the information which is sent in the timeline.

Figure 9:
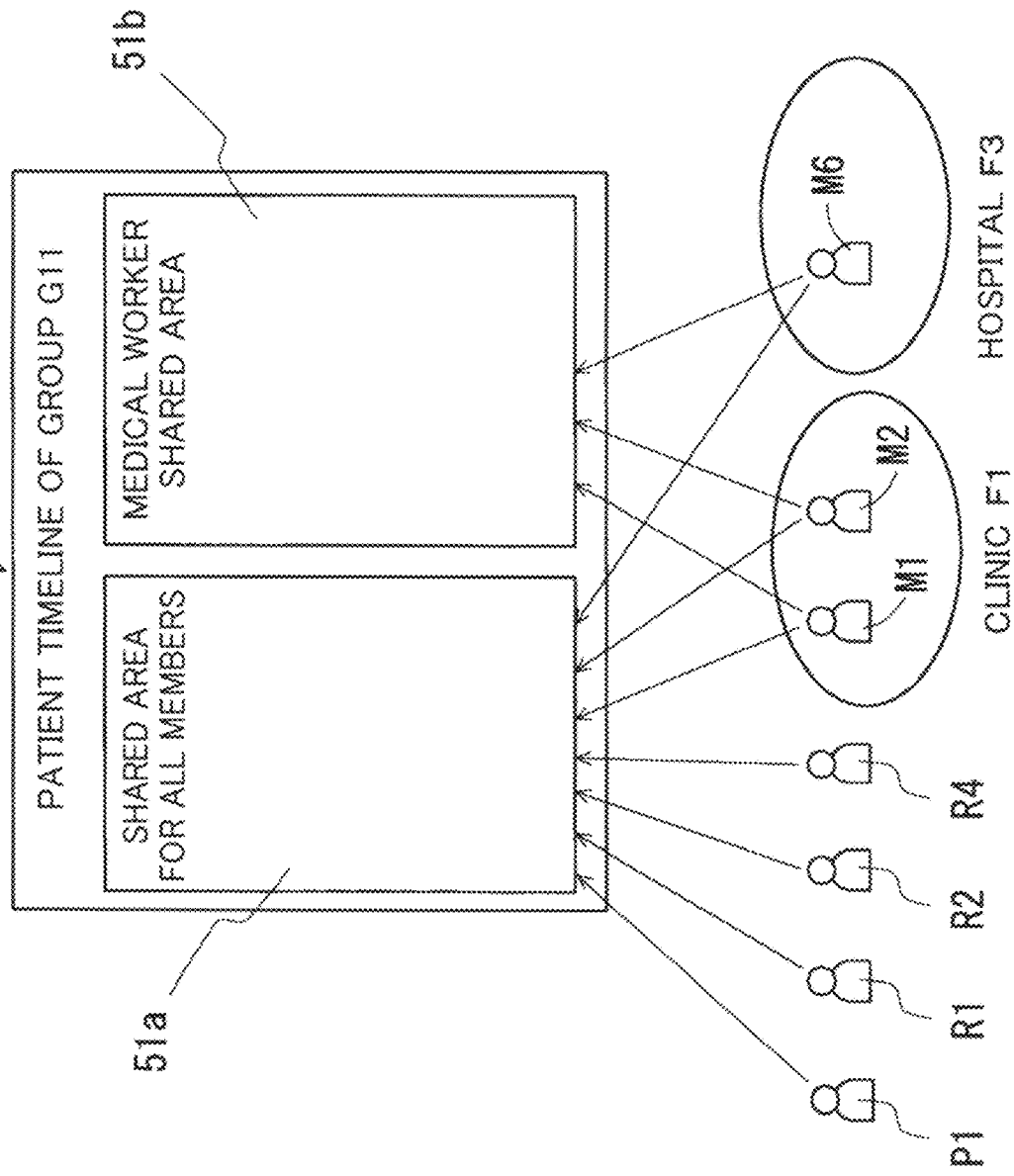
FIG. 9 is an illustrative view showing a relationship between a display region which is generated for each disease of each patient in a timeline formed with the medical support system shown in FIG. 1 and persons who can access the display region.

An example of the timeline is shown in FIG. 9. This timeline 51 is generated for the group G11 for diabetes treatment of the patient P1, and includes a shared area for all members 51a and a medical worker shared area 51b. In the shared area for all members 51a, information which is shared by all the members in the group G11 is displayed. In the medical worker shared area 51b, information which is shared only by the medical workers M in the group G11 is displayed. Hence, the medical information displayed in the shared area for all members 51a can be shared among all the members in the group G11, and the patient P1, the medical workers M1 and M2 who belong to the clinic F1, the medical worker M6 who belongs to the hospital F3 and the patient-related persons R1, R2 and R4 can freely perform posting and browsing. By contrast, the medical information displayed in the medical worker shared area 51b can be shared only among the medical workers in the group G11, and the medical workers M1 and M2 who belong to the clinic F1 and the medical worker M6 who belongs to the hospital F3 can freely perform posting and browsing.

The message control unit 327 is formed with software for controlling the operation thereof, and controls the transmission and reception of messages from one group member to other group members. For this control, for example, a message transmission reservation table shown in FIG. 7(a) is used.

A patient attribute table shown in FIG. 7(b) is used to store the attributes of individual patients P, and is used when the message control unit 336 selectively transmits a predetermined message to some patients P.

The regular facility information storage unit 328 is formed with: an information storage medium such as a hard disk; and software which controls operations of recording, reproduction, deletion, and the like of information on the information storage medium. The regular facility information storage unit 328 stores "regular facility information" which is utilized and generated in the "regular registration" (the association of the patient P, the disease and the medical-related facility F) process that is executed with the registration unit 321. The details of the regular registration are disclosed in Patent Document 1 described previously, and thus the description thereof will be omitted. The "regular facility information" is stored, for example, in the form of a medical-related facility patient table as shown in FIG. 5(*a*).

The registration unit 321 displays a predetermined sharing rule selection screen in an inquiry screen for sharing of the medical information described above, and prompts the user to select a sharing rule, that is, the sharing range of the medical information. For example, two choices for the sharing rule are set, and one is that "the medical information is shared only within the medical-related facility F related to the regular registration" and the other is that "the medical information is shared within the medical-related facility F related to the regular registration and among all the group members including the patient P related to the regular registration". When any one of the sharing rules is selected, the registration unit 321 stores an answer indicating "agreeing with the sharing" and the selected sharing rule in the sharing agreement information storage unit 329. It is needless to say that three or more sharing rules may be set.

The sharing agreement information storage unit 329 is formed with: an information storage medium such as a hard disk; and software which controls operations of recording, reproduction, deletion, and the like of information on the information storage medium, and stores a statement of intention (sharing agreement information) which is generated with the registration unit 321 and which indicates "agreeing with sharing of the medical information of the user" and the selected sharing rule. The sharing agreement information and the selected sharing rule are stored, for example, in the form of a medical information sharing table shown in FIG. 6(*c*).

The patient existence verification unit 330 is formed with software for controlling the operation thereof, and verifies "whether or not the patient P who requests regular registration exits", that is, "whether or not the patient P is the authorized person or whether or not another person is posing as the authorized person". This patient existence verification process is preferably performed before the start of the regular registration process described above. FIG. 6(*d*) shows an example of an NFC terminal table which is produced in order to manage an NFC terminal.

The authentication unit 331 is formed with software for controlling the operation thereof, and checks whether or not the patient P, the medical, worker M or the patient-related person R who accesses the specific group G of the medical support system 30 through the user terminal is the authorized member, that is, whether or not the patient P, the medical worker M or the patient-related person R has the authority to access the timeline of the group G. Then, when it is confirmed that the patient P, the medical worker M or the patient-related person R is the authorised member, the patient P, the medical worker M or the patient-related person R is allowed to access the timeline of the group G. When it is confirmed that the patient P, the medical worker M or the patient-related person R is not the authorized member, the medical worker M or the patient-related person R is prevented from accessing the timeline of the group G.

The application storage unit 332 is added for the service architecture support system 100 which will be described later, and is formed with: an information storage medium such as a hard disk; and software which controls operations of recording, reproduction, deletion, and the like of information on the information storage medium. The application storage unit 332 is a section which stores a file (application configuration file) itself that configures all applications 220 developed by utilization of the application framework 200 (which is generated with the service architecture support system 100) and information that is utilized in the applications 220. The application storage unit 332 stores all the applications 220 (that is, the application configuration file of the applications 220) which are uploaded from a developer terminal 13 that develops the applications 220 into the medical support system 30 and which are installed, and additionally stores settings information (for example, information related to the manager settings and information provided by the user settings) used when each of the applications 220 is executed and the like.

Figure 8:
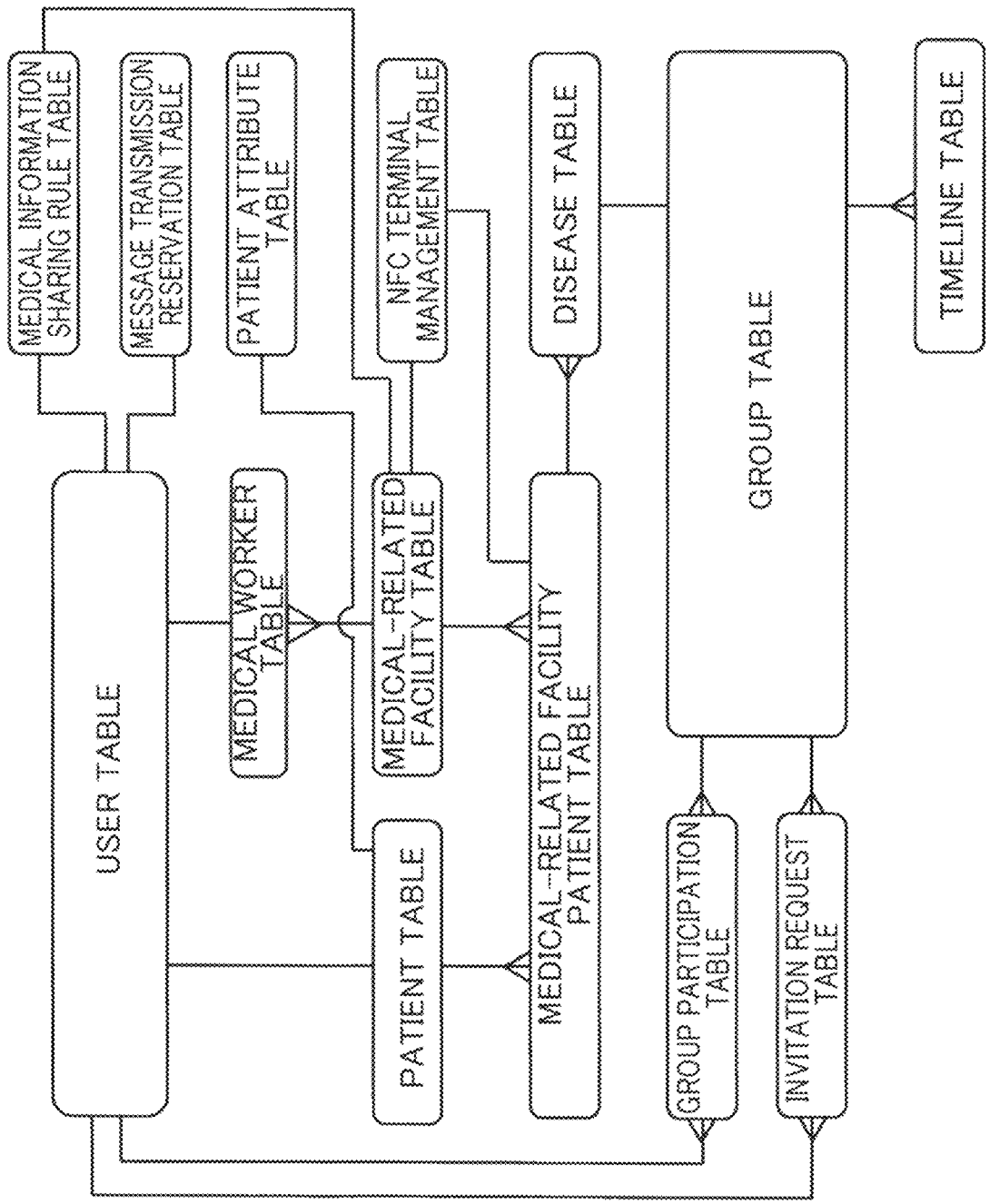
FIG. 8 is an illustrative view showing a relationship between all the tables used in the medical support system shown in FIG. 1.

Various types of tables which are used in the medical support system 30 and which are described above have a relationship as shown in FIG. 8.

(Operation of Medical Support System)

In the medical support system 30 having the configuration described above, in order to share the medical information and messages, the group G is registered and generated for each disease of each patient P. The production of the group G is performed, as described above, with the patient group registration performed by the medical worker M or with the regular registration performed by the patient P. The group members in the group G are increased in number, (excepting the default members), as necessary, by the invitation of the patient P, the medical worker M or the patient-related person R, and are decreased in number as necessary. Since the details of these operations of the medical support system 30 are disclosed in Patent Document 1, and are not related to the service architecture support system 100 according to the present embodiment, the description thereof will be omitted.

The description of the operations of user registration, new patient registration, new medical worker registration, and the like in the medical support system 30 will be omitted due to the same reason.

(Configuration of Application Framework)

The configuration of the application framework 200 generated with the service architecture support system 100 according to the embodiment of the present invention will be described next with reference to FIGS. 10 to 13.

In the following description, when individual developers who develop desired applications 220 with the application framework 200 are distinguished, they are represented as: "developer D1", "developer D2", and such, whereas when the individual developers are not distinguished, they are represented as: "developers D". The developer terminal 13 (see FIGS. 11 and 12) operated by the developer D and the manager terminal 14 (see FIG. 1) operated by the system manager A of the medical support system 30 may be, as with the user terminal described above (that is, the patient terminal 10, the medical worker terminal 11 or the patient-related person terminal 12), portable terminals such as a portable phone and a smart phone, desktop or notebook personal computers, or touch panel terminals. The form and configuration thereof are not limited.

Figure 10:
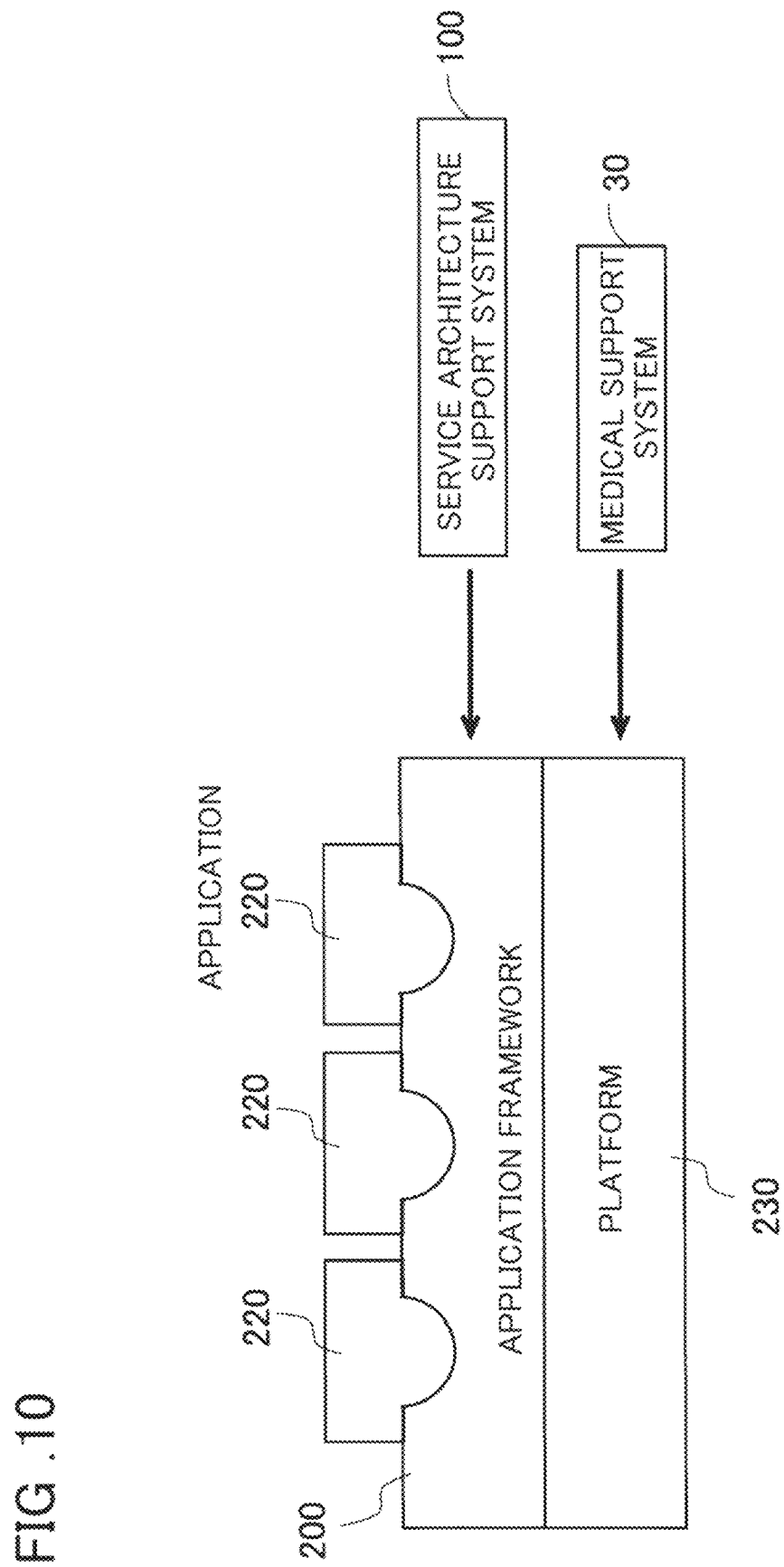
FIG. 10 is a conceptual diagram showing a relationship between a platform formed with the medical support system shown in FIG. 1, an application framework generated with the service architecture support system according to the embodiment of the present invention and applications.
Figure 11:
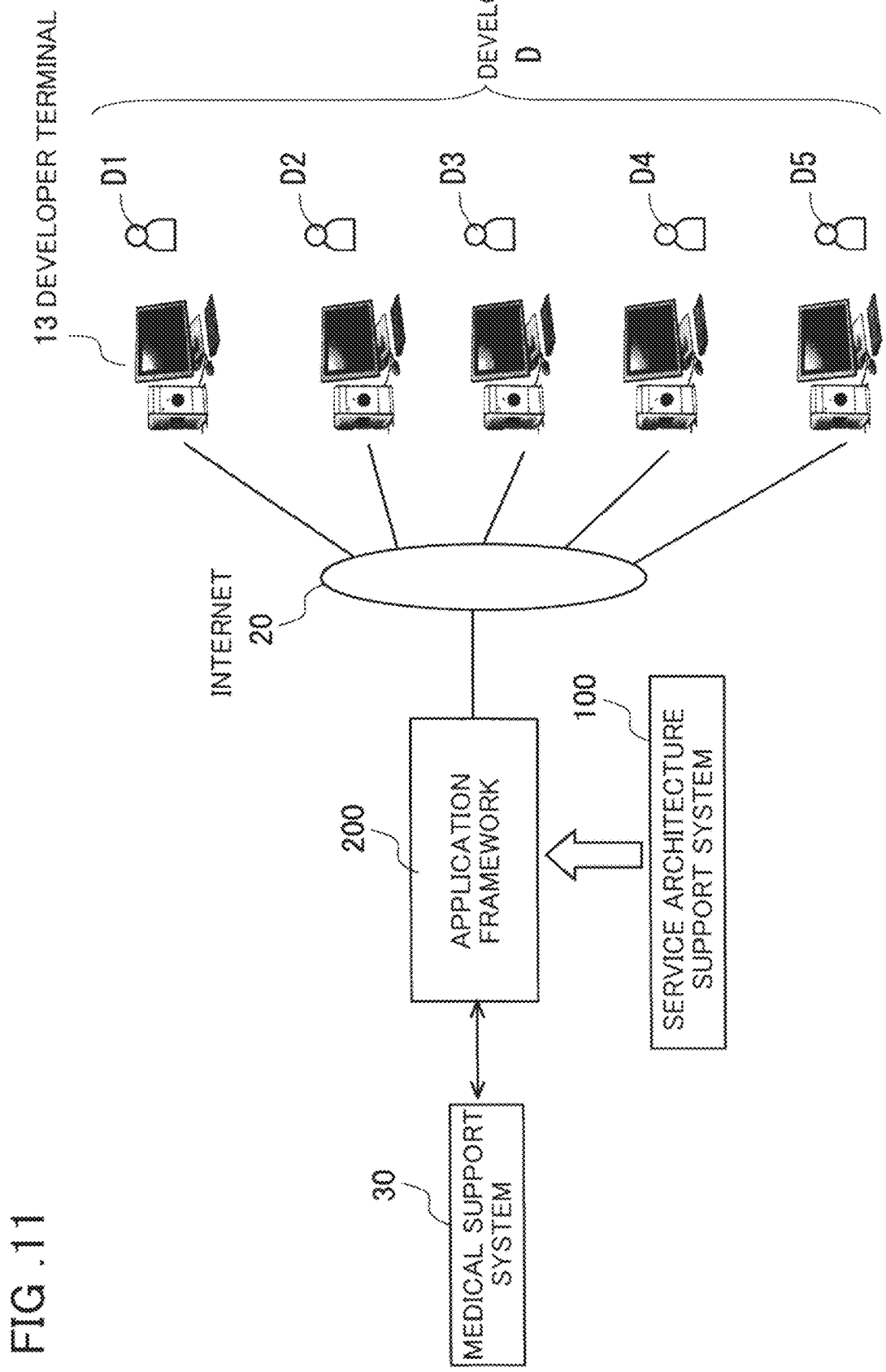
FIG. 11 is a conceptual diagram showing a relationship between the medical support system shown in FIG. 1, the application framework generated with the service architecture support system according to the embodiment of the present invention and developer terminals.

As shown in FIGS. 10 and 11, the application framework 200 is constructed on the medical support system 30 serving as a platform, and a plurality of developer terminals 13 can be connected to the application framework 200 through the Internet 20. Each of the developers D1 to D5 operates his or her developer terminal 13 so as to access the application framework 200 through the Internet 20, and uses, as necessary, specific functions prepared in the application framework 200 so as to be able to efficiently develop the desired application (application program) 220 which is operated on the medical support system 30.

The application 220 (that is, a file which configures the application 220) which is developed by utilization of the application framework 200 is uploaded from the developer terminal 13 through the Internet 20 into the medical support system 30, is passed though predetermined installation processing and is stored within the system 30, specifically, in the application storage unit 332 (see FIG. 3) provided within the group management unit 320. Thereafter, a service (new medical service) provided by the application program 220 can be utilized from the medical support system 30. The details of the new medical service (for example, in the case of a medication support app, what questions the patient is asked, what inspection data is collected, and the like) are determined according to the settings of the system manager of the medical support system 30. The user (that is, the patient P, the medical worker M or the patient-related person R) of the medical support system 30 who wants to utilize the new medical service preferably only selects (clicks), on an application selection screen (see, for example, FIGS. 19, 20 and 22) displayed on the user terminal (that is, the patient terminal 10, the medical worker terminal 11 or the patient-related person terminal 12) of the user, the icon of the application 220 desired by the user. In this way, it is possible to utilize the new medical service from the user terminal 10, 11 or 12 of the user. It is needless to say that the uploaded application 220 (that is, the application configuration file) may be stored within the service architecture support system 100 instead of being stored within the medical support system 30.

Figure 12:
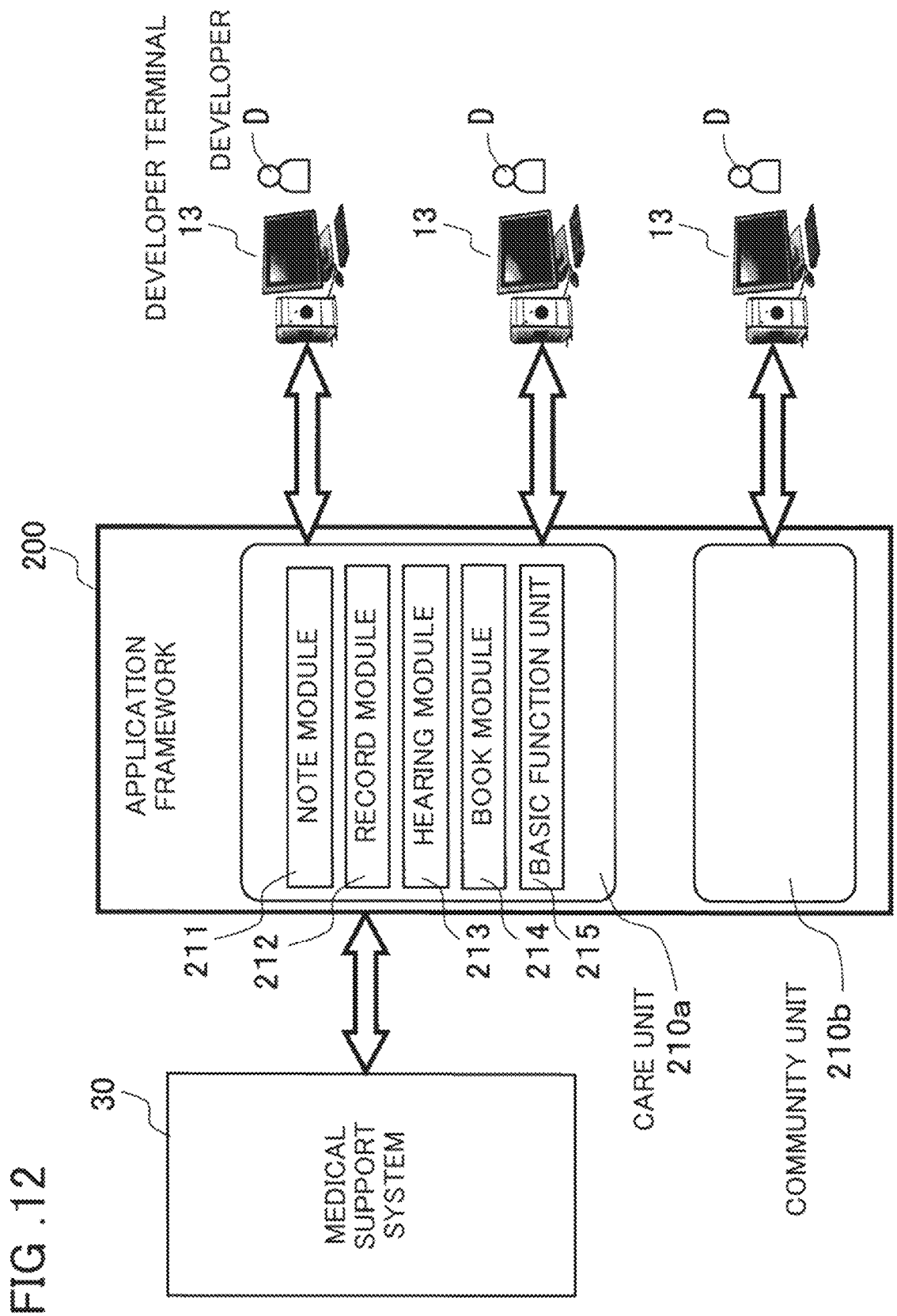
FIG. 12 is a conceptual diagram showing a relationship between the medical support system shown in FIG. 1, the application framework generated with the service architecture support system according to the embodiment of the present invention and the developer terminals.

The internal configuration of the application framework 200 is as shown in FIGS. 12 and 13. FIG. 12 shows a state where the application 220 is developed by utilization of the application framework 200, and FIG. 13 shows a state where the application 220 thus developed is utilized. As shown in both the figures, in the application framework 200, two units 210a and 210b which have different functions according to their purposes are provided.

Although here, for simplification of description, an example where the two units 210a and 210b are provided is illustrated, the present invention is not limited to this configuration. It is needless to say that the total number of these units may be one or three or more and that arbitrary settings can be made as necessary.

The unit 210a is formed as a "care unit", and is prepared so that, for example, additional medical services associated with various types of care (treatment) such as medication management, lifestyle improvement, diabetes medication support, team medical support, pressure ulcer care and rehabilitation support can be efficiently constructed on the medical support system 30 with the applications 220 and that the services described above can be provided to the user of the medical support system 30 at reasonable prices. This is because when these types of additional medical services can be provided, it is possible to realize multi-professional cooperation of medical experts (that is, cooperation between multi-professional workers such as a doctor, a nurse, a nutritionist a care manager and a helper) in order to support medical sites. Hence, in the care unit 210a, four sharing function modules (specific function modules) which have specific functions are provided so as to be able to be effectively utilized for the development of various applications 220 which provide these types of services. These modules will be described later.

The unit 210b is formed as a "community unit", and is prepared so that, for example, additional medical services associated with community production/operation such as various types of coordination, consultation reception, advice and information provision which function as cooperation windows between multi-professional workers can be efficiently constructed on the medical, support system 30 with the applications 220 and so that the services described above can be provided to the user of the medical support system 30 at reasonable prices. When these types of additional medical services can be provided, it is possible to realize cooperation window functions in the medical/care field such as a home medical consultation window, a care consultation window regional comprehensive support and medical coordination. Hence in the community unit 210b, a plurality of sharing function modules (specific function modules) (not shown) which are different from the "care unit" are provided so as to be able to be effectively utilized for the development of various applications 220 which provide these types of services.

Although the community unit 210b includes, according to the purposes (services) thereof, sharing function modules different from the sharing function modules of the care unit 210a, this is only the difference between both the units 210a and 210b, and since the roles of both the units 210a and 210b in the application framework 200 are the same as each other, the description of the sharing function modules of the community unit 210b will be omitted here.

The internal configuration of the care unit 210a will be described next with reference to FIGS. 12 and 13.

The care unit 210a includes, as shown in FIGS. 12 and 13, the four sharing function modules which are a note module 211, a record module 212, a hearing module 213 and a book module 214. These modules 211, 212, 213 and 214 are provided for various applications 220 which provide additional medical services associated with various types of care (treatment) such as medication management, lifestyle improvement, diabetes medication support, team medical support, pressure ulcer care and rehabilitation support, and are prepared as means for facilitating the development of the applications 220. These modules 211, 212, 213 and 214 are shared in all the applications 220 which are developed for the care unit 210a.

In other words, it is possible to obtain applications 220 which provide desired new services by combining these modules 211, 212, 213 and 214 as necessary. For example, when it is desired to perform a medical interview with a patient on a symptom, a medication condition, eating habits, and the like, settings are made such that the hearing module 213 is used, the details of a question group used in the medical interview are sequentially set within the module 213 and thus it is possible to easily develop the question group for the medical interview. Specifically, for example, as targets of questions, it is possible to easily set, for example, to whom questions are asked, what questions are asked, and what the question targets are. The same is true for answers to the question group. For example, it is possible to easily set the point of whether answers are received in a multiple-choice form or in a comment or message form. Furthermore, it is possible to likewise set the point of whom the question group is presented to and at what time (timing) the question group is presented, the point of the range of disclosure of the question group and the point of the range of answers.

The note module 211 is a module for providing, to the developer D, the function of recording desired information in a predetermined storage means (specifically, the application storage unit 332 of the medical support system 30) each time the user of the medical support system 30 needs the function. This function enables the same operation as an operation in which the user (for example, the medical worker M) of the medical support system 30 (medical support service) records desired information in a notebook as necessary. In a specific example, when this function is described within the application 220, it is possible to easily realize an operation in which at the time of the execution thereof, for example, a specific medical worker M is prompted to input details corresponding to the settings of the function: "complications, other symptoms" shown in FIG. 25 on the timeline (medical worker side) of the group G to which the medical worker M belongs and in which when the details are input, the details of the input are automatically stored in the application storage unit 332 (this is executed in a "user settings process" which will be described later). Then, in the application 220, a message posting (display) function of the medical support system 30 on the timeline is used, and thus it is possible to very easily realize an operation of posting and displaying, at a desired time, the headline: "complications, other symptoms" and the details of the input (that is, details set in the "user settings process") on the timeline (patient side) of the group G.

Since an initial settings is needed in order to use the function of the note module 211 incorporated into the application 220, at the time of the start of use, the predetermined initial settings is executed in a "manager settings process" performed by the system manager A in the medical support system 30. A settings change (this settings change is generally performed by a request or an instruction from the user, for example, the medical worker M) which is performed as necessary after the start of use of the function is also executed in the "manager settings process" performed by the manager A. Here, the user (for example, the medical worker M) who desires the settings change requests the settings change of the system manager A, and the manager A who receives the request executes the "manager settings process" again so as to perform the settings change desired by the requester.

Here, the "timeline (medical worker side)" can be browsed only by the medical worker M among the group members, and corresponds to the medical worker shared area 51b of FIG. 9. The "timeline (patient side)" can be browsed by all the group members, and corresponds to the shared area for all members 51a of FIG. 9. This is true in the following description.

The record module 212 is a module for providing, to the developer D, the function of automatically capturing predetermined information (external information) provided from the outside and recording it in a predetermined storage means (specifically, the application storage unit 332 of the medical support system 30). This function enables an operation in which predetermined external information (for example, various types of inspection information sent from an inspection agency) necessary for the user (for example, the medical worker M) of the medical support system 30, is automatically collected at the desired timing and is recorded within the medical support system 30. In a specific example, when this function is described within the application 220, it is possible to easily realize an operation in which at the time of the execution thereof, for example, information (inspection information) related to an inspection item specified in the function settings: "inspection record" shown in FIG. 25, is read from a predetermined information source (for example, a database) which is externally present and is automatically stored in the application storage unit 332 (the specifications of the inspection item are executed in the "user settings process" which will be described later). Then, in the application 220, the message posting function of the medical support system 30 is used, and thus it is possible to very easily realize an operation of posting and displaying, at a desired time, the headline: "inspection record" and the corresponding inspection information on the timeline (medical worker side) of the group G. As the inspection information, for example, vital signs are present which are the most basic information regarding the life of the specified patient P. The vital signs often indicate, for example, the four items of pulse or heart rate, respiration (number), blood pressure and body temperature, and the current condition of the patient P can be grasped and expressed from the numerical information thereof. Items such as weight, blood pressure, blood sugar level and HbA1c, which are included in diagnoses performed before and after treatment or in the middle thereof, apply thereto. It is needless to say that external information other than the inspection information described above can be likewise captured and recorded.

Since initial settings are needed as in the case of the note module 211 in order to use the function of the record module 212 incorporated into the application 220, at the time of the start of use, the predetermined initial settings are executed in the "manager settings process" performed by the system manager A. The settings change which is performed as necessary after the start of use of the function is also executed in the "manager settings process" performed by the manager A.

The hearing module 213 is a module for providing, to the developer D, a function for conducting a series of questions and answers (for example, a medical interview with a patient) on a predetermined target person. This function enables an operation in which the user (for example, the medical worker M) of the medical support system 30 asks the predetermined target person (for example, the patient P) a series of questions at the desired timing, and in which thus desired information (for example, information on the recent condition and symptoms of the patient P) corresponding to the questions is acquired as answers and is recorded. Hence, in the hearing module 213, a series of question samples (question template group) and a series of answer samples (answer template group) are prepared, the template groups are utilized and thus it is possible to simply make desired question sentences and answer forms suitable therefor. In a specific example, when the function of the hearing module 213 is described within the application 220, it is possible to easily realize an operation in which at the time of the execution thereof, for example, in the function settings: "confirmation of symptoms causing anxiety", "confirmation of eating habits", and the like shown in FIG. 25, based on the question group (question template group) previously prepared according to the titles thereof, desired question sentences are automatically produced, in which the question sentences (question information) are posted on the timeline (patient side) of the group G to which the patient P serving as the target person belongs with the message posting function of the medical support system 30 at the desired timing, and in which the patient P is prompted to give answers. Then, it is possible to easily realize an operation in which when answers are input from the patient P, a function of the medical support system 30 is used so as to automatically store the details of the answers (answer information) in the application storage unit 332. The specifications of the question information and the specifications of the answer form for the answer information are executed in the "user settings process" which will be described later.

Since initial settings are needed as in the cases of the note module 211 and the record module 212 in order to use the function of the hearing module 213 incorporated into the application 220, at the time of the start of use, the predetermined initial settings are executed in the "manager settings process" performed by the system manager A. The settings change which is performed after the start of use of the function is also executed as necessary in the "manager settings process" performed by the manager A.

The book module 214 is a module for providing, to the developer D, the function of storing, in a file format, various types of information as "contents" in a predetermined storage means (specifically, the application storage unit 332). This function can easily realize an operation in which files of various formats (for example, pdf, xls, doc, jpg and mp4) where useful information (beneficial information) for a specific user (for example, the patient P, the medical worker M or the patient-related person R) of the medical support system 30 is organized as the "contents" and previously stored in which the message posting function of the medical support system 30 is used, and in which thus the specified contents are posted and displayed at the desired timing on the timeline (patient side) of the specific group G. In a specific example, when this function is described within the application 220, it is possible to easily realize an operation in which at the time of the execution thereof, for example, in the function settings of "diabetes advice (diet)", "diabetes advice (exercise)" and the like shown in FIG. 25, the message posting function of the medical support system 30 is used so as to post and display, at the desired timing, contents (files) previously prepared according to the titles thereof on the timeline (patient side) of the group G to which the patient P serving as the target person belongs. In this way, for example, the patient P or the patient-related person R can easily acquire beneficial information with optimal timing. The preparation, the storage, and the specifications of the contents (files) are executed in the "user settings process" which will be described later.

Since initial settings are needed as in the cases of the note module 211, the record module 212 and the hearing module 213 in order to use the function of the book module 214 incorporated into the application 220, at the time of the start of use, the predetermined initial settings are executed in the "manager settings process" performed by the system manager A. The settings change which is performed after the start of use of the function is also executed as necessary in the "manager settings process" performed by the manager A.

Although here, each of the note module 211, the record module 212, the hearing module 213 and the book module 214 described above is realized with a bot (BOT) which automatically executes, when receiving a predetermined instruction or request from any one of the applications 220, a predetermined program, the present invention is not limited to this configuration. Any automatic execution program can be utilized which automatically executes a predetermined function, in a state where the program is independent from the medical support system 30 serving as the platform, according to an instruction or request sent from the application 220 or the medical support system 30. The automatic execution program may be software or may be written in hardware. As long as the program can provide the specific; function of each of the modules 211, 212, 213 and 214, the program can be sufficiently used.

The care unit 210a described above includes a basic function unit 215 in addition to the sharing function modules 211, 212, 213 and 214 described above.

The basic function unit 215 is a section which executes a basic function of the care unit 210a other than the specific functions of the four function modules 211, 212, 213 and 214 described above. For example, the basic function unit 215 executes: processing necessary for utilizing the specific function of the module 211, 212, 213 or 214 from the developer terminal 13 with the application 220; and processing necessary for calling and using the specific function of the module 211, 212, 213 or 214 within the application 220. When the application 220 is developed, the basic function unit 215 executes processing necessary for cooperation between the modules 211, 212, 213 and 214 (the application framework 200), the medical support system 30 and the developer terminal 13, whereas when the application 220 is utilized, the basic function unit 215 executes predetermined processing necessary for cooperation between the modules 211, 212, 2.13 and 214 (the application framework 200), the medical support system 30 and the user terminal 10, 11 or 12 (that is, the application 220).

(Configuration of Service Architecture Support System)

The configuration of the service architecture support system 100 according to the embodiment of the present invention will be described next with reference to FIGS. 14 and 15. The service architecture support system 100 generates application framework 200 having the configuration described above on the medical support system 30, and realizes cooperation between the application framework 200 and the medical support system 30 so as to realize the enhanced efficiency of the development of the application 220 and the facilitation of the construction of a new medical service (additional service) in the medical support system 30.

As long as the service architecture support system 100 can perform an operation in cooperation with the medical support system 30, there is no limitation to the configuration thereof. In other words, the system 100 may be configured (arranged) within the medical support system 30 integrally therewith or may be configured (arranged) outside the medical support system 30 separately therefrom. The service architecture support system 100 may be configured (arranged) within a server device (not shown) in which the medical support system 30 is incorporated together therewith or may be configured (arranged) In a server device separate from the server device in which the medical support system 30 is incorporated so as to communicate therewith through the Internet 20 or another network.

As shown in FIGS. 14 and 15, the service architecture support system 100 includes four sections which are an application management unit 110, a unit management unit 120, a module management unit 130 and a framework management unit 140, and is operated in cooperation with the medical support system 30.

The application management unit 110 is a section which manages the application 220 that utilizes the application framework 200 generated with the service architecture support system 100 and the developer D thereof. In other words, the service architecture support system 100 registers (application registration) the application 220 developed by utilization of the application framework 200, registers (developer registration) the developer D of the application 220 and manages information related to the application 220 and the developer D which are registered as described above. Since here, the developer D cannot perform the developer registration without being a user of the medical support system 30, the developer D first performs user registration in the medical support system 30 and thereafter performs the developer registration. This is because an application development applicant (for example, an engineer who belongs to a pharmaceutical company, a hospital or the like or who receives a commission therefrom) develops the application 220 for utilizing the function of the system 30 so as to provide a highly advanced medical service as compared with the medical service provided by the medical support system 30. Hence, the application development applicant performs a two-stage registration procedure so as to first perform the user registration in the medical support system 30 and to thereafter perform the developer registration. The application management unit 110 having the functions as described above includes a registration unit 111 and an application information storage unit 112.

The registration unit 111 is formed with software for controlling the operation thereof, and controls the overall operation of the user registration in the application management unit 110, the developer registration, and the application registration; as well as an operation related to the execution of the application 220 installed into the medical support system 30 after the application registration. For example, the registration unit 111 is on standby for an application development request from the developer D (application development applicant) who wants to develop the application 220 by utilization of the application framework 200, displays a predetermined user registration screen (not shown) on the developer terminal 13 of the developer D when receiving the request and prompts the developer D to input predetermined personal information so as to perform the user registration in the medical support system 30. When the predetermined personal information is transmitted from the developer terminal 13 to the service architecture support system 100 accordingly, the personal information is stored in the application information storage unit 112 as "user information" and "developer information" related to the developer D. In this way, the user registration and the developer registration are completed. Then, the registration unit 111 displays a predetermined application registration screen (not shown) on the developer terminal 13, and prompts the developer D to input predetermined application information (for example, the name, the application, and the purpose of the application) so as to perform the application registration. When the predetermined application information is transmitted from the developer terminal 13 to the service architecture support system 100 accordingly, the application information is stored in the application information storage unit 112 as "application information" related to the developer D. In this way, the application registration is completed.

The developer D who completes the user registration, the developer registration and the application registration utilizes the application framework 200 so as to develop the desired application 220. Which one of the care unit 210a and the community unit 210b provided in the application framework 200 is used is automatically determined according to the application and the purpose of the application 220. For example, when the application 220 is intended for (applied to) diabetes medication support, the utilization of the care unit 210a is automatically determined, and thus the developer D utilizes the four specific functions provided by the note module 211, the record module 212, the hearing module 213 and the book module 214 provided in the care unit 210a so as to develop the application 220 of the developer D. On the other hand, for example, when the application 220 is intended for (applied to) coordination which functions as cooperation windows between multi-professional workers, the utilization of the community unit 210b is automatically determined, and thus the developer D utilizes a plurality of specific functions provided by a module group (not shown) provided in the care unit 210b so as to develop the application 220 of the developer D.

When the developer D, who completes the user registration, the developer registration and the application registration, wants to utilize the application framework 200 so as to upload the application 220 (in which the application registration has been performed) developed by the developer D into the service architecture support system 100 (medical support system 30), a request (upload request) indicating the information thereof is transmitted to the system 100. When the registration unit 111 receives the upload request, the registration unit 111 displays a predetermined upload screen (not shown) on the developer terminal 13 of the developer D, and prompts the developer D to upload the newly developed application 220. When the new application 220 (application configuration file) is uploaded from the developer terminal 13 into the service architecture support system 100 accordingly, the registration unit 111 stores the new application 220 (application configuration file) in the application storage unit 332 of the medical support system 30, performs predetermined processing so as to incorporate (install) the new application into the medical support system 30 and allows the new application to be utilized. In this way, the upload/incorporation processing of the new application 220 is completed.

The registration unit 111 also executes, as necessary, for example, operations in which the "user information", the "developer information" and the "application information" stored in the application information storage unit 112 are read and utilized, corrected and deleted.

The application information storage unit 112 is formed with: an information storage medium such as a hard disk; and software which controls operations of recording, reproduction, deletion, and the like of information on the information storage medium, and stores the "user information", the "developer information" and the "application information" described above and other necessary information (such as the purpose and application of the application).

The registration of the "user information", the "developer information" and the "application information" described above is performed with, for example, the user table of FIG. 16(a), the developer table of FIG. 16(b), the developer affiliate organization table of FIG. 16(c) and the application table of FIG. 16(d).

In this case, at the time of the user registration, a user ID assigned to the application development applicant and associated information such as a password are stored in the user table as shown in FIG. 16(a). This user table is the same as that shown in FIG. 4(a) except that the information of the developer D is newly added.

At the time of the developer registration, developer identification information (developer ID) assigned to the application development applicant, and the associated information thereof, as well as the affiliate organization identification information (affiliate organization ID) assigned to the organization to which the application development applicant belongs and the associated information thereof, are respectively stored in the developer table of FIG. 16(b) and in the developer affiliate organization table of FIG. 16(c).

In this case, at the time of the application registration, application identification information (application ID) assigned to the application 220, the developer ID of the developer who develops it, the group ID of the group G which can utilize the application, a date (registration date) on which the application is registered, and information indicating whether or not the application can be utilized and in which group G the application can be utilized (status information), are stored in the application table of FIG. 16(d). Since at the time of the application registration, the development of the application is not completed, the status information is stored so as to be "disabled". Then, when the application is uploaded and installed so as to be able to be utilized in the medical support system 30, the status information is rewritten from "disabled" to "enabled".

In the application registration, it is important that individual application IDs be stored so as to be associated with a plurality of group IDs. Specifically, in the application table of FIG. 16(d), the application 220 (application 1) having an application ID of "1" is associated with two group IDs "10003" and "10004", and the application 220 (application 2) having an application ID of "2" is associated with two group IDs "10003" and "10005". This means that the application 1 is enabled (can be executed) in the two groups G having the group IDs "10003" and "10004", and that the application 2 is enabled (can be executed) in the two groups G having the group IDs "10003" and "10005". When this is considered from the side of the group G having the group ID "10003", the two applications 1 and 2 are simultaneously enabled (can be executed), and in other words, group members (the medical worker M, the patient P or the patient-related person R) belonging to the group G having the group ID "10003" can selectively utilize the applications 1 and 2, and can also utilize both the applications 1 and 2 in parallel. Hence, the group members belonging to the group G having the group ID "10003" use the one user ID such that they can utilize the application 1 and thereafter utilize the application 2, and can utilize the application 2 and thereafter utilize the application 1. Since, as will be described later, it is possible to start and stop the utilization of the applications 1 and 2 only by providing an instruction to start or stop the utilization on the timeline of the group G, the group members in the group G do not need to repeatedly log out of and log in to the medical support system 30 each time the utilized application is changed, with the result that this configuration is advantageous in that the psychological barrier to the development of the application and the utilization thereof is low.

Although the user table shown in FIG. 16(a) is stored in the application storage unit 332 of the medical support, system 30, this is a copy of the user table shown in FIG. 4(a) (this is stored in the user information storage unit 312 of the medical support system 30). Both the tables are synchronous with each other such that pieces of information within both the tables constantly agree with each other. The developer table shown in FIG. 16(b), the developer affiliate organization table shown in FIG. 16(c) and the application table shown in FIG. 16(d) are also stored in the application storage unit 332.

Although in the embodiment, the application registration is performed at the same time as the user registration and the developer registration, the present invention is not limited to this configuration. A configuration may be adopted in which the application registration is not performed when the user registration and the developer registration are performed, and in which in a stage where after the completion of the application 220, the application 220 is uploaded and incorporated (installed) into the medical support system 30, the application registration is performed. It is needless to say that it is possible to add or delete a group G which can utilize the application 220 after the application registration is performed (that is, which has a group ID associated with the registered application ID).

The unit management unit 320 will be described next.

The unit management unit 120 is a section which controls the care unit 210a and the community unit 210b provided in the service architecture support system 100. For example, the unit management unit 120 executes various types of functions such as the control of the functions (unit functions) of both the units 210a and 210b, the control of the interface, the control of mutual access between both the units 210a and 210b and the developer terminal 13 or the user terminal 10, 11 or 12, the new registration of a new unit, the deletion of the unit 210a or 210b, and the change of the details thereof. The unit management unit 120 having the functions as described above includes a registration unit 121 and a function control unit 122.

The registration unit 121 is formed with software for controlling the operation thereof and an information storage means such a hard disk, and performs processing for producing a new unit and additionally registering it, processing for deleting the existing unit 210a or 210b, processing for correcting registration information related to the existing unit 210a or 210b and the like. The information related to the registered units 210a and 210b is stored in a storage region within the registration unit 121. When a new unit is newly registered, the registration unit 121 stores, in the storage region, unit information, that is, information indicating to which genre (such as care, community or side effect management) the unit belongs and what function module the unit has. Since the total number of units is not limited, it is possible to produce the necessary number of units.

The function control unit 122 is formed with software for controlling the operation thereof, and controls functions (unit functions) which are provided to the care unit 210a and the community unit 210b. Specifically, the function control unit 122 performs, for example, mutual access control between the units 210a and 210b provided within the application framework 200 and the developer terminal 13 or the user terminal 10, 11 or 12, and allows a specific function provided by the unit 210a or 210b to be utilized from the developer terminal 13 or the user terminal 10, 11 or 12 (the application 220).

The module management unit 130 will be described next. Here, only the four function modules 211, 212, 213 and 214 provided within the care unit 210a will be described, and the description of function modules within the community unit 210b will be omitted.

The module management unit 130 is a section which manages a function module group provided within each the care unit 210a and the community unit 210b. The module management unit 130 manages the operations of the note module 211, the record module 212, the hearing module 213 and the book module 214 in the care unit 210a and the module group (not shown) in the community unit 210b and the usage situations thereof. The module management unit 130 having the functions as described above includes a note module control unit 131, a record module control unit 132, a hearing module control unit 133, a book module control unit 134 and a registration unit 135.

The note module control unit 131 is formed with software which controls the operation of the note module 211 within the application framework 200. At the time of the application development, according to a request, from the developer terminal 13, the note module control unit 131 displays, on the developer terminal 13, for example, a predetermined note module usage screen (not shown) or displays, on the developer terminal 13, a screen (not shown) which specifies, for example, information to be recorded, timing with which to be recorded, a person to be recorded, the title of the information and the like such that the function of: "recording desired information as necessary, as recorded in a notebook" prepared in the note module 211 can be easily utilized. Since at the time of utilization of the application, the function of the note module 211 is incorporated into the application 220 developed with the developer terminal 13, in accordance with the description of the application 220, for example, with specified timing, the note module control unit 131 prompts the person to be recorded to input specified information on the screen of the user terminal 10, 11 or 12 of the person to be recorded, displays the information input and recorded in this way as necessary on the screen of the user terminal 10, 11 or 12 of a specified person and records (stores) the input information in a specified place (for example, the application storage unit 332).

The record module control unit 132 is formed with software which controls the operation of the record module 212 within the application framework 200. At the time of the application development, according to a request from the developer terminal 13, the record module control unit 132 displays, on the developer terminal 13, for example, a predetermined record module usage screen (not shown) or displays, on the developer terminal 13, a screen (not shown) which specifies, for example, information to be automatically collected and recorded, timing, an information source, a storage destination, the title thereof and the like, such that the function of: "automatically collecting and recording necessary external information (for example, inspection information) at the desired timing" prepared in the record module 212 can be easily utilized. Since at the time of utilization of the application, the function of the note module 211 is incorporated into the application 220 developed with the developer terminal 13, in accordance with the description of the application 220, for example, the record module control unit 132 automatically collects information specified from the specified information source with specified timing and records (stores) the information in a specified place (for example, the application storage unit 332).

The hearing module control unit 133 is formed with software which controls the operation of the hearing module 213 within the application framework 200. At the time of the application development, according to a request from the developer terminal 13, the hearing module control unit 133 displays, on the developer terminal 13, for example, a predetermined hearing module usage screen (not shown) or displays, on the developer terminal 13, a question production screen (not shown), for example, for specifying a question template to be used, specifying a correction to be made in the question template, specifying a person for whom the produced questions and the title thereof need to be displayed and specifying a person who needs to answer the produced questions, an answer form, and the like, such that the function of: "asking a predetermined target person a series of questions (for example, a medical interview)" prepared in the hearing module 213 can be easily utilized. Since at the time of utilization of the application, the function of the hearing module 213 is incorporated into the application 220 developed with the developer terminal 13, in accordance with the description of the application 220, for example, the hearing module control unit 133 displays the produced questions on the screen of the user terminal 10, 11 or 12 of the specified person, and records (stores) answers input for the displayed questions in a specified place (for example, the application storage unit 332).

The book module control unit 134 is formed with software which controls the operation of the book module 214 within the application framework 200. At the time of the application development, according to a request from the developer terminal 13, the book module control unit 134 displays, on the developer terminal 13, for example, a predetermined book module usage screen (not shown) or displays, on the developer terminal 13, for example, a screen for specifying on whose user terminal 10, 11 or 12 a file specifications screen specifying a file to be stored as "contents" and the title thereof is displayed such that the function of: "storing various types of information in a file format as contents" prepared in the book module 214 can be easily utilized. Since at the time of utilization of the application, the function of the book module 214 is incorporated into the application 220 developed with the developer terminal 13, in accordance with the description of the application 220, for example, the book module control unit 134 displays a predetermined file specifications screen on the specified user terminal 10, 11 or 12, displays contents included in the file specified on the file specifications screen as necessary on the specified user terminal 10, 11 or 12 and records (stores) an uploaded content file in a specified place (for example, the application storage unit 332).

The registration unit 135 is formed with software for controlling the operation thereof and an information storage means such a hard disk, and performs processing for producing a new module and additionally registering it for each of the units 210a and 210b, processing for deleting the four: existing modules 131, 132, 133 and 134 prepared in the unit 210a and existing modules (not shown) prepared in the unit 210b, processing for correcting registration information related to the existing modules and the like. The information related to the existing modules 211, 212, 213 and 214 within the registered unit 210a and the existing modules within the unit 210b is stored in a storage region within the registration unit 135. When a new module is newly registered, the registration unit 135 stores, in the storage region, module information, that is, information indicating what function the module has and for what purpose the module is used. Since the total number of modules within the unit is not limited, it is possible to produce the necessary number thereof.

The framework management unit 140 is formed with: software for controlling the operations of the application management unit 110, the unit management unit 120 and the module management unit 130; and an information storage means such as a hard disk. The framework management unit 140 manages the overall operation of the application framework 200, stores information related to cooperation between the application management unit 110, the unit management unit 120 and the module management unit 130 installed within the application framework 200 and uses the information thereof so as to achieve the predetermined function of the application framework 200.

(Operation of Service Architecture Support System)

The operation of the service architecture support system 100 of the present embodiment having the configuration described above will be described next with reference to the flowcharts of FIGS. 48 and 49.

(At Time of Application Development)

In the present embodiment, the developer D (application development applicant) who wants to develop, by utilization of the application framework 200, the application 220 operated on the medical support system 30, accesses the service architecture support system 100 from the developer terminal 13 of the developer D through the Internet 20, and transmits a request indicating the information thereof, that is, the "application development request" to the system 100. Hence, as shown in FIG. 48, the service architecture support system 100 is constantly on standby for the reception of the application development request sent from the developer terminal 13 (step S1).

When the service architecture support system 100 receives the application development request, the registration unit 111 of the application management unit 110 displays a predetermined user registration screen (not shown) on the developer terminal 13 of the developer D to which the request is transmitted, and prompts the developer D to input predetermined personal information so as to first perform the user registration in the medical support system 30 (step S2). When the predetermined personal information is transmitted from the developer terminal 13 to the service architecture support system 100 accordingly, the personal information is stored in the application information storage unit 112 as "user information" and "developer information" related to the developer D. In this way, the user registration and the developer registration are completed (step S3). The information stored in the user registration and the developer registration is, for example, as described in the user table, the developer table and the developer affiliate organization table of FIGS. 16(a), 16(b) and 16(c).

Then, the registration unit 111 displays a predetermined application registration screen (not shown) on the developer terminal 13, and prompts the developer D to input predetermined application information so as to perform the application registration (step S4). When the predetermined application information is transmitted from the developer terminal 13 to the service architecture support system 100 accordingly, the application information is stored in the application information storage unit 112 as "application information" related to the developer D. In this way, the application registration is completed (step S5). Thereafter, the service architecture support system 100 is on standby for the transmission of the upload request for the new application 220 from the developer terminal 13 after the completion of the development (step S6). The information stored in the application registration is, for example, as described in the application table of FIG. 16(d).

When the user registration, the developer registration and the application registration are completed as described above, the function of the application framework 200 can be utilized, and thus the developer D described above accesses the application framework 200 from the developer terminal 13 of the developer D, utilizes the function of the unit of the genre to which the application 220 to be developed belongs, for example, the care unit 210a, and thereby can efficiently develop the new application 220. In other words, the developer D incorporates, into the new application 220, as necessary, the functions of the note module 212, the record module 212, the hearing module 213 and the book module 214 prepared in the care unit 210a, and thus it is possible to significantly simplify the description related to the functions provided by the modules 211, 212, 213 and 214, with the result that it is possible to highly efficiently develop the new application 220.

Specifically, the new application 220 describes: a point (a) i.e., in which order the specific functions of the four modules 211, 212, 213 and 214 are combined and how they are combined together to produce desired question information and presentation information in order to achieve the purpose thereof (for example, diabetes medication support); and a point (b) i.e., what information is specified and added (for example, the name of a medicine used in the questions and the intake thereof, inspection items collected and recorded and titles provided for the individual items) when the specific functions of the modules 211, 212, 213 and 214 are practiced, of whom the specifications and addition of the information are requested (for example, which one of the system manager A and a specific user), on which timeline the question information and the presentation Information produced in this way are posted (displayed), in what order they are posted (displayed) and with what timing they are posted (displayed), and thereby can significantly reduce parts described in the application 220 with a program language. Here, "question information" refers to information which includes any question to a specific user, and "presentation information" refers to information which includes information such as any message presented to a specific user and which does not include any questions.

When the developer D who completes the user registration and the developer registration wants to upload, by utilization of the application framework 200, the new application 220 (in which the application registration has been performed) developed by the developer D, it is necessary to send a request (upload request) indicating the information thereof to the service architecture support system 100. When the system 100 receives the upload request, the registration unit 111 displays a predetermined upload screen (not shown) on the developer terminal 13 of the developer D, and prompts the developer D to upload the new application 220 (step S7). When the file of the new application 220 (application configuration file) is uploaded from the developer terminal 13 into the service architecture support system 100 accordingly, the registration unit 111 stores the data of the new application 220 in the application storage unit 332 of the medical support, system 30, performs predetermined installation processing so as to incorporate the new application into the medical support system 30 and allows the new application to be utilized on the system 30 (step S8). In this way, the upload/incorporation processing of the new application 220 is completed. A group member who belongs to one or a plurality of groups G with which the new application 220 is associated can utilize the new application 220 which was incorporated into the medical support system 30 in this way from the user terminal 10, 11 or 12 of the group member any time after the necessary "manager settings process" and "user settings process" are executed so as to complete the necessary initial settings.

The new service provided by the new application 220 incorporated into the medical support system 30 in this way is registered in the medical support system 30 as an additional medical service (additional service) to the existing medical services provided within the medical support system 30 by the system 30 or as an optional service. Thereafter, the user (the patient P, the patient-related person R or the medical worker M) of the medical support system 30 can utilize the additional service (new service) any time from the user terminal 10, 11 or 12 of the user according to the desire of the user or stop the utilization.

(At Time of Utilization of Application)

Figure 48:
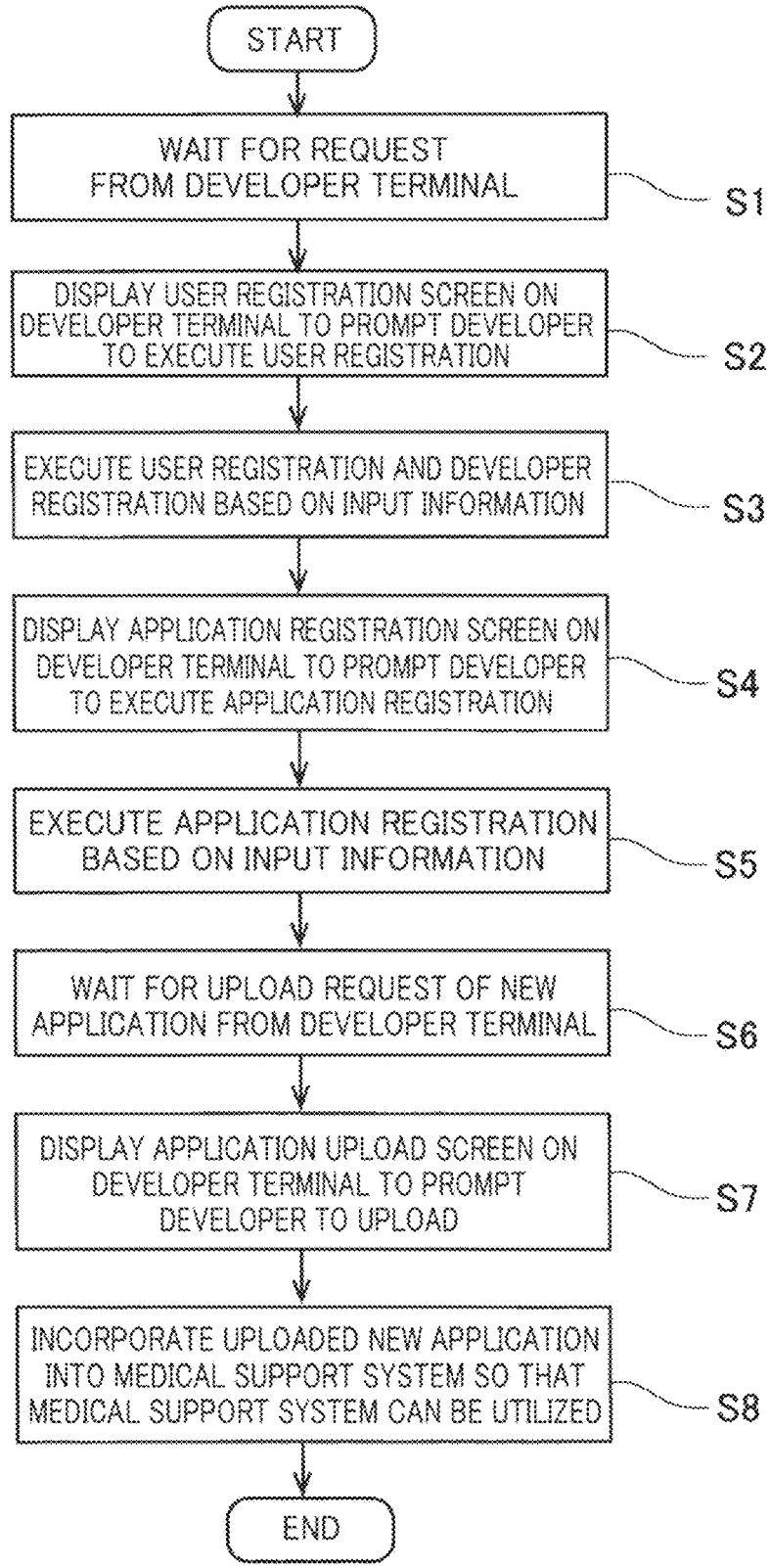
FIG. 48 is a flowchart showing an operation when the application of the service architecture support system according to the embodiment of the present invention is developed.
Figure 49:
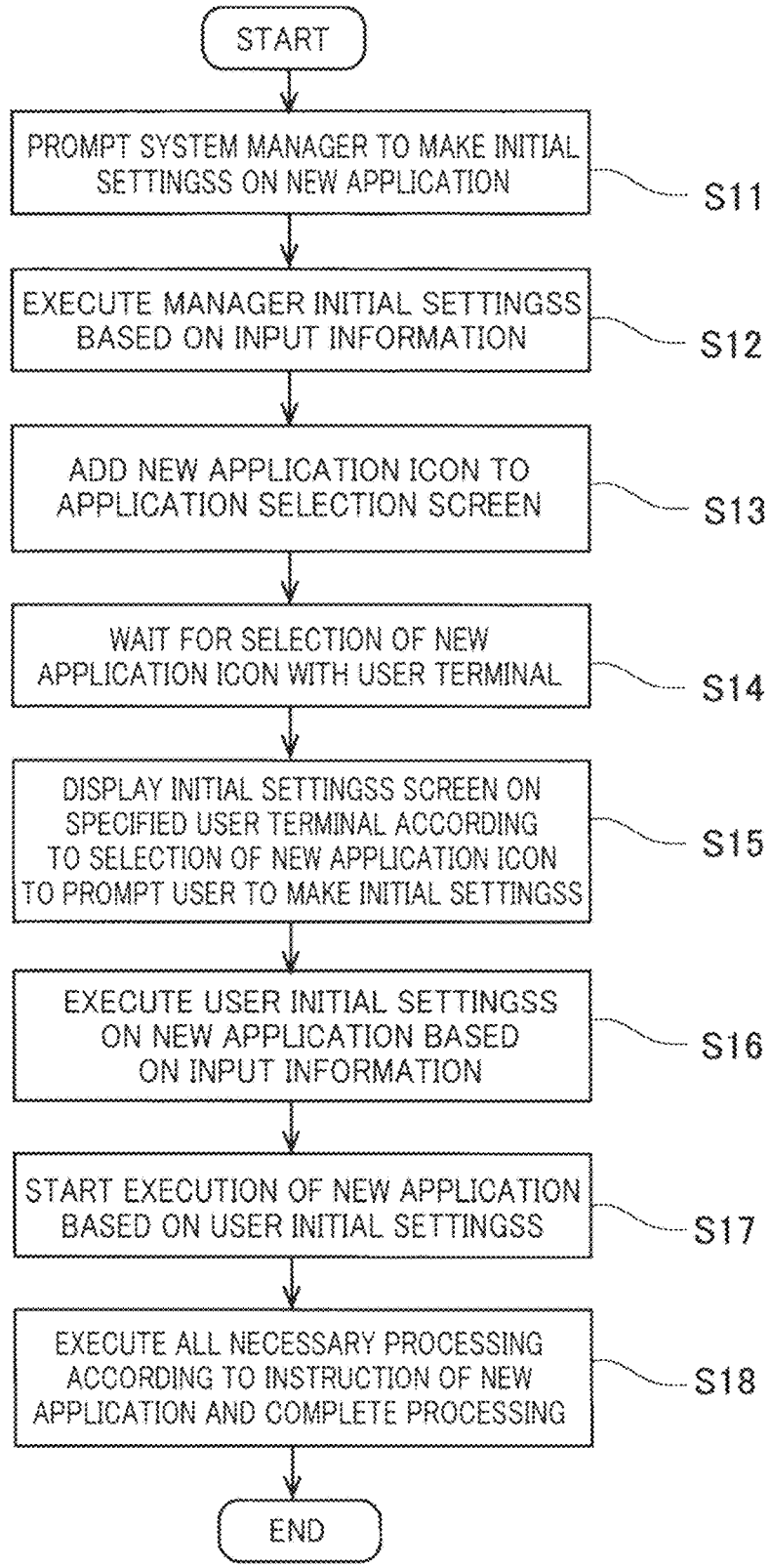
FIG. 49 is a flowchart showing an operation when the application of the service architecture support system according to the embodiment of the present invention is utilized.

When in step S8 of FIG. 48, the processing which incorporates the new application 220 into the medical support system 30 is completed, the registration unit 111 of the application management unit 110 in the service architecture support system 100 displays, as shown in FIG. 49, a predetermined initial settings screen (see, for example, FIGS. 23 to 35) on the manager terminal 14 (see FIG. 1) of the system manager A in the medical support system 30 so as to prompt the system manager A to perform the initial settings on the new application 220 which was incorporated (step S11). This is a first-stage initial settings on the new application 220 which is performed in the "manager settings process" by the system manager A. When the system manager A makes the necessary settings with the manager terminal 14 so as to execute a predetermined "manager settings process" accordingly, the registration unit 111 performs, based on the details of the settings, the "manager settings (manager initial settings)" on the four modules 211, 212, 213 and 214 incorporated into the new application 220 (step S12). Furthermore, the registration unit 111 adds an icon (new application icon) indicating the new application 220 to a predetermined application selection screen (see, for example, FIGS. 19, 20 and 22) (step S13). Thereafter, the registration unit 111 is on standby for the selection of the new application icon with the user terminal 10, 11 or 12, that is, the arrival of a request of utilization of the new service provided by the new application 220 (step S14).

When the request for utilization of the new service provided by the new application 220 which can be utilized in this way arrives from any of the users, the registration unit 111 displays an initial settings screen (see, for example, FIGS. 46 and 47) on the user terminal 10, 11 or 12 specified in the new application 220 so as to prompt the specified user to make the initial settings on the new application 220 which was incorporated (step S15). These are the second-stage initial settings on the new application 220 which are performed in the "user settings process" by the specified user. When the specified user inputs the necessary information and makes the necessary settings with the user terminal 10, 11 or 12 of the specified user so as to execute the "user settings process" accordingly, the registration unit 111 performs, based on the details of the settings, the "user settings (user initial settings)" on the four modules 211, 212, 213 and 214 incorporated into the new application 220 (step S16). When the "manager initial settings" and the "user initial settings" are completed in this way, the new application 220 can be executed based on the details of the settings, and thus the registration unit 111 starts the execution of the new application 220. In other words, the provision of the new service by the new application 220 to the specified user is started (step S17).

When the execution of the application 220 (provision of the new service) is started in this way, a series of processing steps such as a step in which predetermined question information and presentation information are posted and displayed on the timeline of the group G to which the user receiving the request of utilization of the new service on the new service belongs, and a step in which answer information posted by the specified user of the group G on the timeline is stored, are sequentially executed according to instructions from the new application 220 that is being executed. When all the processing steps are executed in this way, the operation of the new application 220 is completed (step S18). As described above, the new service (additional service) is provided to the specified user belonging to the group G while the application 220 is being executed.

For example, by means of the new application 220, the predetermined question information and presentation information are sequentially posted and displayed on the timeline of the group G according to a predetermined schedule, and thus it is possible to report predetermined information (for example, a possible complications and other symptoms and an inspection result) to the patient P and the patient-related person R serving as specified users at the desired timing. When the patient P or the patient-related person R related to the group provides answer information in relation to the question information (for example, confirmation of symptoms causing anxiety, eating habits and remaining medicine) posted on the timeline, the answer information is posted and displayed on the timeline and is stored simultaneously and automatically, with the result that the medical worker M of the group G can confirm the answer information. Consequently, various new services (for example, a medication support service) can be easily constructed and additionally provided to the existing medical services provided with the medical support system 30, and it is also possible to effectively utilize the feature of the system 30 in the new services, that is, the feature "in which one or a plurality of users of a medical service (including not only a patient, but also a medical worker) are selectively made to belong, as group members, to a group generated for each target person (patient) of the medical service, in which only the group members are allowed to browse medical information on the target person related to the group and in which thus the medical information related to the target person can be shared among the group members while ensuring the privacy of the target person".

(Form of Utilization of New Service Provided by Application)

A specific example of the form of utilization of the additional service provided by the new application 220 as described above will be described next with reference to FIGS. 17 to 47.

Figure 17:
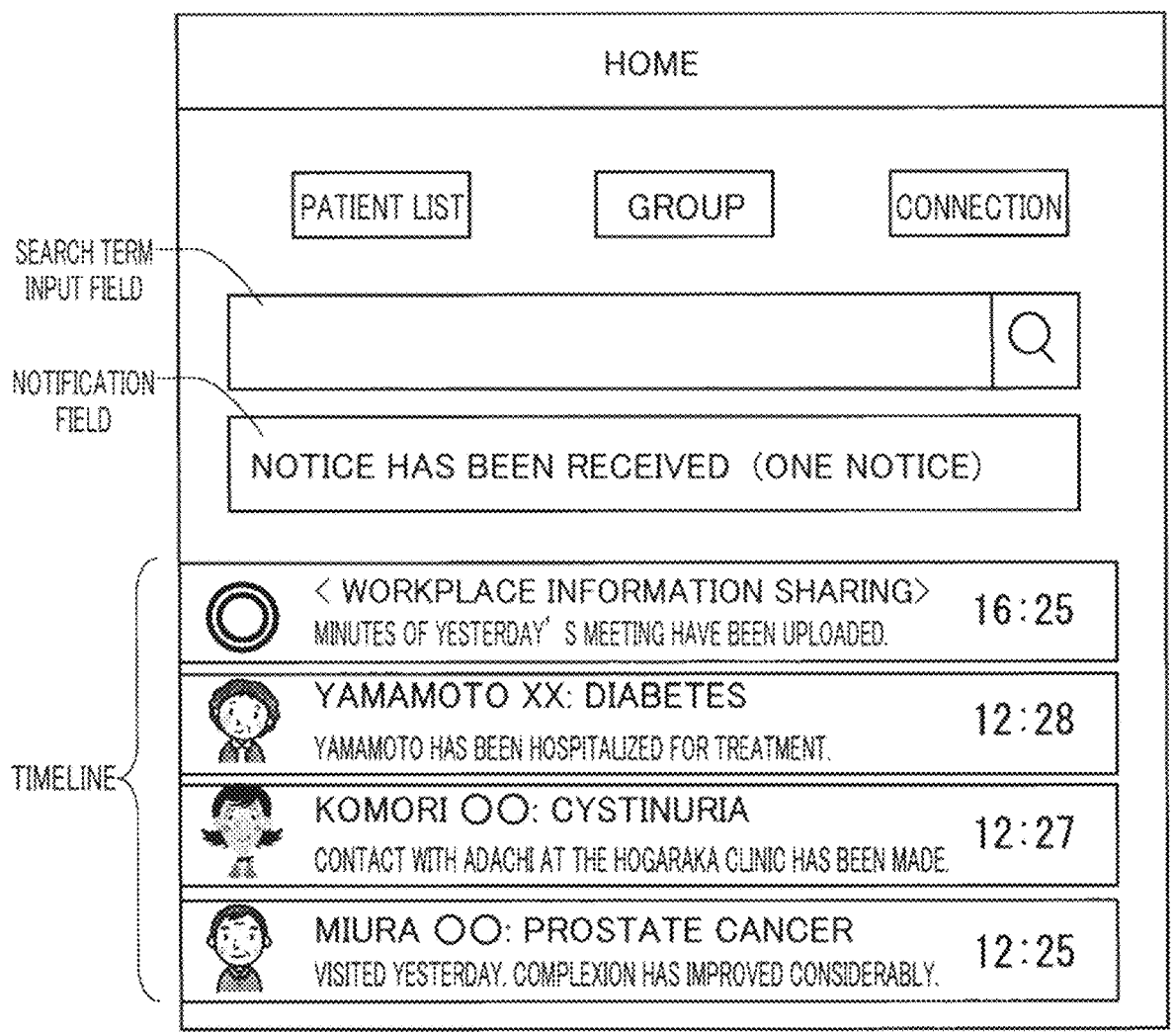
FIG. 17 is an illustrative view showing an example of a "home screen" of a specific patient when an application is installed in the medical support system in which the service architecture support system according to the embodiment of the present invention is incorporated.
Figure 18:
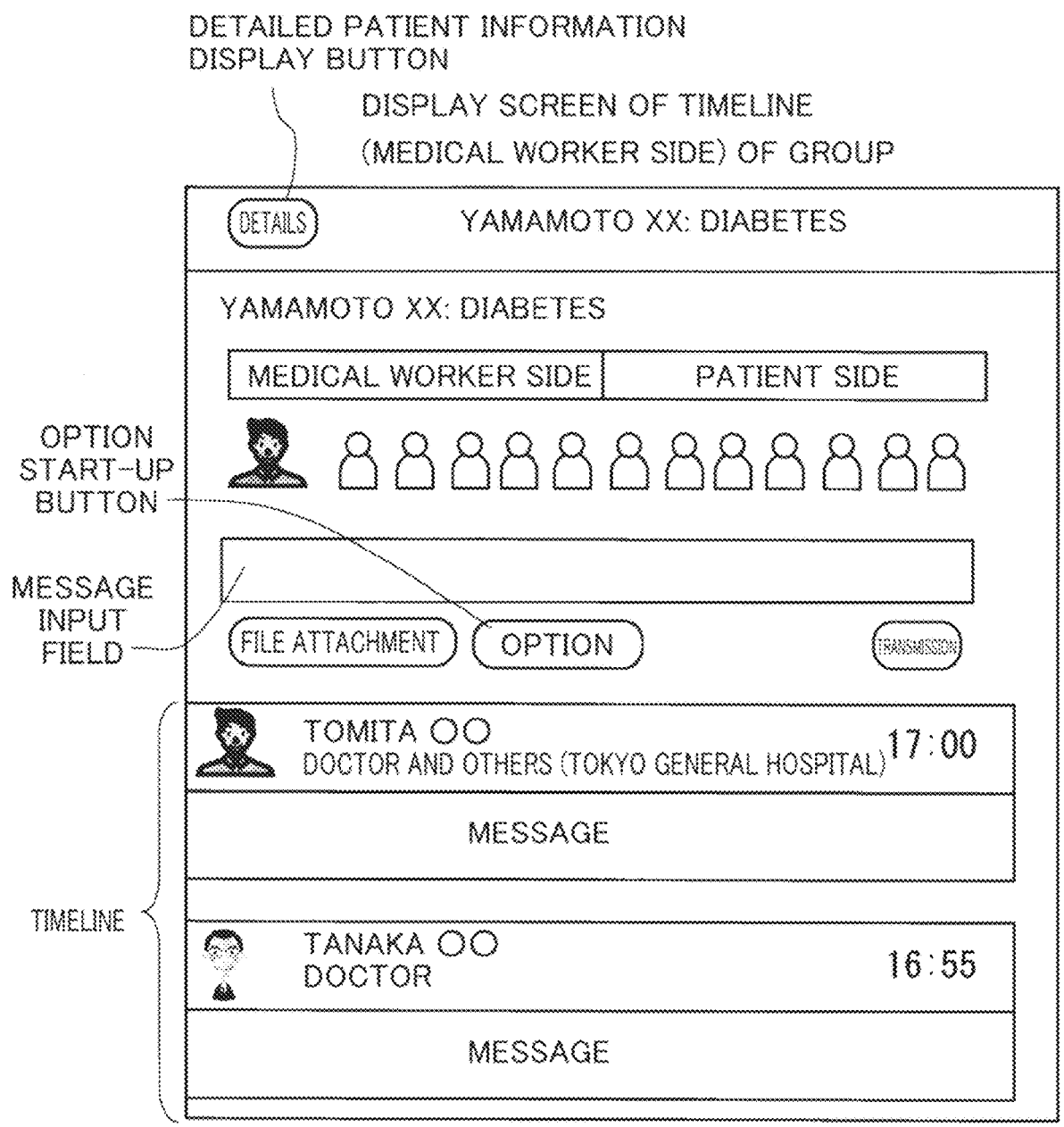
FIG. 18 is an illustrative view showing an example of a "display screen of a timeline of a group (medical worker side)" of the specific patient when the application is installed in the medical support system in which the service architecture support system according to the embodiment of the present invention is incorporated.

FIG. 17 shows an example of a timeline on a "home screen" presented by the medical support system 30 in a state where the new application 220 is uploaded and installed into the service architecture support system 100 from the developer terminal 13 so as to be able to be used. When among a plurality of messages displayed on the "home screen", a message for a specific patient P3 (here, Yamamoto XX who receives treatment of diabetes) is clicked by a medical worker M who is the primary doctor of the patient P3 (Yamamoto XX), the diabetes treatment group G31 of the patient P3 is selected, and the timeline (medical worker side) of the group G31G as shown in FIG. 18 is displayed on the medical worker terminal 11 of the medical worker M. The timeline (medical worker side) corresponds to the medical worker shared area 51b in the timeline of the group G11 in FIG. 9, only the medical worker M who is a group member of the diabetes treatment group G31 of the patient P3 can browse the timeline, and the patient P3 and the patient-related person R cannot browse the timeline. On the display screen of FIG. 18, an "option" button (option start-up button) is displayed. Then, when the medical worker M clicks the "option" button, an option selection screen (medical worker side) for application selection shown in FIG. 19 or an option selection screen (medical worker side) for request selection shown in FIG. 20 is displayed on the medical worker terminal 11. The option selection screen of FIG. 19 is displayed when an "app" tab is selected on the screen, whereas the option selection screen of FIG. 20 is displayed when a "request" tab is selected on the screen.

Figure 19:
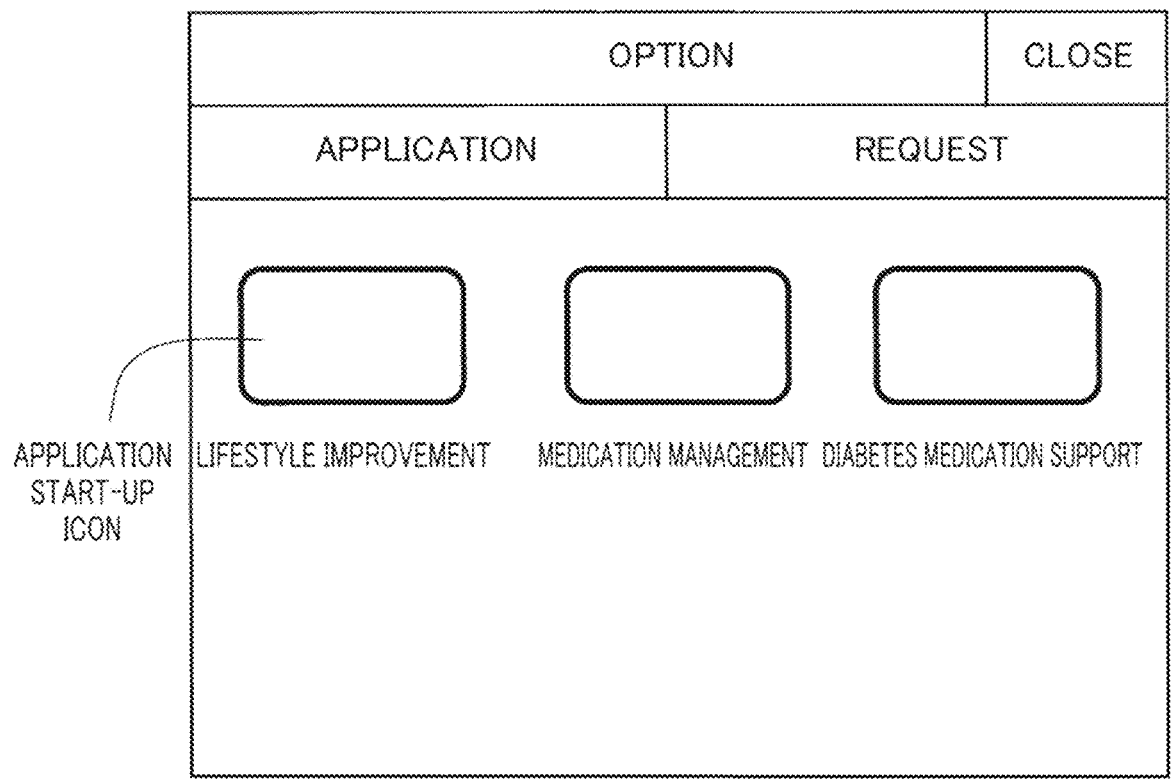
FIG. 19 is an illustrative view showing an example of an "medical worker side option selection screen" of the specific patient displayed when an option start-up button is clicked on the screen of FIG. 18, and shows a state where an application selection tab is selected.
Figure 20:
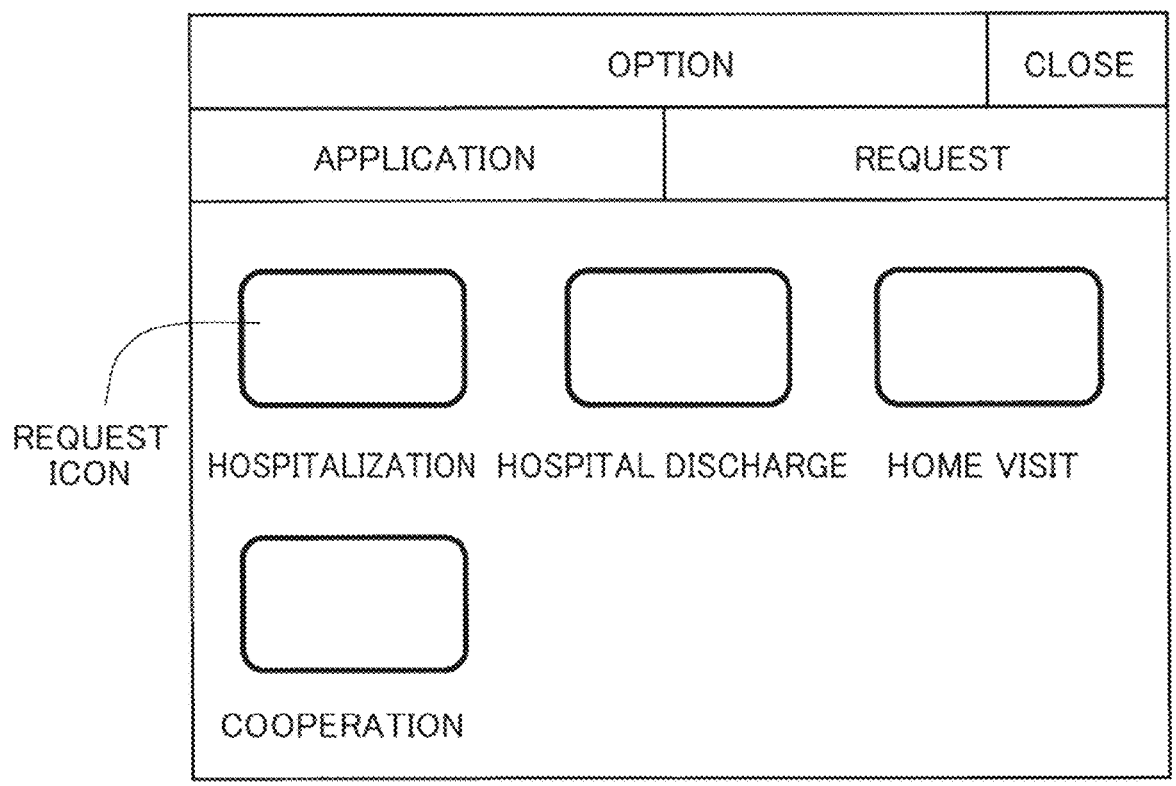
FIG. 20 is an illustrative view showing an example of the "medical worker side option selection screen" of the specific patient displayed on the timeline of the medical worker side when the option start-up button is clicked on the screen of FIG. 18, and shows a state where a request selection tab is selected.

The medical worker M who is the group member of the diabetes treatment group G31 of the patient P3 can select and utilize, from the option selection screen (medical worker side) of FIG. 19, one or more of three additional services (provided by the corresponding application 220) displayed on the screen, which are: "lifestyle improvement", "medication management" and "diabetes medication support". The medical worker M can also select and utilize, from the option selection screen (medical worker side) of FIG. 20, one or more of four additional services (also provided by the corresponding application 220) displayed on the screen, which are: "hospitalization", "hospital discharge", "home visit" and "cooperation".

Figure 21:
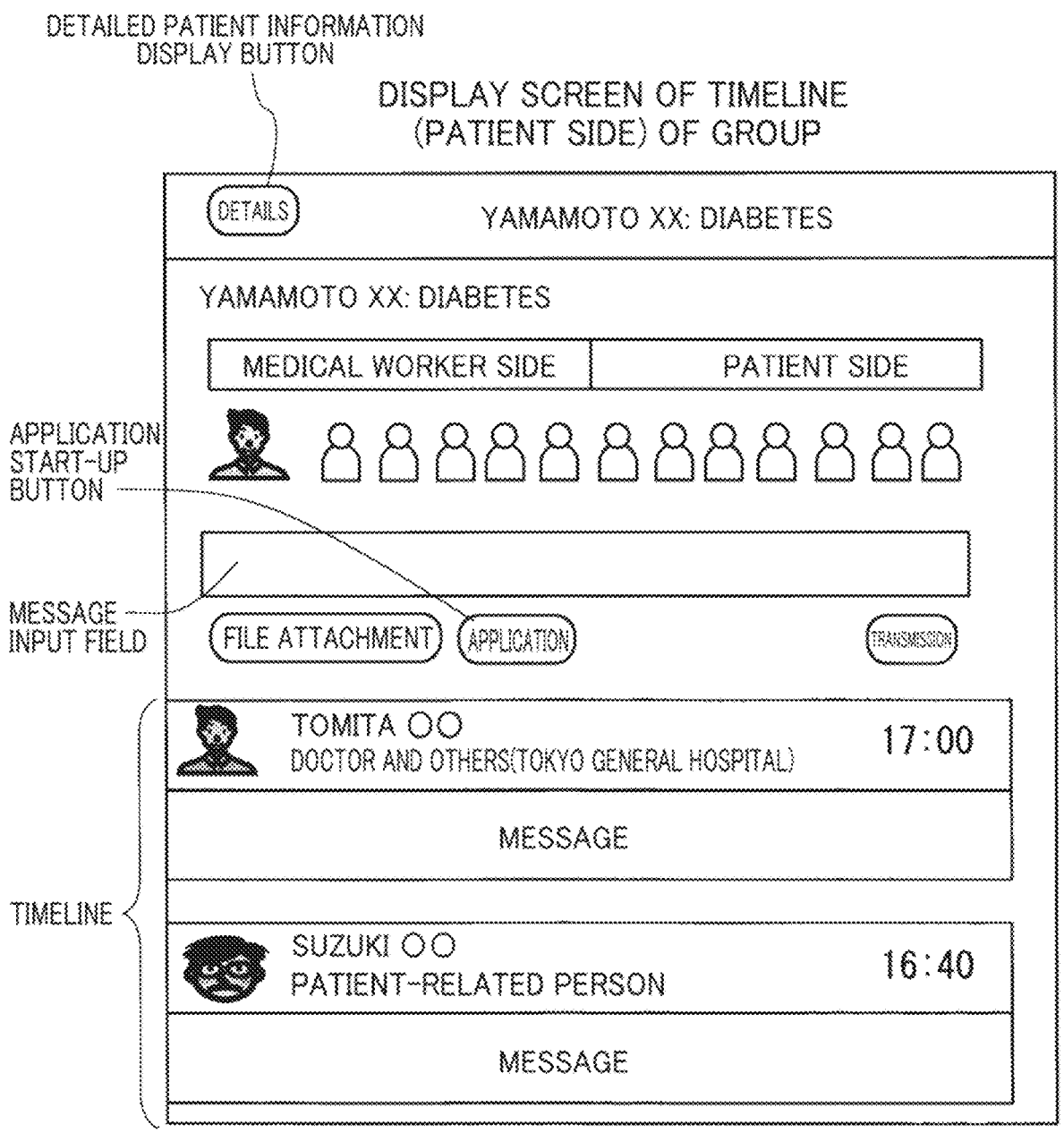
FIG. 21 is an illustrative view showing an example of a "display screen of a timeline (patient side) of a group" of the specific patient when the application is installed into the medical support system in which the service architecture support system according to the embodiment of the present invention is incorporated.

On the other hand, when on the "home screen" of FIG. 17, the message for the patient P3 is clicked by the patient P3, the diabetes treatment, group G31 of the patient P3 is selected, and thus the timeline (patient side) of the group G31 as shown in FIG. 21 is displayed on the patient terminal 10 of Mr. Yamamoto. The timeline (patient side) corresponds to the shared area for all members 51a in the timeline of the group G11 in FIG. 9, and can be browsed by all the group members (the patient P3, the patient-related person R and the medical worker M) of the group G31 of the patient P3. On this screen, an "app" button (app start-up button) is displayed. Then, when the "app" button is clicked, an option selection screen (patient side) for application selection shown in FIG. 22 is displayed on the patient terminal 10 of the patient P3.

Figure 22:
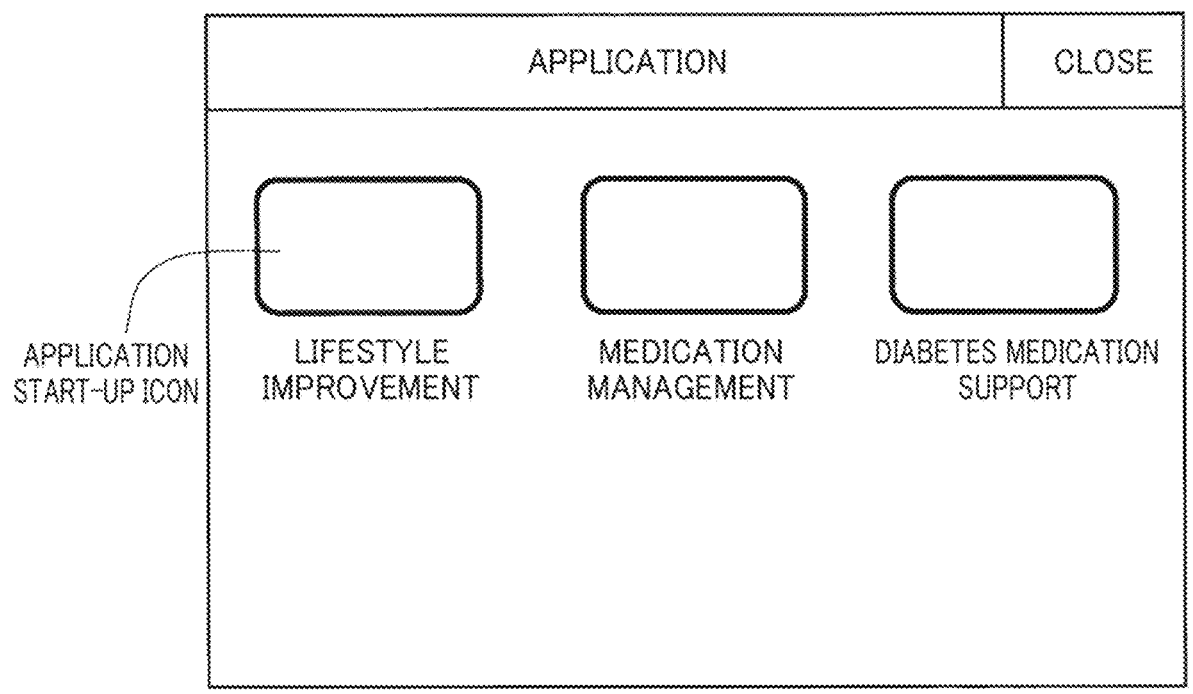
FIG. 22 is an illustrative view showing an example of an "patient side application selection screen" of the specific patient displayed when an application start-up button is clicked on the screen of FIG. 21.
Figure 30:
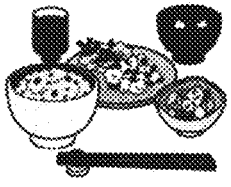
FIG. 30 is an illustrative view showing an example of an "a application management screen for system manager (additional function/diabetes advice settings)" when the application is installed into the medical support system in which the service architecture support system according to the embodiment of the present invention is incorporated.

The patient P3 can select and utilize, from the application selection screen (patient side) of FIG. 22, one or more of the three additional services (provided by the corresponding application 220) displayed on the screen, which are: "lifestyle improvement", "medication management" and "diabetes medication support". Since this screen is displayed on the patient side, the four additional services displayed on the medical worker side screen, which are: "hospitalization", "hospital discharge", "home visit" and "cooperation", are not displayed, with the result that the patient P3 naturally cannot utilize these additional services.

The patient-related person R who is a group member of the group G31 of the patient P3 can also select and utilize, from the application selection screen (patient side) of FIG. 22, one or more of the three additional services displayed on the screen, which are: "lifestyle improvement", "medication management" and "diabetes medication support".

As described above, all the applications 220 which are uploaded are incorporated and integrated into the medical support system 30, and thus the services provided by the applications 220 are associated with one or a plurality of groups G which are applied (which can be utilized) and are then registered as "additional services" within the medical support system 30. Hence, when the user (the patient P, the patient-related person R or the medical worker M) belonging to one or a plurality of groups G in which these applications 220 can be utilized wants to utilize the "additional service" which is introduced in the medical service utilized by the user, the user only selects and clicks the button (icon) of the corresponding "additional service" displayed on the user terminal 10, 11 or 12 of the user so as to be able to utilize the "additional service". The switching of additional services which are used and the stop of the utilization thereof are easily performed only by clicking similar, icons.

Hence, in the service architecture support system 100 having the configuration and the functions as described above, the applications 220 for providing various additional services can be efficiently developed and incorporated into the medical support system 30, and moreover, the incorporated additional services are divided into additional services applicable to the medical worker M and additional services applicable to the patient P and the patient-related person R so as to be additionally provided easily and individually. The side which utilizes the additional services only clicks, as necessary, on the user terminal 10, 11 or 12 of the side, the corresponding button displayed on the option selection screen or the application selection screen, and thereby can selectively utilize the desired additional service or stop the utilization, with the result that the service architecture support system 100 is very convenient and effective.

The "manager settings" and the "user settings" described previously which are necessary for bringing, with the applications 220, the additional services into a state where they can be utilized by the user as described above, will be described next in detail with reference to FIGS. 23 to 36. Here, as an example, a case is taken up where in the diabetes treatment group G31 of the patient P3 (Yamamoto XX), the additional service of "diabetes medication support" can be utilized. In this way, it is made clearer how the note module 211, the record module 212, the hearing module 213 and the book module 214 within the care unit 210a are operated within the application 220 (that is, the specific form of utilization of the models).

FIG. 23 shows, in a case where the application 220 for providing the additional service of "diabetes medication support" is installed into the medical support system 30 in which the service architecture support system 100 is incorporated, a display example of when the system manager A of the medical support system 30 executes the "manager settings process" for settings the basic information thereof on an "application management screen for system manager". When the "manager settings process" is executed, the "manager initial settings (first-stage initial settings)" is executed with the registration unit 111 of the service architecture support system 100 accordingly, with the result that the first-stage initial settings on the application 220 is completed as set in the "manager settings process".

As is clear from FIG. 23, the name of the application 220 is set to "diabetes medication support" by the system manager A, the category thereof is specified to "medication" and the authority to set items such as the details of questions in the application 220 is given to the system manager A, Dr. Koyama who is the primary doctor (the medical worker M) of the patient P3 (Yamamoto XX), and an external medical worker (external staff) who does not belong to the medical-related facility F to which Dr. Koyama belongs. The subsequent consultation date is set, the use of a progress summary describing an outline of the treatment progress is set, the function of: "medication confirmation (1 week)" is added as the description of the application 22, and "inspection record" in which the measurement value of a predetermined inspection item is recorded is enabled. Furthermore, since the patient side timeline of the group G31 of the patient P3 is specified as the available timeline of the application 22, information necessary for providing the diabetes medication support service, that is, "application element information" is posted on the patient side timeline of the group G31, and thus all the group members in the group G31 can browse the patient side timeline.

FIG. 24 shows a display example when in the "application management screen for system manager", medicines which can be used in the diabetes medication support service are set. Although in the figure, seven types of medicines which are taken for diabetes treatment by the patient P3 and the intakes thereof are set, this is specified in the diabetes medication support application 220. The medicines which are actually taken are selected and changed from among these medicines according to the time, (The change of the selected medicines is performed in the "manager settings process" which is executed by the system manager A.) Furthermore, the "medicine alarm" for medication time notification provided by the application 220 is set so as to be automatically posted on the timeline (patient side) of the group G31 of the patient P3, and the "medicine calendar" provided by the application 220 is also set so as to be used.

FIG. 25 shows a display example when in the "application management screen for system manager", additional functions are set. In this example, a total of eleven functions are provided by the diabetes medication support application 220, and the eleven functions are: a note function whose title is "complications, other symptoms", a hearing function whose title is "confirmation of symptoms causing anxiety", a hearing function whose title is "confirmation of exercise habits", a hearing function whose title is "confirmation of eating habits", a hearing function whose title is "confirmation of remaining medicine", a book function whose title is "diabetes advice (diet)", a book function whose title is "diabetes advice (exercise)", a book function whose title is "diabetes advice (knowledge/risk management)", a hearing function whose title is "confirmation of interaction", a hearing function whose title is "medication confirmation (1 week)" and a record function whose title is "inspection record". This indicates that the application 220 is produced with the four specific functions which are: the note function, the record function, the hearing function and the book function presented by the note module 211, the record module 212, the hearing module 213 and the book module 214. It is clear from this example how these four specific functions are actually utilized in the application 220.

In order for the eleven functions shown in FIG. 25 to be effectively utilized in the diabetes medication support service provided by the diabetes medication support application 220, it is necessary for the system manager A to make the first-stage initial settings. In some of these functions, in addition to the first-stage initial settings made by the system manager A, it is necessary for a specified user to make the second-stage initial settings.

In the note function "complications, other symptoms", the first-stage initial settings (manager initial settings) made by the system manager A are such that: (a) in the application management screen of FIG. 25 the function is set so as to be utilized a (b) in the application management screen of FIG. 29, the note title is set to, for example, "patient note", and items (recording items) which are recorded in the "patient note" are individually specified. By setting these two points, the manager initial settings are completed. When it is desired to change the details of the settings after the manager initial settings is completed in this way, the system manager A executes the "manager settings process" again, and thus such a settings change can be made.

Figure 46:
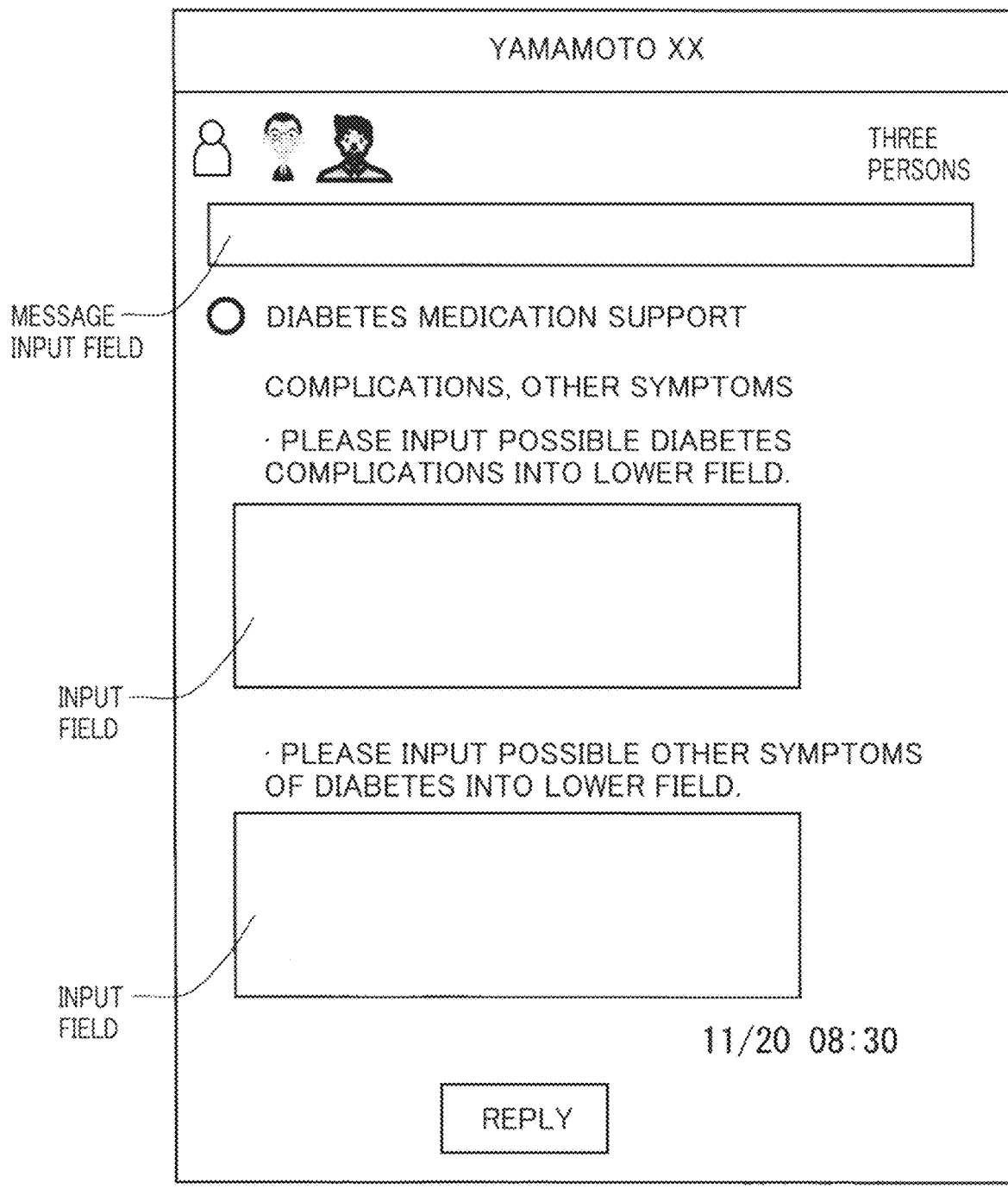
FIG. 46 is an illustrative view showing an example of a "display screen displayed on a timeline (medical worker side) of a group" of the specific patient when the application is installed into the medical support system in which the service architecture support system according to the embodiment of the present invention is incorporated.

However, in the note function: "complications, other symptoms", user initial settings (second-stage initial settings), in which the complications of diabetes and other symptoms of diabetes are input and set by the medical worker M serving as the user, are further needed. Hence, in this case, by means of the manager initial settings (first-stage initial settings) or by specifications within the application 220, on the patient-related person terminal 12 of the identified medical worker M, the medical worker side timeline of the group G31 of the patient P3 is displayed, and an information input screen as shown in FIG. 46 is displayed on the timeline. Hence, the identified medical worker M inputs the complications of diabetes and other symptoms of diabetes in input fields on the information input screen and clicks a "transmit" button, and thus the user initial settings are completed. The information which is input and transmitted in this way is stored in the application storage unit 332 of the medical support system 30. When the manager initial settings and the user initial settings are completed in this way, the note function "complications, other symptoms" can be utilized in the application 220.

In the hearing function whose title is "confirmation of symptoms causing anxiety", the manager initial settings are such that: (a) in the application management screen of FIG. 25, the function is set so as to be utilized, (fc) in the application management screen of FIG. 26, the respective items of function title, notification schedule and supplementary explanation are set, and a question to be presented is registered, (c) in the application management screen of FIG. 27, an answer type and an answer rule, a question title, an answer item, an additional message and a range of disclosure thereof are set and (d) in the application management screen of FIG. 28, an answer type and an answer rule, a question title and an answer item are set. By settings these four points, the manager initial settings are completed. The user initial settings are not needed, and thus in this way, the hearing function "confirmation of symptoms causing anxiety" can be utilized in the application 220.

In the hearing functions whose titles are "confirmation of exercise habits", "confirmation of eating habits" and "confirmation of remaining medicine", the manager initial settings are such that: (a) in the application management screen of FIG. 25, the function is set so as to be utilized and (b) in the application management screen (not shown) similar to FIGS. 27 to 29, according to the details of hearing (exercise habits, eating habits and remaining medicine), the settings of function title, notification schedule and supplementary explanation, the registration of a question, the settings of an answer type and an answer rule, the settings of a question title, the settings of an answer item and the like are performed as necessary. By making all these settings and the like, the manager initial settings are completed. The user initial settings are not needed, and thus in this way, these three hearing functions can be utilized in the application 220.

In the book function whose title is "diabetes advice (diet)", the manager initial settings are such that: (a) in the application management screen of FIG. 25, the function is set so as to be utilized and (b) in the application management screen of FIG. 30, advice (contents) for settings and transmission of a book title is selected (specified) and the necessary corrections are made. By settings these two points, the manager initial settings are completed.

Figure 47:
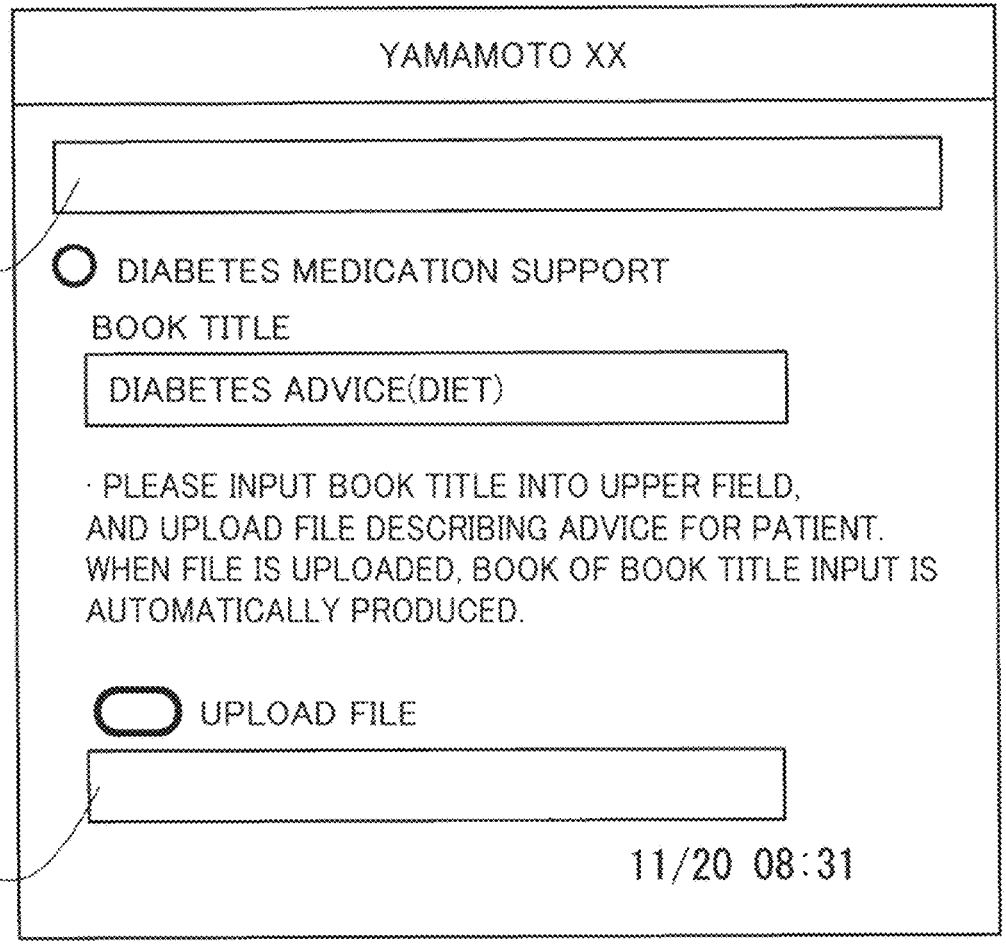
FIG. 47 is an illustrative view showing an example of the "display screen displayed on a timeline (medical worker side) of a group" of the specific patient when the application is installed into the medical support system in which the service architecture support system according to the embodiment of the present invention is incorporated.

In the book function whose title is "diabetes advice (diet)", in addition to the manager initial settings, user initial settings, in which a file (which is produced according to a predetermined format) describing advice (contents) is uploaded by the medical worker M, are further needed. In this case, by means of the specifications of the system manager A or by means of the specifications within the application 220, on the medical worker terminal 12 of the identified medical worker M, the medical worker side timeline of the group G31 of the patient P3 is displayed, and a file upload screen as shown in FIG. 47 is displayed on the timeline. Hence, the identified medical worker M inputs the book title on the screen and further uploads the file describing advice (contents), and thus the user initial settings are completed. In this way, the book function of "diabetes advice (diet)" can be utilized in the application 220.

In the book functions whose titles are "diabetes advice (exercise)" and "diabetes advice (knowledge/risk management)", the manager initial settings are such that: (a) in the application management screen of FIG. 25, the function is set so as to be utilized and (b) in the application management screen similar to FIG. 30, according to the details of the book (exercise and knowledge/risk management), advice (contents) for settings and transmission of a book title is selected (specified), and the necessary corrections are made. By setting these two points, the manager initial settings are completed.

In the book functions whose titles are "diabetes advice (exercise)" and "diabetes advice (knowledge/risk management)", in addition to the manager initial settings described above, as in the book function of "diabetes advice (diet)", user initial settings, in which a file (which Is produced according to a predetermined format) describing advice (contents) is uploaded by the medical worker M, are needed. In this case, the same file upload screen as in FIG. 47 is displayed on the medical worker side timeline of the group G31 of the patient P3. Hence, the identified medical worker M uploads, on the screen, as necessary, the file describing advice (contents) according to the details of the book (exercise and knowledge/risk management), and thus the user initial settings are completed. In this way, these two book functions can be utilized in the application 220.

In the record function whose title is "inspection record", the manager initial settings are such that: (a) in the application management screen of FIG. 25, function is set so as to be utilized and (fc) in the application management screen of FIG. 31, the settings of a record title and the selection (specifications) of the inspection item to be recorded are performed. By settings these two points, the manager initial settings are completed. The user initial settings are not needed, and thus in this way, the record function can be utilized in the application 220. The specifications of the information source of the inspection information are performed on another application management screen (not shown).

FIGS. 32 and 33 show an example of "notification of new settings" which are produced by the system manager A on the settings change of the application 220. The "notification of new settings" is posted on the timeline (patient side) of the group G31 which can be browsed by all the group members so that the initial settings of the function group described above in the application 220 that are made by the manager initial settings or the manager initial settings and the user initial settings, a settings change from the initial settings or a further settings change from the settings in the settings change is reported to all the group members of the group G31 of the patient P3. As is understood from FIGS. 32 and 33, the "notification of new settings" provides the following notifications on the new service of "diabetes medication support" provided by the application 220: (a) the usage period is from Dec. 1, 2017 to any completion date; (b) the authority (record/answer authority) to record (input) information in the new service and to answer a question is given to the patient (patient P), the family member and the friend of the patient (patient-related persons R) and the medical/care workers (medical worker M and care worker); (c) specifications of a medicine to be used and the medication time thereof and the display of inspection values; (d) measurement values of predetermined inspections are recorded on the patient note; (e) the range of disclosure of complications and other symptoms described in the notification schedule is all the group members of the group G of Mr. Yamamoto; (f) dates and times on which confirmation of symptoms causing anxiety, inspection record and confirmation of remaining medicine are performed are specified (changed).

FIG. 34 is the "application management screen for system manager" for setting the values of individual inspection items which are input into "inspection value" fields in the "notification of new settings" shown in FIG. 32. When the "manager settings process" is executed, the system manager A can input and set, on this screen, initial values, target values, reference value upper limits and reference value lower limits on three inspection items, which are HbA1c, weight and LDL cholesterol, and can further set whether or not the patient is alerted to (warned of) these inspection values. This applies to the manager initial settings.

FIG. 35 is the "application management screen for system manager" for setting the usage start date of the service which is input into a "usage period" field in the "notification of new settings" shown in FIG. 32. When the "manager settings process" is executed, the system manager A can set, on this screen, the usage start date of the service. This also applies to the manager initial settings.

Figure 36:
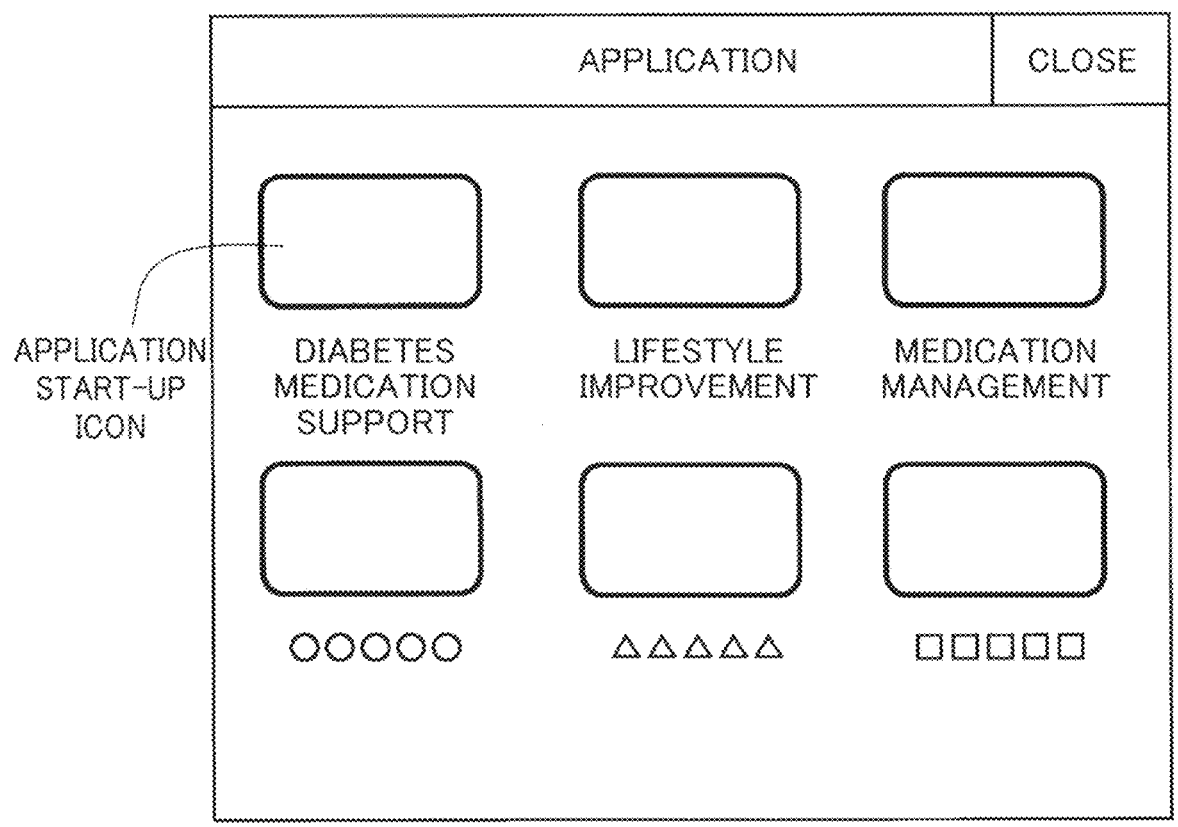
FIG. 36 is an illustrative view showing an example of an "application management screen for system manager (application selection)" when the application is installed into the medical support system in which the service architecture support system according to the embodiment of the present invention is incorporated.

FIG. 36 is the "application management screen for system manager" which indicates the icon list of a group of applications 220 installed into the medical support system 30. It is found that the system manager A can arbitrarily select and individually manage not only the diabetes medication support application 220 described above, but also another application 220 which is desired. The system manager A can manage, from this screen, which application 220 can be utilized in the medical support system 30.

FIGS. 37 to 45 show examples of the screen displayed on the timeline (patient side) of the diabetes treatment group G31 of the patient P3 when the diabetes medication support service provided by the diabetes medication support application 220 described above is received.

Figure 37:
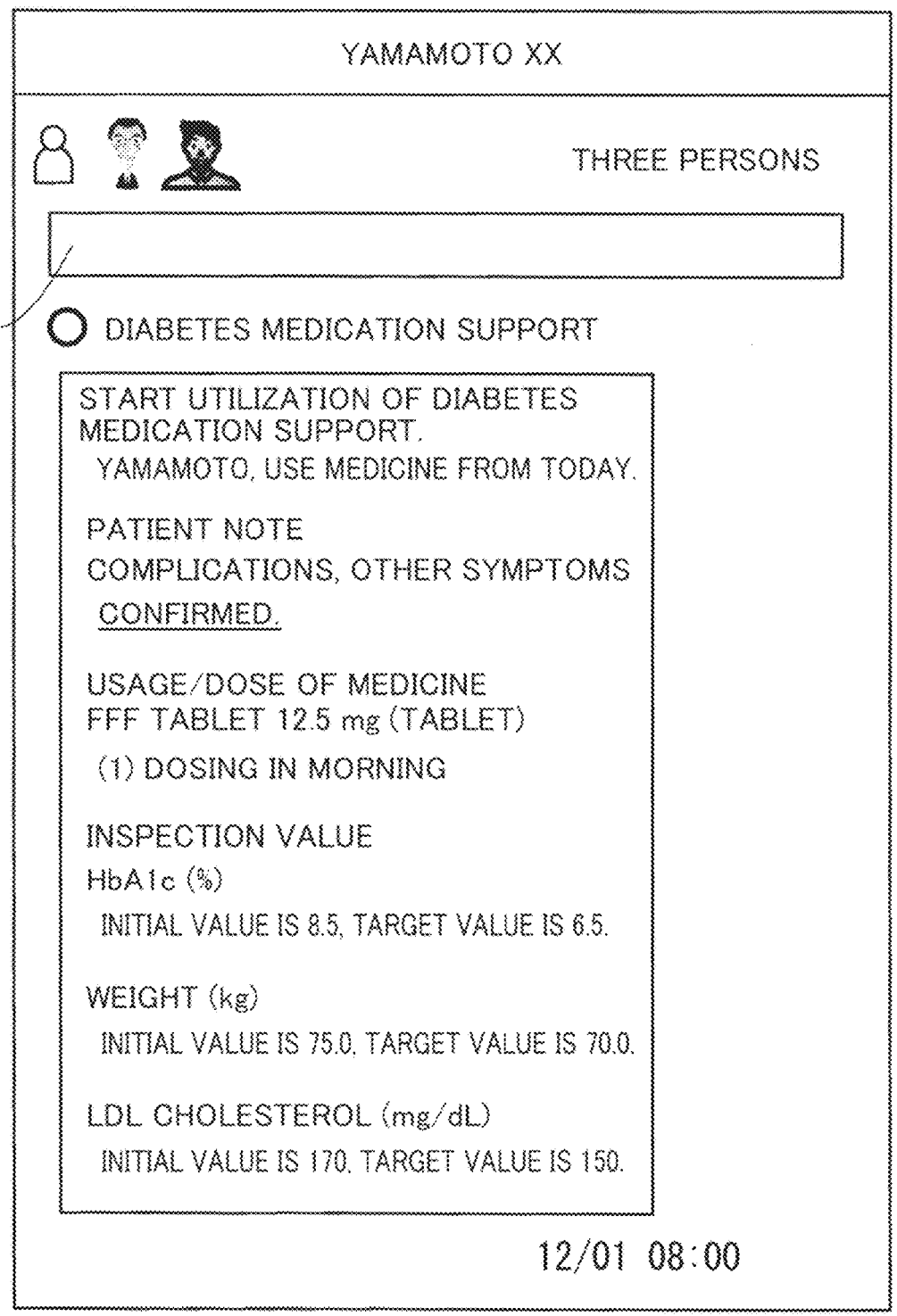
FIG. 37 is an illustrative view showing an example of the display screen of a timeline (patient side) of a group" of the specific patient when the application is installed into the medical support system in which the service architecture support system according to the embodiment of the present invention is incorporated.

FIG. 37 is a screen showing a state where a message (presentation information) indicating the usage start of the diabetes medication support service described above is posted (displayed) on the timeline (patient side) of the diabetes treatment group G31 of the patient P3. This message is realized by utilization of the message posting function of the medical support system 30. As is understood from FIG. 37, group members belonging to the group G31 are a total of three persons, which are the patient P3, the primary doctor of the patient P3 (medical worker M) and a family member of the patient P3 (patient-related person R), and all of them can browse the messages. This is because, as indicated in the application table shown in FIG. 16(d), the diabetes medication support application 220 described above (application ID=1) is associated with the diabetes treatment group G of the patient P3 (group ID=10003) and also because as indicated in the "application management screen for system manager" of FIG. 23, the "patient side timeline" is selected in the item of "usage range settings".

Figure 38:
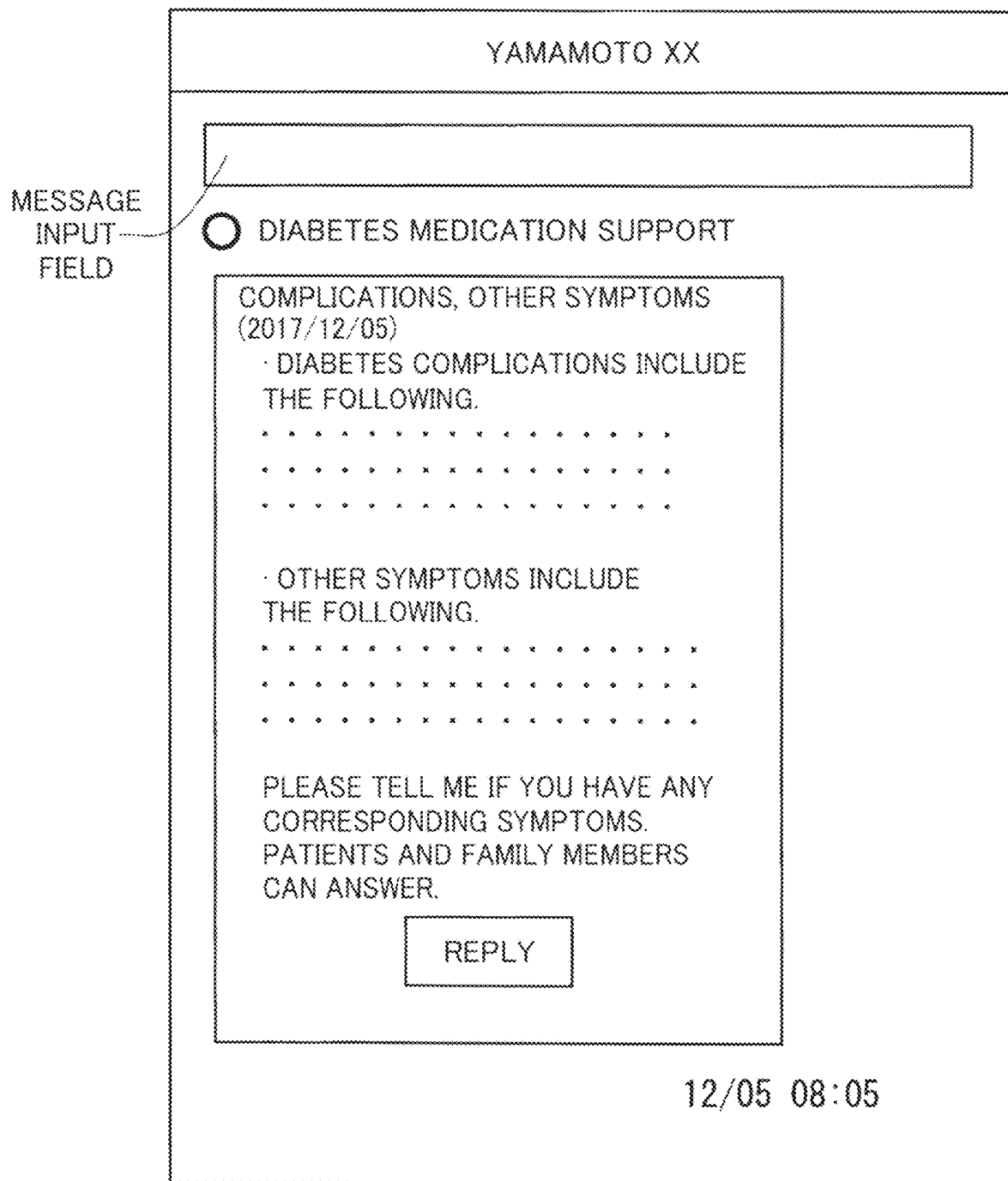
FIG. 38 is an illustrative view showing an example of the display screen of a timeline (patient side) of a group" of the specific patient when the application is installed into the medical support system in which the service architecture support system according to the embodiment of the present invention is incorporated.

In the diabetes medication support service usage start message of FIG. 37, in the item of "patient note", characters of "complications, other symptoms" and characters for "confirmed." are displayed, and when the characters for "confirmed." are clicked, the details of "complications, other symptoms" are displayed in another window, with the result that the patient P3 and the family member of the patient P3 (patient-related person R) read the characters so as to be able to easily check the complications and other symptoms. FIG. 38 shows a state where the details of "complications, other symptoms" are posted on the timeline of the group G31 of the patient P3. It is possible to read the details on the timeline as described above. This is realized by use of the note function (see FIG. 25) whose title is "complications, other symptoms". When the patient P3 has the corresponding symptoms, the patient P3 can reply (answer) from the screen of FIG. 38 to the medical worker M in charge. An example of the answer screen used in the reply is shown in FIG. 42. Preferably, on the answer screen, any one of two radio buttons is selected, and an appropriate message is input into a message input field.

In the item of "usage and dose of medicine" in the service usage start message of FIG. 37, the medicine and the usage thereof specified in the "application management screen for system manager" of FIG. 24 are reflected.

In the item of "inspection value" in the service usage start message of FIG. 37, the recording item of the inspection specified in the "application management screen for system manager" of FIG. 31 is reflected.

Figure 39:
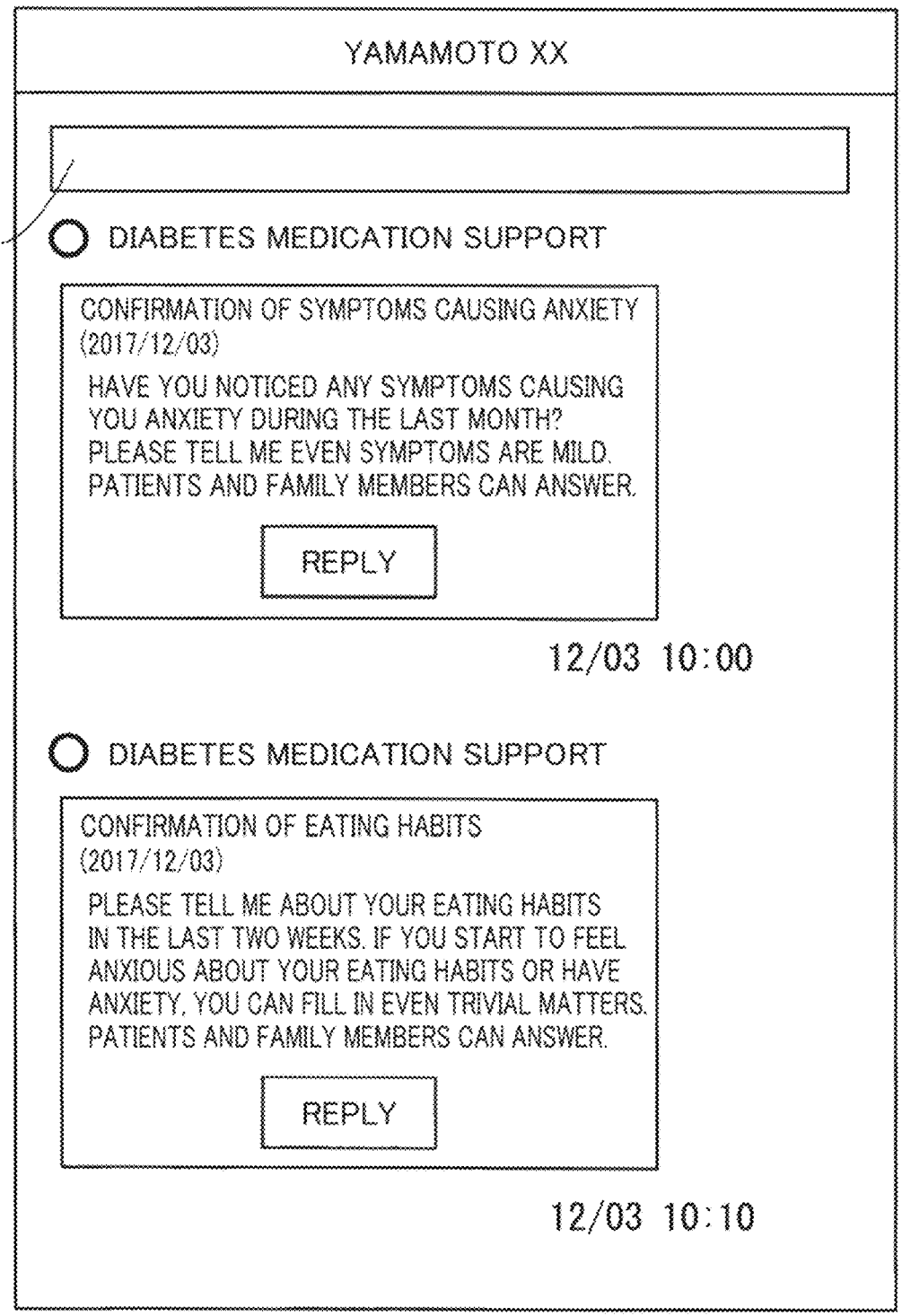
FIG. 39 is an illustrative view showing an example of the display screen of a timeline (patient side) of a group" of the specific patient when the application is installed into the medical support system in which the service architecture support system according to the embodiment of the present invention is incorporated.
Figure 43:
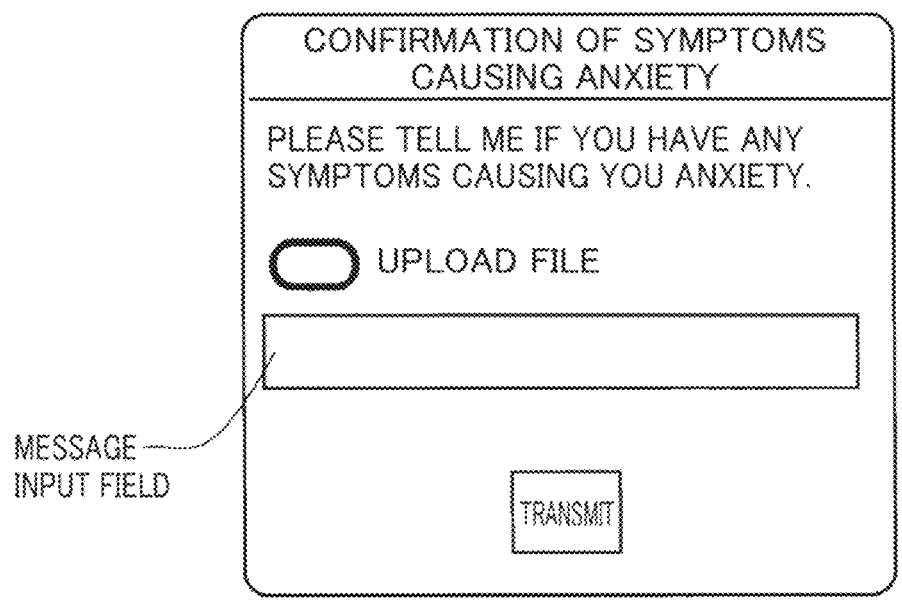
FIG. 43 is an illustrative view showing an example of the "answer screen displayed on a timeline (patient side) of a group" of the specific patient when the application is installed into the medical support system in which the service architecture support system according to the embodiment of the present invention is incorporated.

FIG. 39 shows ex state where in the diabetes medication support service described above, two question messages of "confirmation of symptoms causing anxiety" and "confirmation of eating habits" are posted on the timeline (patient side) of the group G31 of the patient P3. These question messages are realized by the two hearing functions of "confirmation of symptoms causing anxiety" and "confirmation of eating habits" described above and the message posting function of the medical support system 30. As is understood from the figure, an "answer" button displayed on each of the question messages is clicked, and thus the patient P3 or the family member (patient-related person R) can answer the question. An example of the answer screen used in the answer to the question of "confirmation of symptoms causing anxiety" is shown in FIG. 43. The answer screen is in written form, and an appropriate message can be input into a message input field, and a file can be uploaded. An example of the answer screen used in the answer to the question of "confirmation of eating habits" is shown in FIG. 44. The answer screen is a multiple-choice form in which one is selected from four choices.

Figure 40:
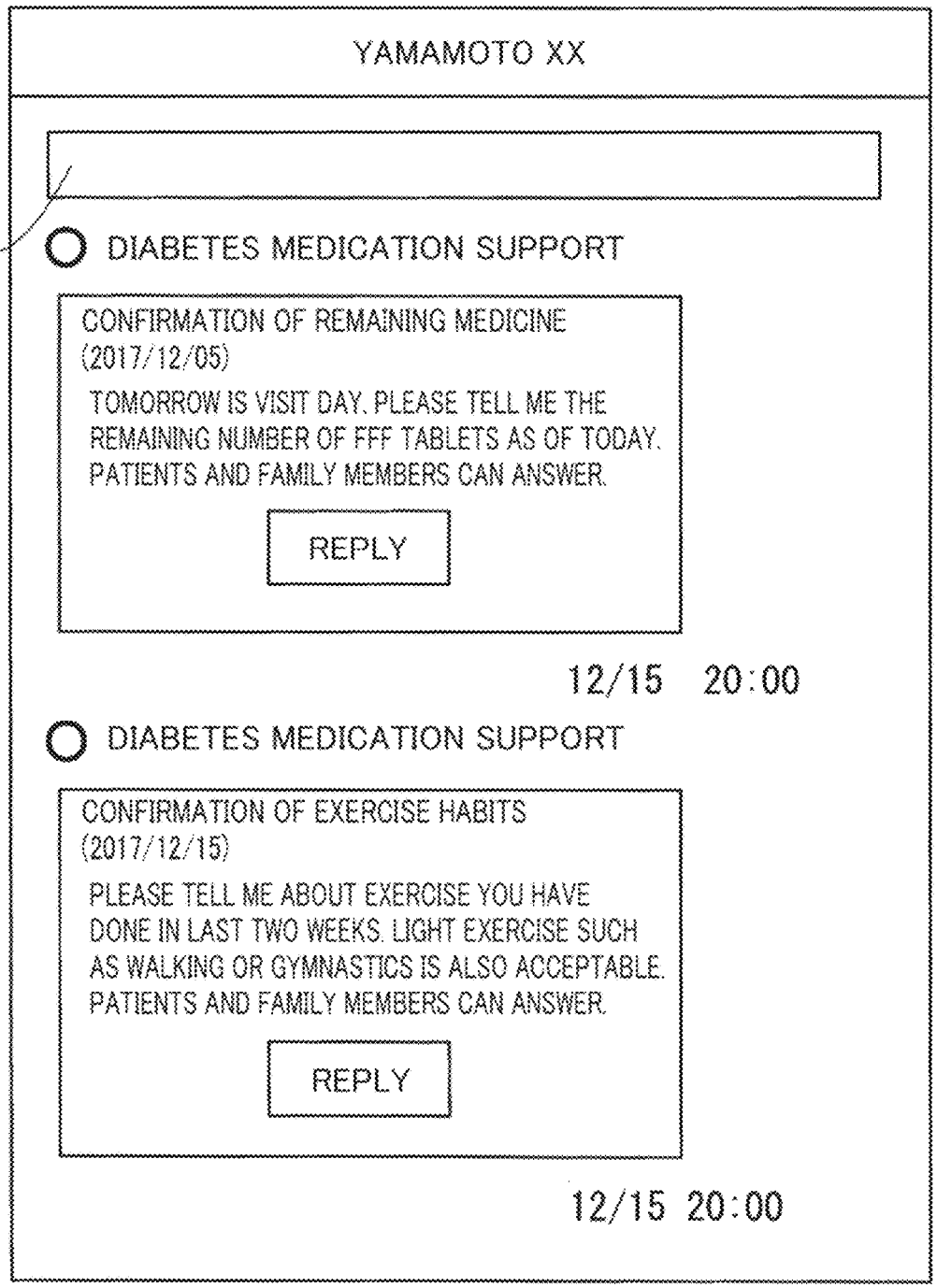
FIG. 40 is an illustrative view showing an example of the display screen of a timeline (patient side) of a group" of the specific patient when the application is installed into the medical support system in which the service architecture support system according to the embodiment of the present invention is incorporated.
Figure 45:
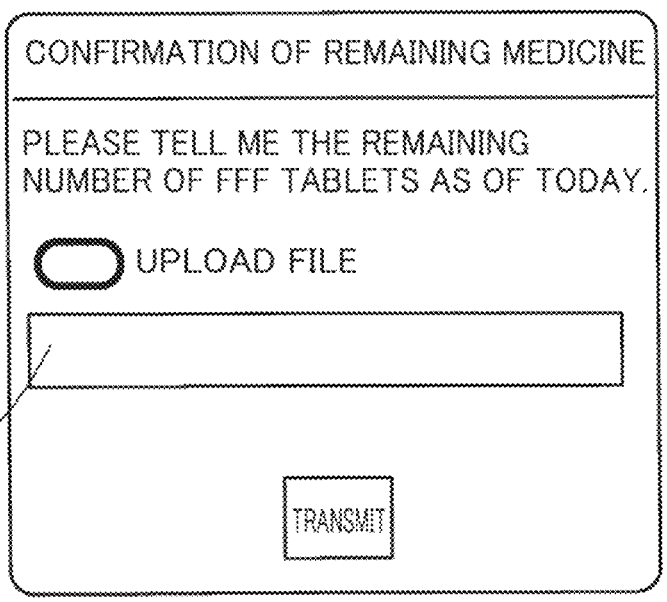
FIG. 45 is an illustrative view showing an example of an "answer screen displayed on a timeline (patient side) of a group" of the specific patient when the application is installed into the medical support system in which the service architecture support system according to the embodiment of the present invention is incorporated.

FIG. 40 is a screen showing a state where in the diabetes medication support service described above, two question messages of "confirmation of remaining medicine" and "confirmation of exercise habits" are posted on the timeline (patient side) of the group G31 of the patient P3. These question messages are realized by the two hearing functions of "confirmation of remaining medicine" and "confirmation of exercise habits" described above and the message posting function of the medical support system 30. As is understood from the figure, an "answer" button displayed on each of the question messages is clicked, and thus the patient P3 or the family member (patient-related person R) can answer the question. An example of the answer screen used in the answer to the question of "confirmation of remaining medicine" is shown in FIG. 45. The answer screen is a written form, and an appropriate message can be input into a message input field, and a file can be uploaded.

Figure 41:
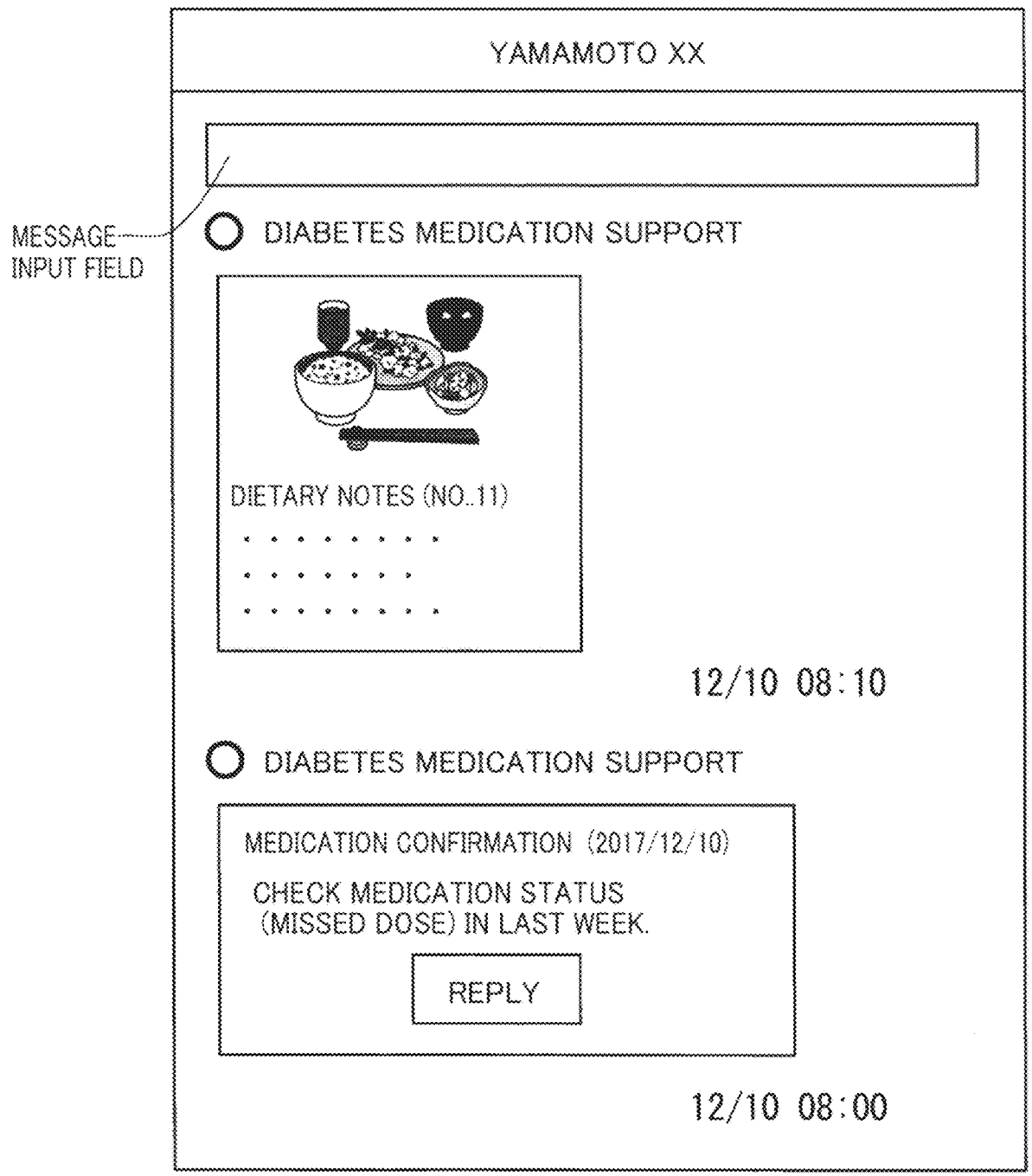
FIG. 41 is an illustrative view showing an example of the display screen of a timeline (patient side) of a group" of the specific patient when the application is installed into the medical support system in which the service architecture support system according to the embodiment of the present invention is incorporated.

FIG. 41 is a screen showing a state where in the diabetes medication support service described above, a presentation message of "dietary notes" and a question message of "medication confirmation" are posted on the timeline (patient-side) of the group G31 of the patient P3. The message of "dietary notes" is realized by the book function of "diabetes advice (diet)" described above and the message posting function of the medical support system 30. The question message of "medication confirmation" is realized by the hearing function of "medication confirmation" described above and the message posting function of the medical support system 30. As is understood from the figure, an "answer" button displayed on the question message of "medication confirmation" is clicked, and thus the patient P3 or the family member (patient-related person R) can answer the question.

(Advantages Obtained by Service Architecture Support System)

As has been described in detail above, in the service architecture support system 100 according to the embodiment of the present; invention, by means of the framework management unit 140, an application framework 200 is provided which provides the four specific functions (functions provided by the four modules 211, 212, 213 and 214) described above on the medical support system 30, and thus the applications 220 which provide various new services (for example, the diabetes medication support) can be developed by utilization of the application framework 200. When the application 220 (for example, the diabetes medication support application) which is developed by utilization of the application framework 200 and in which the specific function provided by the framework 200 is installed is incorporated into the medical support system 30, a unique application ID is assigned to the application 220, the application ID is stored so as to be associated with one or a plurality of group IDs and thus the new service of "diabetes medication support" provided by the application 220 is allowed to be utilized only by group members who belong to one or a plurality of groups G having one or a plurality of groups IDs associated with the application ID through the user terminal 10, 11 or 12 of the group members. Hence, the applications 220 are incorporated into the medical support system 30, and thus various new services can easily be added to the medical services provided by the system 30.

When the application 220 which is developed by utilization of the application framework 200 and in which the specific function is installed is incorporated into the medical support system 30, by means of the application management unit 110, the application ID is assigned to the application 220, the application ID is stored so as to be associated with one or a plurality of group IDs and thus the new service provided by the application 220 is allowed to be utilized only by the group members who belong to one or a plurality of groups G having one or a plurality of groups IDs associated with the application ID through the user terminal 10, 11 or 12 of the group members. Hence, it is possible to effectively utilize the feature of the medical support system 30 "in which one or a plurality of users of a medical service (including not only the patient P, but also the medical worker M) are selectively made to belong, as group members, to a group G generated for each target person (the patient or the care recipient) of a medical/care service, in which only the group members are allowed to browse medical information on the target person related to the group G and in which thus the medical information related to the target person can be shared among the group members while ensuring the privacy of the target person".

Furthermore, since the application framework 200 is provided on the medical support system 30, and thus various applications 220 can be developed by utilization of the application framework 200, it is possible to efficiently develop the application 220 which is operated on the medical support system 30 and which can effectively utilize the feature of the system 30. Moreover, in the application 220, the system manager A executes the "manager settings" or further executes the "user settings" as necessary, such that the four specific functions installed in the application 220 can be utilized on the medical, support system 30 and that in the "manager settings" and the "user settings", the details (practice conditions) of the specific functions are set according to the needs of the patient P related to one or a plurality of groups G associated with the application ID of the application 220 or the medical worker M related to the group G, with the result that it is possible to finely adjust the details of the new service provided by the application 220 after being incorporated into the medical support system 30 according to the needs of the patient P serving as the target person of the medical service or the medical worker M who provides the medical service.

Furthermore, when the application 220 is incorporated into the medical support system 30, by means of the application management unit 110, the unique application ID is assigned to the application 220, the application ID is stored so as to be associated with one or a plurality of group IDs and thus the new service provided by the application 220 is allowed to be utilized only by the group members who belong to one or a plurality of groups G having one or a plurality of groups IDs associated with the application ID through the user terminal 10, 11 or 12 of the group members. Hence, the group members in the group G generated for each target person (patient P) of the medical service can dynamically adjust, according to their needs, the start or stop of utilization of the new service provided by the application 220.

Furthermore, since group members belonging to each of the groups G provide an instruction, on the user terminal 10, 11 or 12 of the group members, as necessary, to a plurality of new services provided by a plurality of applications 220 having a plurality of application ids associated with the group ID of the group G so as to be able to selectively utilize the new services, when the group members in the group G generated for each target person (patient P) of the medical service selectively utilize, according to their needs, a plurality of new services provided by the application programs it is not necessary to repeat a complicated operation of logging in to and logging out of the medical support system 30.

Furthermore, the new service provided by the application 220 is utilized, and thus it is possible to browse information (application related information) provided by group members related to one or a plurality of groups G associated with the application ID of the application 220 together with the medical information on the patient P related to one or a plurality of the groups G, with the result that information which is not noticed when the application related information and the medical information are separately present is often noticed. In other words, the new service provided by the application 220 is added to existing medical services, and thus a synergistic effect is often provided. Consequently, it is possible to expect an enhanced effect as compared with a case where the new service and the existing medical services are separately provided.

(Variations)

The embodiment described above indicates a specific example of the present invention. Hence, it is needless to say that the present invention is not limited to this embodiment and that various variations are possible without departing from the spirit of the present invention.

For example, although in the embodiment described above, an example is described where the four function modules, which are the note module 211, the record module 212, the hearing module 213 and the book module 214 are provided within one unit, the present invention is not limited to this example. It is needless to say that a function module other than these function modules may be additionally provided or some of the modules may be deleted. The total number of function modules provided within one unit is not limited. The specific functions provided by the function modules can be changed as necessary.

Although in the embodiment described above, a case is described where additional medical services are newly provided by use of the applications 220 to the medical services provided by the medical support system 30, the present invention is not limited to this case. Additional care services may be newly provided by use of applications 220. The present invention can also be applied to a case where additional, care services and medical services are newly provided by use of applications to care services provided by a care support system. Furthermore, the present invention can also be applied to a case where additional medical services and/or care services are newly provided by use of applications 220 to medical services and care services provided by a medical/care support system.

When the present invention is applied to a care support system which provides care services to care recipients or a medical/care support system which provides both medical services and care services to patients or the care recipients, in the embodiment described above, the patient P, the patient-related person R, the medical worker M and the medical-related facility F can be respectively replaced with a care recipient, a care recipient-related person, a care worker and a care-related facility. "Care recipient" refers to a person who receives a care service, such as home-visit or in-house care, bathing care or rehabilitation from a care worker M belonging to any care-related facility. "Care worker" refers to a person who is engaged in any care business, such as a care worker, a care manager, or a helper. As the care-related facility, facilities of various types and sizes are present, such as a special elderly nursing home and a paid nursing home. It is clear that even in these cases, the effects of the present invention described above can be obtained.

INDUSTRIAL APPLICABILITY

The present invention can be applied to a medical support system which provides medical services to patients, a care support system which provides care services to care recipients and a medical/care support system which provides both medical services and care services to patients or care recipients. The present invention can be widely applied to fields in which various new services are preferably added, as necessary, to medical services and/or care services provided by these systems.

EXPLANATION OF REFERENCE NUMERALS

10 patient terminal
11 medical worker terminal
12 patient-related person terminal
13 developer terminal
14 manager terminal
20 Internet
30 medical support system
51 timeline
51*a* shared area for all members
51*b* medical worker shared area
100 service architecture support system
110 application management unit
111 registration unit
112 application information storage unit
120 unit management unit
121 registration unit
122 function control unit
130 module management unit
131 note module control unit
132 record module control unit
133 hearing module control unit
134 book module control unit
135 registration unit
140 framework management unit
200 application framework
210*a* care unit
210*b* community unit
211 note module
212 record module
213 hearing module
214 book module
215 basic function unit
220 application 310 user management unit
311 registration unit
312 user information storage unit
313 patient information storage unit
314 medical worker information storage unit
315 medical-related facility information storage unit
316 disease information storage unit
320 group management unit
321 registration unit
322 group information storage unit
323 group member information storage unit
324 invitation request control unit
325 invitation request information storage unit
326 timeline control unit
327 message control unit
328 regular facility information storage unit
329 sharing agreement information storage unit
330 patient existence verification unit
331 authentication unit
332 application storage unit
340 authentication unit
350 communication control unit
F medical-related facility
F1 clinic
F2 clinic
F3 hospital
F4 home-visit nursing station
G group
G11 group of patient P1 for diabetes treatment
G12 group of patient P1 for hyperlipidemia treatment
G13 group of patient P1 for gout treatment
G21 group of patient P2 for Alzheimer's disease treatment
G22 group of patient P2 for high blood pressure treatment
G31 group of patient P3 for diabetes treatment
M medical worker
M1, M2, M3, M4, M5, M6, M7, M8 medical worker
P patient
P1, P2, P3 patient
R patient-related person
R1, R2, R3, R4, R5, R6, R7, R8 patient-related person
A system manager
D developer

The invention claimed is:

1. A service architecture support method in a medical/care support system which is a method of supporting construction of a new service in a medical/care support system that allows medical/care information related to a patient or a care recipient to be browsed according to a request from a user terminal through a communication network with the user terminal so as to support provision of a medical/care service to the patient or the care recipient,
wherein user identification information is assigned to a user who utilizes the medical/care service through the user terminal and is stored,
service recipient identification information is assigned to the patient or the care recipient serving as the user, and the service recipient identification information is stored so as to be associated with the user identification information,
business worker identification information is assigned to a medical worker or a care worker serving as the user, and the business worker identification information is stored so as to be associated with the user identification information,
a group which has unique group identification information is generated according to an instruction from the user terminal so as to be associated with the service recipient identification information,
one or a plurality of the users are selectively made to belong to the group as group members according to an instruction from the user terminal such that the medical/care information of the patient or the care recipient corresponding to the service recipient identification information related to the group can be shared among the group members through the user terminal,
an application framework which provides one or a plurality of specific functions is provided on the medical/care support system such that an application program for providing the new service can be developed from a developer terminal by utilization of the application framework,
when the application program which is developed by the utilization of the application framework and in which one or a plurality of the specific functions are installed is incorporated into the medical/care support system, unique application identification information is assigned to the application program, and the application identification information is stored so as to be associated with one or a plurality of pieces of the group identification information such that only the group members who belong to one or a plurality of the groups having one or a plurality of pieces of the group identification information associated with the application identification information are allowed to utilize, through the user terminal, one or a plurality of the new services provided by the application program,
in the application program, a predetermined manager executes a predetermined manager setting such that one or a plurality of the specific functions installed in the application program can be utilized on the medical/care support system, and in the manager setting, one or a plurality of the specific functions are set according to a need of the patient or the care recipient related to one or a plurality of the groups associated with the application identification information of the application program or the medical worker or the care worker related to the groups, and
the group members belonging to each of the groups provide, as necessary, an instruction on the user terminal so as to be able to selectively utilize a plurality of the new services vided by a plurality of the application programs having a plurality of pieces of the application identification information associate with the group identification information of the group.

2. The service architecture support method according to claim 1, wherein a necessary user setting is executed in addition to the manager setting such that the application program can be utilized on the medical/care support system, and
the user setting is executed by any one of the users related to one or a plurality of the groups associated with the application identification information of the application program.

3. The service architecture support method according to claim 1, wherein the application program describes a combination of one or a plurality of the specific functions needed to achieve a purpose of the application program and which is provided by the application framework.

4. The service architecture support method according to claim 1, wherein one or a plurality of the application programs associated with each of the groups sequentially display, on the user terminal, according to a predetermined schedule, service element information necessary for the new service provided by the application program on a timeline in which the medical/care information of the patient or the care recipient related to the group can be browsed, and when it is necessary to reply to the service element information, reply information is displayed from the user terminal on the timeline or is transmitted to the medical/care support system so as to reply to the service element information.

5. The service architecture support method according to claim 1, wherein the application framework includes, as a section which realizes one or a plurality of the specific functions, a first module which provides a function of storing predetermined as-needed information, a second module which provides a function of collecting and storing predetermined external information, a third module which provides a question-and-answer function and a fourth module which provides a function of storing content information.

6. The service architecture support method according to claim 1, wherein the application framework includes a plurality of units whose purposes are different from each other, and one or a plurality of the specific functions are provided in each of a plurality of the units.

7. A service architecture support system in a medical care support system which is a system for supporting construction of a new service in a medical/care support system that allows medical/care information related to a patient or a care recipient to be browsed according to a request from a user terminal through a communication network with the user terminal so as to support provision of a medical/care service to the patient or the care recipient, the service architecture support system comprising:

a user identification information storage section which stores and assigns user identification information to a user who utilizes the medical/care service through the user terminal;

a service recipient identification information storage section which assigns service recipient identification information to the patient or the care recipient serving as the user, and which stores the se recipient identification information such that the service recipient identification information is associated with the user identification information;

a business worker identification information storage section which, assigns business worker identification information to a medical worker or a care worker serving as the user, and which stores the business worker identification information such that the business worker identification information is associated with the user identification information;

a group management section that generates, according to an instruction from the user terminal, a group which has unique group identification information such that the group s associated with the service recipient identification information;

a group member selection section which selectively makes one or a plurality of the users belong to the group as group members according to an instruction from the user terminal such that the medical/care info nation of the patient care recipient corresponding to the service recipient identification information related to the group can be shared among the group members through the user terminal;

a frame framework management section that provides an application framework which provides one or a plurality of specific functions on the medical/care support system such that an application program for providing the new service can be developed from a developer terminal by utilization of the application framework; and application management section here het the application program which is developed by the utilization of the application framework and in which one or a plurality of the specific functions are installed is incorporated into the medical/care support system, unique application identification information is assigned to the application program, and where the application identification information is stored so as to be associated with one or a plurality of pieces of the group identification information such that only the group members who belong to one or a plurality of the groups having one or a plurality of pieces of the group identification information associated with the application identification information are allowed to utilize, through the user terminal, one or a plurality of the new services provided by the application program, wherein, in the application program, a predetermined manager executes a predetermined manager sett ng such that one or a plurality of the specific functions installed in the application program can be utilized on the medical/care support system, and in the manager setting, one or a plurality of the specific functions are set according to a need of the patient or the care recipient related to one or a plurality of the groups associated with the application identification information of the application program or the medical worker or the care worker related to the groups, and the group members belonging to each of the group s provide, as necessary, an instruction on the user terminal so as to be able to selectively utilize a plurality of the new services provided by a plurality of the application programs having a plurality of pieces of the application identification information associated with the group identification information of the group.

8. The service architecture support system according to claim 7, wherein a necessary user setting is executed in addition to the manager setting such that the application program can be utilized on the medical/care support system, and the user setting is executed b any one of the users related to one or a plurality of the groups associated with the application identification information of the application program.

9. The service architecture support system according to claim wherein the application program describes a combination of one or a plurality of the specific functions needed to achieve a purpose of the application program and which is provided by the application framework.

10. The service architecture support system according to claim 7, wherein one or a plurality of the application programs associated with each of the groups sequentially display, on the user terminal, according to a predetermined schedule, service element information necessary for the new service provided by the application program on a timeline in which the medical/care information of the patient or the care recipient related to the group can be browsed, and when it is necessary to reply to the service element information, reply information is displayed from the user terminal on the timeline or is transmitted to the medical/care support system so as to reply to the service element information.

11. The service architecture support system according to claim 7, wherein the application framework includes, as a section which realizes one or a plurality of the specific functions, a first module which provides a function of storing predetermined as-needed information, a second module which provides a function of collecting and storing predetermined external information, a third module which provides a question-and-answer function and a fourth module which provides a function of storing content information.

12. The service architecture support system according to claim 7, wherein the application framework includes a plurality of units whose purposes are different from each other, and one or a plurality of the specific functions are provided in each of a plurality of the units.

* * * * *